United States Patent
Fung et al.

(10) Patent No.: US 9,604,924 B2
(45) Date of Patent: Mar. 28, 2017

(54) SUBSTITUTED BIARYL SULFONAMIDES AND THE USE THEREOF

(71) Applicant: NovoMedix, LLC, San Diego, CA (US)

(72) Inventors: Leah M. Fung, San Diego, CA (US); Kyle W. H. Chan, San Diego, CA (US); Cathy A. Swindlehurst, San Diego, CA (US); Robert W. Sullivan, Vista, CA (US)

(73) Assignee: NovoMedix, LLC, San Diego, CA (US)

( * ) Notice: Subject to any disclaimer, the term of this patent is extended or adjusted under 35 U.S.C. 154(b) by 0 days.

(21) Appl. No.: 14/871,472

(22) Filed: Sep. 30, 2015

(65) Prior Publication Data

US 2016/0016899 A1  Jan. 21, 2016

Related U.S. Application Data

(62) Division of application No. 14/092,425, filed on Nov. 27, 2013, now Pat. No. 9,156,781.

(60) Provisional application No. 61/732,218, filed on Nov. 30, 2012.

(51) Int. Cl.
| | | |
|---|---|---|
| *A01N 41/06* | (2006.01) | |
| *A61K 31/18* | (2006.01) | |
| *C07C 311/21* | (2006.01) | |
| *A61K 31/337* | (2006.01) | |
| *A61K 45/06* | (2006.01) | |

(52) U.S. Cl.
CPC ............ *C07C 311/21* (2013.01); *A61K 31/18* (2013.01); *A61K 31/337* (2013.01); *A61K 45/06* (2013.01)

(58) Field of Classification Search
None
See application file for complete search history.

(56) References Cited

U.S. PATENT DOCUMENTS

| 3,322,828 A | 5/1967 | Muth et al. |
| 2013/0116317 A1 | 5/2013 | Fung et al. |

FOREIGN PATENT DOCUMENTS

| FR | 1 379 918 A | 11/1964 |
| GB | 0985748 A | 3/1965 |
| JP | 2 072151 A | 3/1990 |
| WO | 03/007955 A2 | 1/2003 |

OTHER PUBLICATIONS

Barnes et al., "Myofibroblast differentiation during fibrosis: Role of NAD(P)H oxidases," Kidney Int. 79:944-956 (2011).
Berge et al., "Pharmaceutical salts," J. Pharm. Sci. 66:1-19 (1977).
CAS registry No. 554439-85-9, published Jul. 25, 2003.
CAS registry No. 685110-13-8, published May 24, 2004.
CAS registry Nos. 1057883-96-1 and 1057727-49-7, published Oct. 7, 2008.
Cas registry Nos. 900905-74-0, 900905-72-8, 900905-64-8 and 900905-42-2, published Aug. 13, 2006.
Hinz et al., "Recent developments in myofibroblast biology: paradigms for connective tissue remodeling," Am. J. Pathol. 180:1340-1355 (2012).
Khamis et al., "Active roles of tumor stroma in breast cancer metastasis," Int. J. Breast Cancer 2012:574025 (2012).
Namba et al., "Design and synthesis of benzenesulfonanilides active against methicillin-resistant *Staphylococcus aureus* and vancomycin-resistant *Enterococcus*," Bioorg. Med. Chem. 16(11):6131-6144 (2008) (Epub Apr. 24, 2008).
Still et al., "Rapid chromatographic technique for preparative separations with moderate resolution," J. Org. Chem. 43: 2923-2925 (1978).
Therasse et al., "New guidelines to evaluate the response to treatment in solid tumors," J. Natl. Cancer Inst. 92:205-216 (2000).

*Primary Examiner* — Jeffrey S Lundgren
*Assistant Examiner* — Stephanie Springer
(74) *Attorney, Agent, or Firm* — Jones Day

(57) ABSTRACT

Provided herein are substituted biaryl sulfonamide compounds, pharmaceutical compositions comprising the compounds, methods of their preparation, and methods of their use. The compounds provided herein are useful for the treatment, prevention, and/or amelioration of various disorders, including cancer and proliferative disorders. In one embodiment, the compounds provided herein modulate initiation of protein translation. In one embodiment, the compounds provided herein are used in combination with surgery, radiation therapy, immuno therapy and/or one or more additional anticancer drugs for the treatment, prevention, and/or amelioration of cancer and proliferative disorders.

24 Claims, 6 Drawing Sheets

α-SMOOTH MUSCLE ACTIN (α-SMA) WESTERN BLOT ON

NORMAL HUMAN LUNG FIBROBLASTS (NHLF)

MDA-MB-231 Xenograft

Oral Efficacy of Compounds 1 and 2

SUBSTITUTED BIARYL SULFONAMIDES AND THE USE THEREOF

CROSS REFERENCE TO RELATED APPLICATIONS

This application is a divisional application of U.S. application Ser. No. 14/092,425, filed Nov. 27, 2013; which claims the benefit of U.S. Provisional Patent Application No. 61/732,218, filed Nov. 30, 2012; the disclosure of each of which is incorporated herein by reference in its entirety.

FIELD

Provided herein are substituted biaryl sulfonamide compounds, pharmaceutical compositions comprising the compounds, methods of their preparation, and methods of their use. The compounds provided herein are useful for the treatment, prevention, and/or amelioration of various disorders, including cancer, proliferative disorders, and angiogenesis mediated diseases.

BACKGROUND

Cancer is a major worldwide public health problem; in the United States alone, approximately 574,000 people died of cancer in 2010. See, e.g., U.S. Mortality Data 2010, National Center for Health Statistics, Centers for Disease Control and Prevention (2010). Many types of cancer have been described in the medical literature. Examples include cancer of blood, bone, skin, lung, colon, breast, prostate, ovary, brain, kidney, bladder, pancreas, and liver, among others. The incidence of cancer continues to climb as the general population ages and as new forms of cancer develop. A continuing need exists for effective therapies to treat subjects with cancer. Breast cancer is one of the most common types of cancer, especially among women. In the United States, it is estimated that there will be about 230,000 new cases of breast cancer and about 40,000 deaths from breast cancer in 2012. See, e.g., Breast Cancer Statistics, National Cancer Institute (2012), available at www.cancer.gov. Among different types of breast cancer, triple negative breast cancer (estrogen receptor (ER)/progesterone receptor/HER-2 negative) is more aggressive than other breast cancer subtypes. No targeted therapy exists for triple negative breast cancer. Triple negative breast cancer has a higher rate of recurrence resulting in death, although the tumors initially appear to respond to chemotherapy. Clearly there is a need to develop effective targeted therapy for triple negative breast cancer.

Changes in protein synthesis are directly linked to multiple human cancers. Translation initiation is deregulated in many cancers, including, e.g., lymphoma, breast cancer, head and neck cancer, colorectal cancer, lung cancer, bladder cancer, cervical cancer, and prostate cancer. Many proteins supporting the high rate of cancer cell growth, proliferation, and survival are translated from mRNAs having secondary structures, which have a greater dependence on rate-limiting translation factors such as eukaryotic initiation factor 4E (eIF4E). eIF4E overexpression in tumors can be a predictor for relapse in breast cancer regardless of nodal status and for drug resistance to adjuvant chemotherapy. A high percentage (>60%) of triple negative breast tumors express high levels of eIF4E. The patient group with high levels of eIF4E has a 1.6-fold higher rate of recurrence and a 2.1-fold increase in relative risk for cancer death. High levels of eIF4E drive the translation of proteins responsible for cancer initiation and progression resulting in aggressive phenotypes and enabling the tumors to better survive radiation treatment and chemotherapy. Therefore, it is desirable to regulate protein translation in cancer, in particular, inhibit the rate-limiting steps in protein translation in order to control cell growth and proliferation.

eIF4E, the rate-limiting factor for eukaryotic protein translation initiation, is ubiquitously expressed in multiple breast cancer cell lines. The activity and availability of eIF4E are controlled, e.g., by binding proteins such as 4E-BP1. The activity of these binding proteins is in turn regulated by phosphorylation, particularly by mTOR. eIF4E over-expression along with the concomitant enhanced translation initiation drives cellular transformation and tumorigenesis. eIF4E is a convergence point for many oncogenic pathways and a key factor for malignancy in human cancer tissues and in experimental cancer models. Enhanced translation initiation is found in malignant breast phenotypes. eIF4E over-expression leads to breast carcinoma angiogenesis and progression. eIF4E elevation of 7-fold or more is a strong independent prognostic indicator for breast cancer relapse and death in retrospective and prospective studies. Antisense oligonucleotide therapy down-regulating eIF4E resulted in a reduction of in vivo tumor growth in PC-3 prostate and MDA-MB-231 breast cancer models in mice. No toxicity was observed when 80% knockdown was observed in essential organs, suggesting tumors are more sensitive to translation initiation inhibition than normal tissue.

Translation initiation factor eIF4E and its binding protein 4E-BP1 are major downstream effectors of the PI3K/Akt/mTOR pathway. mTOR and other members of the PI3K/Akt/mTOR family control the establishment and maintenance of cancer phenotypes. The PI3K/Akt/mTOR pathway has been clinically validated as a target for cancer therapies. Overactivation of PI3K and Akt is found in a wide range of tumor types. PI3K catalyzes the production of phosphatidylinositol-3,4,5-trisphosphate. This lipid activates Akt protein kinase, which in turn triggers a cascade of responses ranging from cell growth and proliferation to survival and motility. PTEN, a dual specificity phosphatase, is an inhibitor of the PI3K pathway. Second to p53, PTEN is most frequently mutated or deleted in human tumors. Several PI3K inhibitors have been developed in clinical trials. mTOR controls translation initiation through phosphorylation and inactivation of 4E-BP binding protein, thereby activating eIF4E. Activation of eIF4E is required for the translation initiation of mRNAs that have long structured '5-untranslated regions. Increasing evidence suggests that mTOR, as a central regulator of cell growth and proliferation, controls protein biosynthesis. The mTOR pathway controls translation of mRNAs encoding proteins such as cyclin D1, c-Myc, and ornithine decarboxylase that are essential for G1 cell-cycle progression and S-phase initiation. Inhibition of mTOR results in G1 cell cycle arrest. Rapamycin, an mTOR inhibitor, has significant antitumor activity against many tumor cell lines in the NCI screening as well as in humans. However, formulation, solubility and stability issues have hindered the development of rapamycin. Analogs of rapamycin have been developed to address these issues and have shown promising results in Phase II/III clinical trials. There remains a need for alternative cancer therapeutic agents that are effective and safe, e.g., agents having maximum inhibition of tumor growth, minimal toxicity to normal cells, and minimal on-target side effects in the treated subjects.

Excessive and persistent activation of cells characterizes both cancer and fibrotic diseases. Fibrosis is the formation of excess fibrous connective tissue in an organ or tissue in a reparative or reactive process, which can be benign (e.g., wound healing) or pathological. The term fibrosis is often used to indicate a pathological state of excess deposition of connective tissue, which can lead to loss of function and organ failure. During wound healing myofibroblasts are specialized cells that acquire smooth muscle features (including α-smooth muscle actin) and are important contributors to tissue repair. Myofibroblasts can be derived from fibroblasts, epithelial cells, and endothelial cells and are characterized by their ability to secrete extracellular matrix. Regardless of their origin, TGF-β is the principle growth factor responsible for differentiation to the myofibroblast activated phenotype (J L Barnes, Y Gorin, *Myofibroblast Differentiation During Fibrosis: Role of NAD(P)H Oxidases*, Kidney Int. 2011, 79: 944-956). During normal tissue repair myofibroblasts are activated in a controlled and transient manner (Hinz B. et al., *Recent developments in myofibroblast biology: paradigms for connective tissue remodeling*, Am J Pathol. 2012, 180:1340-55). However, excessive and persistent activation of myofibroblasts plays a key role in both fibrotic disease and cancer. In fibrotic disease, large numbers of myofibroblasts accumulate and are responsible for the uncontrolled production of extracellular matrix which leads to loss of function and organ failure. Fibrotic diseases include a variety of clinical entities, including organ specific fibrosis (heart, liver, lung, kidney, bone marrow, skin, pancreas), other forms of fibrosis (retroperitoneal, nephrogenic, and cystic), and connective tissue disorders (atherosclerosis, cirrhosis, scleroderma, keloids, Crohn's disease, and endometriosis). In cancer, the tumor stroma microenvironment contains large numbers of myofibroblasts as well as other cells, which are collectively referred to as cancer associated fibroblasts. Cancer associated fibroblasts play a major role in tumor initiation, progression, and metastais through the production of a variety of growth factors, ECM proteins, and other pro-angiogenic and pro-metastatic factors (Khamis Z I, et al., *Active roles of tumor stroma in breast cancer metastasis*, Int J Breast Cancer, 2012, 2012:574025).

Therefore, drugs which inhibit the transition of fibroblasts to myofibroblasts have potential for the treatment of cancer, the prevention and treatment of metastatsis, and the treatment of a variety of fibrotic diseases.

SUMMARY

Provided herein are compounds of formula (I), or an enantiomer, a mixture of enantiomers or a mixture of diastereomers thereof, or a pharmaceutically acceptable salt, solvate, hydrate or prodrug thereof:

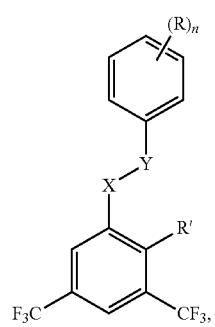

(I)

wherein R, R', X, and Y are defined herein elsewhere. The compounds are useful for the treatment, prevention, and/or amelioration of various disorders, such as cancer and proliferative disorders.

Also provided herein are pharmaceutical compositions and dosage forms comprising a compound provided herein, e.g., a compound of formula (I), or an enantiomer, a mixture of enantiomers or a mixture of diastereomers thereof, or a pharmaceutically acceptable salt, solvate, hydrate or prodrug thereof. In one embodiment, the pharmaceutical compositions and dosage forms further comprise one or more pharmaceutically acceptable carriers or excipients. In one embodiment, the compositions and dosage forms provided herein further comprise one or more additional active agents, such as, e.g., a cancer therapeutic agent.

Also provided herein are methods for the treatment, prevention, and/or amelioration of one or more symptoms of a disorder, such as cancer or a proliferative disorder, in a subject, comprising administering to the subject a therapeutically effective amount of a compound provided herein, e.g., a compound of formula (I), or an enantiomer, a mixture of enantiomers or a mixture of diastereomers thereof, or a pharmaceutically acceptable salt, solvate, hydrate or prodrug thereof. In one embodiment, the subject is a human. Also provided herein are uses of compounds or compositions provided herein in the manufacture of a medicament for the treatment, prevention, and/or amelioration of various disorders provided herein. Also provided herein are compounds and compositions for use in the treatment, prevention, and/or amelioration of various disorders provided herein. Disorders that may be treated, prevented, and/or ameliorated include, but are not limited to, cancer, proliferative disorders, breast cancer (e.g., triple negative breast cancer, ER+ breast cancer, or ER− breast cancer), basal cell nevus syndrome (Gorlin syndrome), basal cell carcinoma, skin cancer, lung cancer, small cell lung cancer, non-small cell lung cancer, brain cancer, medulloblastoma, glioblastoma, colorectal cancer, ovarian cancer, liver cancer, pancreatic cancer (e.g., carcinoma, angiosarcoma, adenosarcoma), gastric cancer, gastroesophageal junction cancer, prostate cancer, cervical cancer, bladder cancer, head and neck cancer, lymphoma (e.g., mantle cell lymphoma, diffuse large B-cell lymphoma), solid tumors that cannot be removed by surgery, locally advanced solid tumors, metastatic solid tumors, leukemia (e.g., acute myeloid leukemia (AML), acute lymphoblastic leukemia (ALL), or chronic myeloid leukemia (CML)), or recurrent or refractory tumors.

In one embodiment, provided herein is a method of inhibiting or reducing the activity of eIF4E. In one embodiment, the method comprises disrupting the eIF4F complex with a compound provided herein, e.g., a compound of formula (I), or an enantiomer, a mixture of enantiomers or a mixture of diastereomers thereof, or a pharmaceutically acceptable salt, solvate, hydrate or prodrug thereof. In one embodiment, the method comprises downregulating protein translation initiation with a compound provided herein, e.g., a compound of formula (I), or an enantiomer, a mixture of enantiomers or a mixture of diastereomers thereof, or a pharmaceutically acceptable salt, solvate, hydrate or prodrug thereof.

DETAILED DESCRIPTION

Figure 1:
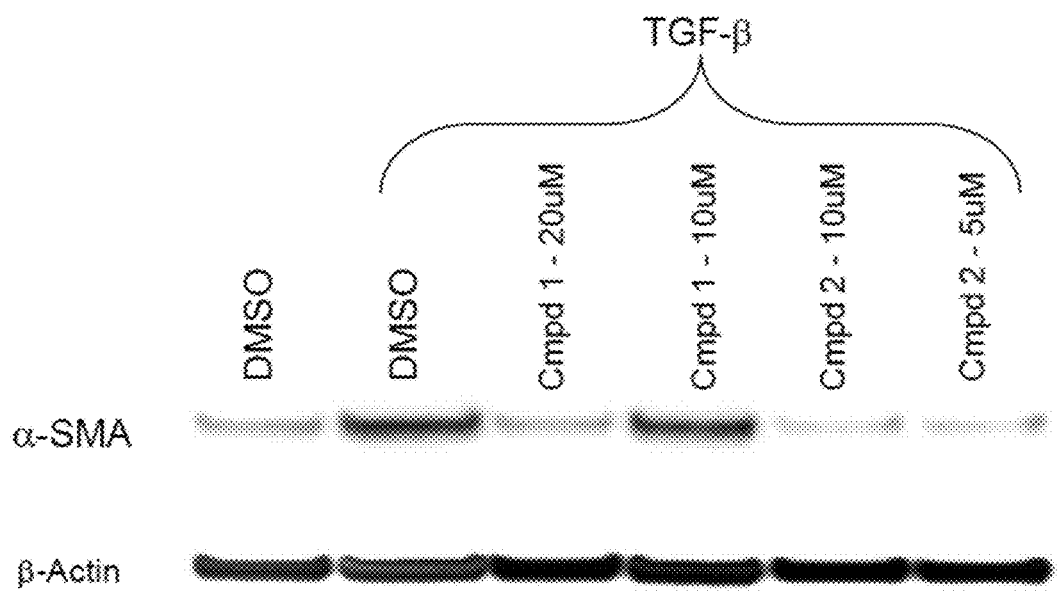
FIG. 1 illustrates the effect of Compound 1 and Compound 2 on inhibiting α-smooth muscle actin in vitro activity in normal human lung fibroblasts (NHLFs).

Unless defined otherwise, all technical and scientific terms used herein have the same meaning as those commonly understood by one of ordinary skill in the art. All publications and patents referred to herein are incorporated by reference herein in their entireties.

A. DEFINITIONS

As used in the specification and the accompanying claims, the indefinite articles "a" and "an" and the definite article "the" include plural as well as singular referents, unless the context clearly dictates otherwise.

As used herein, and unless otherwise indicated, the term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range.

As used herein, and unless otherwise indicated, the term "alkyl" refers to a linear or branched saturated monovalent hydrocarbon radical, wherein the alkyl may optionally be substituted with one or more substituents. The term "alkyl" also encompasses both linear and branched alkyl, unless otherwise specified. In certain embodiments, the alkyl is a linear saturated monovalent hydrocarbon radical that has 1 to 20 ($C_{1-20}$), 1 to 15 ($C_{1-15}$), 1 to 12 ($C_{1-12}$), 1 to 10 ($C_{1-10}$), or 1 to 6 ($C_{1-6}$) carbon atoms, or branched saturated monovalent hydrocarbon radical of 3 to 20 ($C_{3-20}$), 3 to 15 ($C_{3-15}$), 3 to 12 ($C_{3-12}$), 3 to 10 ($C_{3-10}$), or 3 to 6 ($C_{3-6}$) carbon atoms. As used herein, linear $C_{1-6}$ and branched $C_{3-6}$ alkyl groups are also referred as "lower alkyl." Examples of alkyl groups include, but are not limited to, methyl, ethyl, propyl (including all isomeric forms), n-propyl, isopropyl, butyl (including all isomeric forms), n-butyl, isobutyl, t-butyl, pentyl (including all isomeric forms), and hexyl (including all isomeric forms). For example, $C_{1-6}$ alkyl refers to a linear saturated monovalent hydrocarbon radical of 1 to 6 carbon atoms or a branched saturated monovalent hydrocarbon radical of 3 to 6 carbon atoms. In one embodiment, the alkyl has 2 to 20 ($C_{2-20}$), 2 to 15 ($C_{2-15}$), 2 to 12 ($C_{2-12}$), 2 to 10 ($C_{2-10}$), or 2 to 6 ($C_{2-6}$) carbon atoms. In one embodiment, the alkyl has 3 to 20 ($C_{3-20}$), 3 to 15 ($C_{3-15}$), 3 to 12 ($C_{3-12}$), 3 to 10 ($C_{3-10}$), or 3 to 6 ($C_{3-6}$) carbon atoms. In one embodiment, the alkyl has 2 to 6 ($C_{2-6}$), 2 to 5 ($C_{2-5}$), 2 to 4 ($C_{2-4}$), 2 to 3 ($C_{2-3}$), 3 to 6 ($C_{3-6}$), 3 to 5 ($C_{3-5}$), 3 to 4 ($C_{3-4}$), 4 to 6 ($C_{4-6}$), 4 to 5 ($C_{4-5}$), or 5 to 6 ($C_{5-6}$) carbon atoms.

As used herein, and unless otherwise specified, the term "alkenyl" refers to a linear or branched monovalent hydrocarbon radical, which contains one or more, in one embodiment, one to five, carbon-carbon double bonds. The alkenyl may be optionally substituted one or more substituents. The term "alkenyl" also encompasses radicals having "cis" and "trans" configurations, or alternatively, "E" and "Z" configurations, as appreciated by those of ordinary skill in the art. As used herein, the term "alkenyl" encompasses both linear and branched alkenyl, unless otherwise specified. For example, $C_{2-6}$ alkenyl refers to a linear unsaturated monovalent hydrocarbon radical of 2 to 6 carbon atoms or a branched unsaturated monovalent hydrocarbon radical of 3 to 6 carbon atoms. In certain embodiments, the alkenyl is a linear monovalent hydrocarbon radical of 2 to 20 ($C_{2-20}$), 2 to 15 ($C_{2-15}$), 2 to 12 ($C_{2-12}$), 2 to 10 ($C_{2-10}$), or 2 to 6 ($C_{2-6}$) carbon atoms, or a branched monovalent hydrocarbon radical of 3 to 20 ($C_{3-20}$), 3 to 15 ($C_{3-15}$), 3 to 12 ($C_{3-12}$), 3 to 10 ($C_{3-10}$), or 3 to 6 ($C_{3-6}$) carbon atoms. Examples of alkenyl groups include, but are not limited to, ethenyl, propen-1-yl, propen-2-yl, allyl, butenyl, and 4-methylbutenyl.

As used herein, and unless otherwise specified, the term "alkynyl" refers to a linear or branched monovalent hydrocarbon radical, which contains one or more, in one embodiment, one to five, carbon-carbon triple bonds. The alkynyl may be optionally substituted one or more substituents. The term "alkynyl" also encompasses both linear and branched alkynyl, unless otherwise specified. In certain embodiments, the alkynyl is a linear monovalent hydrocarbon radical of 2 to 20 ($C_{2-20}$), 2 to 15 ($C_{2-15}$), 2 to 12 ($C_{2-12}$), 2 to 10 ($C_{2-10}$), or 2 to 6 ($C_{2-6}$) carbon atoms, or a branched monovalent hydrocarbon radical of 3 to 20 ($C_{3-20}$), 3 to 15 ($C_{3-15}$), 3 to 12 ($C_{3-12}$), 3 to 10 ($C_{3-10}$), or 3 to 6 ($C_{3-6}$) carbon atoms. Examples of alkynyl groups include, but are not limited to, ethynyl (—C≡CH) and propargyl (—CH$_2$C≡CH). For example, $C_{2-6}$ alkynyl refers to a linear unsaturated monovalent hydrocarbon radical of 2 to 6 carbon atoms or a branched unsaturated monovalent hydrocarbon radical of 3 to 6 carbon atoms.

As used herein, and unless otherwise specified, the term "cycloalkyl" refers to a cyclic saturated bridged and/or non-bridged monovalent hydrocarbon radical, which may be optionally substituted one or more substituents as described herein. In certain embodiments, the cycloalkyl has from 3 to 20 ($C_{3-20}$), from 3 to 15 ($C_{3-15}$), from 3 to 12 ($C_{3-12}$), from 3 to 10 ($C_{3-10}$), or from 3 to 7 ($C_{3-7}$) carbon atoms. Examples of cycloalkyl groups include, but are not limited to, cyclopropyl, cyclobutyl, cyclopentyl, cyclohexyl, cycloheptyl, decalinyl, and adamantyl.

As used herein, and unless otherwise specified, the term "heteroalkyl" refers to a stable straight or branched chain, or cyclic hydrocarbon radical, or combinations thereof, consisting of the stated number of carbon atoms and from one to three heteroatoms selected from the group consisting of O, N, Si and S, and wherein the nitrogen and sulfur atoms are optionally oxidized and the nitrogen heteroatom can optionally be quaternized. The heteroatom(s) O, N and S may be placed at any interior position of the heteroalkyl group. The heteroatom Si can be placed at any position of the heteroalkyl group, including the position at which the alkyl group is attached to the remainder of the molecule. The heteroatom O, N, or S cannot be placed at the position at which the alkyl group is attached to the remainder of the molecule. The heteroatom O, N, or S can be placed at the external position distal to where the alkyl group is attached to the remainder of the molecule. Examples include —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$—S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, and —CH=CH—N(CH$_3$)—CH$_3$. Up to two heteroatoms can be consecutive, such as, for example, —CH2-NH—OCH$_3$ and —CH$_2$—O—Si(CH$_3$)$_3$. Also included in the term "heteroalkyl" are those radicals described as "heteroalkylene" and "heterocycloalkyl." The term "heteroalkylene" by itself or as part of another substituent means a divalent radical derived from heteroalkyl, as exemplified by —CH$_2$—CH$_2$—S—CH$_2$—CH$_2$— and —CH$_2$—S—CH$_2$—CH$_2$—NH—CH$_2$—. Still further, for heteroalkylene linking groups, as well as all other linking group provided herein, no orientation of the linking group is implied.

As used herein, and unless otherwise specified, the term "aryl" refers to a monocyclic aromatic group and/or multicyclic monovalent aromatic group that contain at least one aromatic hydrocarbon ring. In certain embodiments, the aryl has from 6 to 20 (C$_{6-20}$), from 6 to 15 (C$_{6-15}$), or from 6 to 10 (C$_{6-10}$) ring atoms. Examples of aryl groups include, but are not limited to, phenyl, naphthyl, fluorenyl, azulenyl, anthryl, phenanthryl, pyrenyl, biphenyl, and terphenyl. Aryl also refers to bicyclic or tricyclic carbon rings, where one of the rings is aromatic and the others of which may be saturated, partially unsaturated, or aromatic, for example, dihydronaphthyl, indenyl, indanyl, or tetrahydronaphthyl (tetralinyl). In certain embodiments, aryl may also be optionally substituted with one or more substituents.

As used herein, and unless otherwise specified, the term "arylalkyl" or "aralkyl" refers to a monovalent alkyl group substituted with aryl. In certain embodiments, both alkyl and aryl may be optionally substituted with one or more substituents.

As used herein, and unless otherwise specified, the term "heteroaryl" refers to a monocyclic aromatic group and/or multicyclic aromatic group that contain at least one aromatic ring, wherein at least one ring contains one or more heteroatoms independently selected from O, S, and N. Each ring of a heteroaryl group can contain one or two O atoms, one or two S atoms, and/or one to four N atoms, provided that the total number of heteroatoms in each ring is four or less and each ring contains at least one carbon atom. In certain embodiments, the heteroaryl has from 5 to 20, from 5 to 15, or from 5 to 10 ring atoms. Examples of monocyclic heteroaryl groups include, but are not limited to, furanyl, imidazolyl, isothiazolyl, isoxazolyl, oxadiazolyl, oxazolyl, pyrazinyl, pyrazolyl, pyridazinyl, pyridyl, pyrimidinyl, pyrrolyl, thiadiazolyl, thiazolyl, thienyl, tetrazolyl, triazinyl, and triazolyl. Examples of bicyclic heteroaryl groups include, but are not limited to, benzofuranyl, benzimidazolyl, benzoisoxazolyl, benzopyranyl, benzothiadiazolyl, benzothiazolyl, benzothienyl, benzothiophenyl, benzotriazolyl, benzoxazolyl, furopyridyl, imidazopyridinyl, imidazothiazolyl, indolizinyl, indolyl, indazolyl, isobenzofuranyl, isobenzothienyl, isoindolyl, isoquinolinyl, isothiazolyl, naphthyridinyl, oxazolopyridinyl, phthalazinyl, pteridinyl, purinyl, pyridopyridyl, pyrrolopyridyl, quinolinyl, quinoxalinyl, quinazolinyl, thiadiazolopyrimidyl, and thienopyridyl. Examples of tricyclic heteroaryl groups include, but are not limited to, acridinyl, benzindolyl, carbazolyl, dibenzofuranyl, perimidinyl, phenanthrolinyl, phenanthridinyl, phenarsazinyl, phenazinyl, phenothiazinyl, phenoxazinyl, and xanthenyl. In certain embodiments, heteroaryl may be optionally substituted with one or more substituents.

As used herein, and unless otherwise specified, the term "heterocyclyl," "heterocycloalkyl," or "heterocyclic" refers to a monocyclic non-aromatic ring system and/or multicyclic ring system that contains at least one non-aromatic ring, wherein at least one ring contains one or more heteroatoms independently selected from O, S, or N; and the remaining ring atoms are carbon atoms. In certain embodiments, the heterocyclyl or heterocyclic group has from 3 to 20, from 3 to 15, from 3 to 10, from 3 to 8, from 4 to 7, or from 5 to 6 ring atoms. In certain embodiments, the heterocyclyl is a monocyclic, bicyclic, tricyclic, or tetracyclic ring system, which may include a fused or bridged ring system, and in which the nitrogen or sulfur atoms may be optionally oxidized, the nitrogen atoms may be optionally quaternized, and some rings may be partially or fully saturated, or aromatic. The heterocyclyl may be attached to the main structure at any heteroatom or carbon atom which results in the creation of a stable compound. Examples of such heterocyclic radicals include, but are not limited to, azepinyl, benzodioxanyl, benzodioxolyl, benzofuranonyl, benzopyranonyl, benzopyranyl, benzotetrahydrofuranyl, benzotetrahydrothienyl, benzothiopyranyl, benzoxazinyl, β-carbolinyl, chromanyl, chromonyl, cinnolinyl, coumarinyl, decahydroisoquinolinyl, dihydrobenzisothiazinyl, dihydrobenzisoxazinyl, dihydrofuryl, dihydroisoindolyl, dihydropyranyl, dihydropyrazolyl, dihydropyrazinyl, dihydropyridinyl, dihydropyrimidinyl, dihydropyrrolyl, dioxolanyl, 1,4-dithianyl, furanonyl, imidazolidinyl, imidazolinyl, indolinyl, isobenzotetrahydrofuranyl, isobenzotetrahydrothienyl, isochromanyl, isocoumarinyl, isoindolinyl, isothiazolidinyl, isoxazolidinyl, morpholinyl, octahydroindolyl, octahydroisoindolyl, oxazolidinonyl, oxazolidinyl, oxiranyl, piperazinyl, piperidinyl, 4-piperidonyl, pyrazolidinyl, pyrazolinyl, pyrrolidinyl, pyrrolinyl, quinuclidinyl, tetrahydrofuryl, tetrahydroisoquinolinyl, tetrahydropyranyl, tetrahydrothienyl, thiamorpholinyl, thiazolidinyl, tetrahydroquinolinyl, and 1,3,5-trithianyl. In certain embodiments, heterocyclic may be optionally substituted with one or more substituents.

As used herein, and unless otherwise specified, the term "halogen", "halide" or "halo" refers to fluorine, chlorine, bromine, and/or iodine.

As used herein, and unless otherwise specified, the term "hydrogen" encompasses proton ($^1$H), deuterium ($^2$H), tritium ($^3$H), and/or mixtures thereof.

As used herein, and unless otherwise specified, the term "optionally substituted" is intended to mean that a group, such as an alkyl, alkenyl, alkynyl, cycloalkyl, heteroalkyl, aryl, aralkyl, heteroaryl, or heterocyclyl, may be substituted with one or more substituents independently selected from, e.g., (a) C$_{1-6}$ alkyl, C$_{2-6}$ alkenyl, C$_{2-6}$ alkynyl, C$_{3-7}$ cycloalkyl, C$_{6-14}$ aryl, C$_{7-15}$ aralkyl, heteroaryl, and heterocyclyl, each optionally substituted with one or more, in one embodiment, one, two, three, or four, substituents Q$^1$; and (b) halo, cyano (—CN), nitro (—NO$_2$), —C(O)R$^a$, —C(O)OR$^a$, —C(O)NR$^b$R$^c$, —C(NR$^a$)NR$^b$R$^c$, —OR$^a$, —OC(O)R$^a$, —OC(O)OR$^a$, —OC(O)NR$^b$R$^c$, —OC(=NR$^a$)NR$^b$R$^c$, —OS(O)R$^a$, —OS(O)$_2$R$^a$, —OS(O)NR$^b$R$^c$, —OS(O)$_2$NR$^b$R$^c$, —NR$^b$R$^c$, —NR$^a$C(O)R$^d$, —NR$^a$C(O)OR$^d$, —NR$^a$C(O)NR$^b$R$^c$, —NR$^a$C(=NR$^d$)NR$^b$R$^c$, —NR$^a$S(O)R$^d$, —NR$^a$S(O)$_2$R$^d$, —NR$^a$S(O)NR$^b$R$^c$, —NR$^a$S(O)$_2$NR$^b$R$^c$, —SR$^a$, —S(O)R$^a$, —S(O)$_2$R$^a$, —S(O)NR$^b$R$^c$, and —S(O)$_2$NR$^b$R$^c$, wherein each R$^a$, R$^b$, R$^c$, and R$^d$ is independently (i) hydrogen; (ii) C$_{1-6}$ alkyl, C$_{2-6}$ alkenyl, C$_{2-6}$ alkynyl, $C_{3-7}$ cycloalkyl, $C_{6-14}$ aryl, $C_{7-15}$ aralkyl, heteroaryl, or heterocyclyl, each optionally substituted with one or more, in one embodiment, one, two, three, or four, substituents $Q^1$; or (iii) $R^b$ and $R^c$ together with the N atom to which they are attached form heteroaryl or heterocyclyl, optionally substituted with one or more, in one embodiment, one, two, three, or four, substituents $Q^1$.

In one embodiment, each $Q^1$ is independently selected from the group consisting of (a) cyano, halo, and nitro; and (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl; and (c) $-C(O)R^e$, $-C(O)OR^e$, $-C(O)NR^fR^g$, $-C(NR^e)NR^fR^g$, $-OR^e$, $-OC(O)R^e$, $-OC(O)OR^e$, $-OC(O)NR^fR^g$, $-OC(=NR^e)NR^fR^g$, $-OS(O)R^e$, $-OS(O)_2R^e$, $-OS(O)NR^fR^g$, $-OS(O)_2NR^fR^g$, $-NR^fR^g$, $-NR^eC(O)R^h$, $-NR^eC(O)OR^h$, $-NR^eC(O)NR^fR^g$, $-NR^eC(=NR^h)NR^fR^g$, $-NR^eS(O)R^h$, $-NR^eS(O)_2R^h$, $-NR^eS(O)NR^fR^g$, $-NR^eS(O)_2NR^fR^g$, $-SR^e$, $-S(O)R^e$, $-S(O)_2R^e$, $-S(O)NR^fR^g$, and $-S(O)_2NR^fR^g$; wherein each $R^e$, $R^f$, $R^g$, and $R^h$ is independently (i) hydrogen; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (iii) $R^f$ and $R^g$ together with the N atom to which they are attached form heteroaryl or heterocyclyl.

As used herein, and unless otherwise specified, the term "pharmaceutically acceptable salts" refers to salts prepared from pharmaceutically acceptable non-toxic acids, including inorganic acids and organic acids. Suitable non-toxic acids include inorganic and organic acids such as, but not limited to, acetic, alginic, anthranilic, benzenesulfonic, benzoic, camphorsulfonic, citric, ethenesulfonic, formic, fumaric, furoic, gluconic, glutamic, glucorenic, galacturonic, glycidic, hydrobromic, hydrochloric, isethionic, lactic, maleic, malic, mandelic, methanesulfonic, mucic, nitric, pamoic, pantothenic, phenylacetic, propionic, phosphoric, salicylic, stearic, succinic, sulfanilic, sulfuric, tartaric acid, p-toluenesulfonic and the like. In some embodiments, the salt is formed from hydrochloric, hydrobromic, phosphoric, or sulfuric acid. In one embodiment, the salt is formed from hydrochloride salt.

As used herein, and unless otherwise specified, the term "hydrate" means a compound provided herein or a salt thereof, which further includes a stoichiometric or non-stoichiometric amount of water bound by non-covalent intermolecular forces.

As used herein, and unless otherwise specified, the term "solvate" refers to a compound provided herein or a salt thereof, which further includes a stoichiometric or non-stoichiometric amount of solvent bound by non-covalent intermolecular forces. Where the solvent is water, the solvate is a hydrate (e.g., mono-hydrate, dihydrate, trihydrate, tetrahydrate and the like).

As used herein, and unless otherwise specified, the term "stereoisomer" encompasses all enantiomerically/stereomerically pure and enantiomerically/stereomerically enriched compounds provided herein.

As used herein and unless otherwise specified, the term "stereomerically pure" means a composition that comprises one stereoisomer of a compound and is substantially free of other stereoisomers of that compound. For example, a stereomerically pure composition of a compound having one chiral center will be substantially free of the opposite enantiomer of the compound. A stereomerically pure composition of a compound having two chiral centers will be substantially free of other diastereomers of the compound. A typical stereomerically pure compound comprises greater than about 80% by weight of one stereoisomer of the compound and less than about 20% by weight of other stereoisomers of the compound, greater than about 90% by weight of one stereoisomer of the compound and less than about 10% by weight of the other stereoisomers of the compound, greater than about 95% by weight of one stereoisomer of the compound and less than about 5% by weight of the other stereoisomers of the compound, greater than about 97% by weight of one stereoisomer of the compound and less than about 3% by weight of the other stereoisomers of the compound, or greater than about 99% by weight of one stereoisomer of the compound and less than about 1% by weight of the other stereoisomers of the compound.

As used herein and unless otherwise indicated, the term "stereomerically enriched" means a composition that comprises greater than about 55% by weight of one stereoisomer of a compound, greater than about 60% by weight of one stereoisomer of a compound, greater than about 70% by weight, or greater than about 80% by weight of one stereoisomer of a compound.

As used herein, and unless otherwise indicated, the term "enantiomerically pure" means a stereomerically pure composition of a compound having one chiral center. Similarly, the term "enantiomerically enriched" means a stereomerically enriched composition of a compound having one chiral center.

In certain embodiments, as used herein, and unless otherwise specified, "optically active" and "enantiomerically active" refer to a collection of molecules, which has an enantiomeric excess of no less than about 50%, no less than about 70%, no less than about 80%, no less than about 90%, no less than about 91%, no less than about 92%, no less than about 93%, no less than about 94%, no less than about 95%, no less than about 96%, no less than about 97%, no less than about 98%, no less than about 99%, no less than about 99.5%, or no less than about 99.8%. In certain embodiments, the compound comprises about 95% or more of the desired enantiomer and about 5% or less of the less preferred enantiomer based on the total weight of the racemate in question.

In describing an optically active compound, the prefixes R and S are used to denote the absolute configuration of the molecule about its chiral center(s). The (+) and (−) are used to denote the optical rotation of the compound, that is, the direction in which a plane of polarized light is rotated by the optically active compound. The (−) prefix indicates that the compound is levorotatory, that is, the compound rotates the plane of polarized light to the left or counterclockwise. The (+) prefix indicates that the compound is dextrorotatory, that is, the compound rotates the plane of polarized light to the right or clockwise. However, the sign of optical rotation, (+) or (−), is not related to the absolute configuration of the molecule, R or S.

As used herein, and unless otherwise specified, the terms "composition," "formulation," and "dosage form" are intended to encompass products comprising the specified ingredient(s) (in the specified amounts, if indicated), as well as any product(s) which result, directly or indirectly, from combination of the specified ingredient(s) in the specified amount(s).

As used herein, and unless otherwise specified, the term "pharmaceutically acceptable carrier," "pharmaceutically acceptable excipient," "physiologically acceptable carrier," or "physiologically acceptable excipient" refers to a pharmaceutically-acceptable material, composition, or vehicle, such as a liquid or solid filler, diluent, excipient, solvent, or encapsulating material. In one embodiment, each component is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. In one embodiment, by "pharmaceutical" or "pharmaceutically acceptable" it is meant that any diluent(s), excipient(s) or carrier(s) in the composition, formulation, or dosage form are compatible with the other ingredient(s) and not deleterious to the recipient thereof. See, e.g., Remington: *The Science and Practice of Pharmacy,* 21st Edition, Lippincott Williams & Wilkins: Philadelphia, Pa., 2005; *Handbook of Pharmaceutical Excipients,* 5th Edition, Rowe et al., Eds., The Pharmaceutical Press and the American Pharmaceutical Association: 2005; and *Handbook of Pharmaceutical Additives,* 3rd Edition, Ash and Ash Eds., Gower Publishing Company: 2007; *Pharmaceutical Preformulation and Formulation,* 2nd Edition, Gibson Ed., CRC Press LLC: Boca Raton, Fla., 2009.

As used herein, and unless otherwise specified, the terms "active ingredient" and "active substance" refer to a compound, which is administered, alone or in combination with one or more pharmaceutically acceptable excipients, to a subject for treating, preventing, managing, or ameliorating one or more symptoms of a condition, disorder, or disease. As used herein, "active ingredient" and "active substance" may be an optically active isomer of a compound described herein.

As used herein, and unless otherwise specified, the terms "drug," "therapeutic agent," and "chemotherapeutic agent" refer to a compound, or a pharmaceutical composition thereof, which is administered to a subject for treating, preventing, managing, or ameliorating one or more symptoms of a condition, disorder, or disease.

As used herein, and unless otherwise indicated, the terms "treat," "treating" and "treatment" refer to the eradication or amelioration of a disease or disorder, or of one or more symptoms associated with the disease or disorder. In certain embodiments, the terms refer to minimizing the spread or worsening of the disease or disorder resulting from the administration of one or more prophylactic or therapeutic agents to a subject with such a disease or disorder. In some embodiments, the terms refer to the administration of a compound or dosage form provided herein, with or without one or more additional active agent(s), after the diagnosis or onset of symptoms of the particular disease.

As used herein, and unless otherwise indicated, the terms "prevent," "preventing" and "prevention" refer to the prevention of the onset, recurrence or spread of a disease or disorder, or of one or more symptoms thereof. In certain embodiments, the terms refer to the treatment with or administration of a compound or dosage form provided herein, with or without one or more other additional active agent(s), prior to the onset of symptoms, particularly to patients at risk of disease or disorders provided herein. The terms encompass the inhibition or reduction of a symptom of the particular disease. In certain embodiments, subjects with familial history of a disease are potential candidates for preventive regimens. In certain embodiments, subjects who have a history of recurring symptoms are also potential candidates for the prevention. In this regard, the term "prevention" may be interchangeably used with the term "prophylactic treatment."

As used herein, and unless otherwise specified, the terms "manage," "managing" and "management" refer to preventing or slowing the progression, spread or worsening of a disease or disorder, or of one or more symptoms thereof. Often, the beneficial effects that a subject derives from a prophylactic and/or therapeutic agent do not result in a cure of the disease or disorder. In this regard, the term "managing" encompasses treating a patient who had suffered from the particular disease in an attempt to prevent or minimize the recurrence of the disease.

As used herein, and unless otherwise specified, "amelioration" of the symptoms of a particular disorder by administration of a particular pharmaceutical composition refers to any lessening, whether permanent or temporary, lasting or transient, that can be attributed to or associated with the administration of the composition.

As used herein, and unless otherwise specified, the term "therapeutically effective amount" or "effective amount" of a compound means an amount sufficient to provide a therapeutic benefit in the treatment or management of a disease or disorder, or to delay or minimize one or more symptoms associated with the disease or disorder. A "therapeutically effective amount" or "effective amount" of a compound means an amount of therapeutic agent, alone or in combination with one or more other therapies, which provides a therapeutic benefit in the treatment or management of the disease or disorder. The term "therapeutically effective amount" and "effective amount" can encompass an amount that improves overall therapy, reduces, delays, or avoids symptoms or causes of disease or disorder, or enhances the therapeutic efficacy of another therapeutic agent.

As used herein, and unless otherwise specified, a "prophylactically effective amount" of a compound is an amount sufficient to prevent a disease or disorder, or prevent its recurrence. A prophylactically effective amount of a compound means an amount of therapeutic agent, alone or in combination with one or more other therapies, which provides a prophylactic benefit in the prevention of the disease. The term "prophylactically effective amount" can encompass an amount that improves overall prophylaxis or enhances the prophylactic efficacy of another prophylactic agent.

As used herein, and unless otherwise specified, the term "subject" is defined herein to include animals such as mammals, including, but not limited to, primates (e.g., humans), cows, sheep, goats, horses, dogs, cats, rabbits, rats, mice and the like. In specific embodiments, the subject is a human. The terms "subject" and "patient" are used interchangeably herein in reference, for example, to a mammalian subject, such as a human.

As used herein, and unless otherwise specified, "tumor" refers to all neoplastic cell growth and proliferation, whether malignant or benign, and all pre-cancerous and cancerous cells and tissues. As used herein, and unless otherwise specified, "neoplastic" refers to any form of dysregulated or unregulated cell growth, whether malignant or benign, resulting in abnormal tissue growth. Thus, "neoplastic cells" include malignant and benign cells having dysregulated or unregulated cell growth.

As used herein, and unless otherwise specified, the terms "cancer" and "cancerous" refer to or describe the physiological condition in mammals that is typically characterized by unregulated cell growth. Examples of cancer include, but are not limited to, lymphoma, leukemia, and solid tumors, such as, for example, lung cancer.

As used herein, and unless otherwise specified, the term "proliferative" disorder or disease refers to unwanted cell proliferation of one or more subset of cells in a multicellular organism resulting in harm (i.e., discomfort or decreased life expectancy) to the multicellular organism. For example, as used herein, proliferative disorder or disease includes neoplastic disorders and other proliferative disorders.

As used herein, and unless otherwise specified, the term "triple negative breast cancer" refers to specific subtypes of breast cancer that are negative clinically for the expression of estrogen receptor (ER), progesterone receptor (PR) and human epidermal growth factor receptor 2 (HER2) protein. These subtypes of breast cancer are generally diagnosed based upon the presence or the lack of three receptors known to fuel most breast cancers: estrogen receptors, progesterone receptors and human epidermal growth factor receptor 2. None of these receptors are found in patients diagnosed with triple negative breast cancer. In other words, a triple negative breast cancer diagnosis means that the offending tumor is estrogen receptor-negative, progesterone receptor-negative and HER2-negative.

As used herein, and unless otherwise specified, the term "relapsed" refers to a situation where a subject, that has had a remission of cancer after a therapy, has a return of cancer cells.

As used herein, and unless otherwise specified, the term "refractory" or "resistant" refers to a circumstance where a subject, even after intensive treatment, has residual cancer cells in the body.

As used herein, and unless otherwise specified, the term "drug resistance" refers to the condition when a disease does not respond to the treatment of a drug or drugs. Drug resistance can be either intrinsic, which means the disease has never been responsive to the drug or drugs, or it can be acquired, which means the disease ceases responding to a drug or drugs that the disease had previously responded to. In certain embodiments, drug resistance is intrinsic. In certain embodiments, the drug resistance is acquired.

As used herein, and unless otherwise specified, the term "anticancer agent" or "cancer therapeutic agent" is meant to include anti-proliferative agents and chemotherapeutic agents, including, but not limited to, antimetabolites (e.g., 5-fluoro uracil, methotrexate, fludarabine, cytarabine (also known as cytosine arabinoside or Ara-C), and high dose cytarabine), antimicrotubule agents (e.g., vinca alkaloids, such as vincristine and vinblastine; and taxanes, such as paclitaxel and docetaxel), alkylating agents (e.g., mechlorethamine, chlorambucil, cyclophosphamide, melphalan, melphalan, ifosfamide, carmustine, azacitidine, decitabine, busulfan, cyclophosphamide, dacarbazine, ifosfamide, and nitrosoureas, such as carmustine, lomustine, bischloroethylnitrosurea, and hydroxyurea), platinum agents (e.g., cisplatin, carboplatin, oxaliplatin, satraplatin (JM-216), and CI-973), anthracyclines (e.g., doxorubicin and daunorubicin), antitumor antibiotics (e.g., mitomycin, bleomycin, idarubicin, adriamycin, daunomycin (also known as daunorubicin, rubidomycin, or cerubidine), and mitoxantrone), topoisomerase inhibitors (e.g., etoposide and camptothecins), purine antagonists or pyrimidine antagonists (e.g., 6-mercaptopurine, 5-fluorouracil, cytarabine, clofarabine, and gemcitabine), cell maturing agents (e.g., arsenic trioxide and tretinoin), DNA repair enzyme inhibitors (e.g., podophyllotoxines, etoposide, irinotecan, topotecan, and teniposide), enzymes that prevent cell survival (e.g., asparaginase and pegaspargase), histone deacetylase inhibitors (e.g., vorinostat), any other cytotoxic agents (e.g., estramustine phosphate, dexamethasone, prednimustine, and procarbazine), hormones (e.g., dexamethasone, prednisone, methylprednisolone, tamoxifen, leuprolide, flutamide, and megestrol), monoclonal antibodies (e.g., gemtuzumab ozogamicin, alemtuzumab, rituximab, and yttrium-90-ibritumomab tiuxetan), immuno-modulators (e.g., thalidomide and lenalidomide), Bcr-Abl kinase inhibitors (e.g., AP23464, AZD0530, CGP76030, PD180970, SKI-606, imatinib, BMS354825 (dasatinib), AMN107 (nilotinib), and VX-680), hormone agonists or antagonists, partial agonists or partial antagonists, kinase inhibitors, surgery, radiotherapy (e.g., gamma-radiation, neutron bean radiotherapy, electron beam radiotherapy, proton therapy, brachytherapy, and systemic radioactive isotopes), endocrine therapy, biological response modifiers (e.g., interferons, interleukins, and tumor necrosis factor), hyperthermia and cryotherapy, and agents to attenuate any adverse effects (e.g., antiemetics). In one embodiment, the anticancer agent or cancer therapeutic agent is a cytotoxic agent, an antimetabolite, an antifolate, an HDAC inhibitor such as MGCD0103 (a.k.a. N-(2-aminophenyl)-4-((4-(pyridin-3-yl)pyrimidin-2-ylamino)methyl)benzamide), a DNA intercalating agent, a DNA cross-linking agent, a DNA alkylating agent, a DNA cleaving agent, a topoisomerase inhibitor, a CDK inhibitor, a JAK inhibitor, an anti-angiogenic agent, a Bcr-Abl inhibitor, an HER2 inhibitor, an EGFR inhibitor, a VEGFR inhibitor, a PDGFR inhibitor, an HGFR inhibitor, an IGFR inhibitor, a c-Kit inhibitor, a Ras pathway inhibitor, a PI3K inhibitor, a multi-targeted kinase inhibitor, an mTOR inhibitor, an anti-estrogen, an anti-androgen, an aromatase inhibitor, a somatostatin analog, an ER modulator, an anti-tubulin agent, a vinca alkaloid, a taxane, an HSP inhibitor, a Smoothened antagonist, a telomerase inhibitor, a COX-2 inhibitor, an anti-metastatic agent, an immunosuppressant, a biologics such as antibodies and hormonal therapies.

As used herein, and unless otherwise specified, the terms "co-administration" and "in combination with" include the administration of two or more therapeutic agents simultaneously, concurrently or sequentially within no specific time limits unless otherwise indicated. In one embodiment, the agents are present in the cell or in the subject's body at the same time or exert their biological or therapeutic effect at the same time. In one embodiment, the therapeutic agents are in the same composition or unit dosage form. In other embodiments, the therapeutic agents are in separate compositions or unit dosage forms. In certain embodiments, a first agent can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), essentially concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapeutic agent.

B. COMPOUNDS

In one embodiment, provided herein is a compound of formula (I):

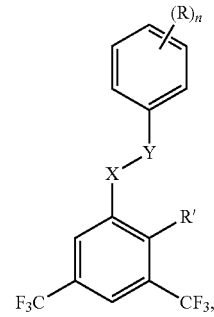

(I)

or an enantiomer, a mixture of enantiomers, or a mixture of two or more diastereomers thereof;

or a pharmaceutically acceptable salt, solvate, hydrate, or prodrug thereof; wherein:

X is NH, and Y is S(O)$_2$; or X is S(O)$_2$, and Y is NH;

R' is hydrogen, halogen, cyano, OH, OC(O)R$_a$, C(O)R$_a$, C(O)OR$_a$, C(O)NR$_a$R$_b$, NR$_a$C(O)R$_b$, NR$_a$R$_b$, OS(O)R$_a$, SR$_a$, S(O)R$_a$, S(O)$_2$R$_a$, S(O)$_2$NR$_a$R$_b$, NR$_a$S(O)$_2$R$_b$, (C$_1$-C$_8$)alkyl, (C$_2$-C$_8$)alkenyl, (C$_2$-C$_8$)alkynyl, (C$_1$-C$_8$)alkoxy, (C$_2$-C$_8$)alkenyloxy, (C$_2$-C$_8$)alkynyloxy, (C$_3$-C$_8$)cycloalkyl, or (C$_3$-C$_8$)cycloalkyloxy, wherein the alkyl, alkenyl, alkynyl, alkoxy, alkenyloxy, alkynyloxy, cycloalkyl, and cycloalkyloxy are each optionally substituted with one or more halogen;

n is 2, 3, or 4;

each occurrence of R is independently hydrogen, (C$_1$-C$_6$)alkyl, (C$_2$-C$_8$)alkenyl, (C$_2$-C$_8$)alkynyl, or (C$_3$-C$_8$)cycloalkyl, each of which is optionally substituted with one or more halogen; and R$_a$ and R$_b$ are each independently hydrogen, (C$_1$-C$_8$)alkyl, (C$_2$-C$_8$)alkenyl, (C$_2$-C$_8$)alkynyl, (C$_1$-C$_8$)heteroalkyl, (C$_3$-C$_8$)cycloalkyl, (C$_7$-C$_{12}$)aralkyl, phenyl, (5 to 6 membered)heteroaryl, or (3 to 7 membered)heterocyclyl; or R$_a$ and R$_b$ together form a 3 to 10 membered ring. In one embodiment of a compound of formula (I), X is NH, and Y is S(O)$_2$. In another embodiment of a compound of formula (I), X is S(O)$_2$, and Y is NH. In one embodiment of a compound of formula (I), R' is hydrogen, halogen, cyano, (C$_1$-C$_8$)alkyl, (C$_2$-C$_8$)alkenyl, (C$_2$-C$_8$)alkynyl, (C$_1$-C$_8$)alkoxy, (C$_2$-C$_8$)alkenyloxy, (C$_2$-C$_8$)alkynyloxy, (C$_3$-C$_8$)cycloalkyl or (C$_3$-C$_8$)cycloalkyloxy, wherein the alkyl, alkenyl, alkynyl, alkoxy, alkenyloxy, alkynyloxy, cycloalkyl, and cycloalkyloxy are each optionally substituted with one or more halogen. In one embodiment of a compound of formula (I), R' is hydrogen, halogen, (C$_1$-C$_8$)alkyl, or (C$_1$-C$_8$)alkoxy, wherein the alkyl and alkoxyl are each optionally substituted with one or more halogen. In one embodiment of a compound of formula (I), R' is hydrogen, halogen, (C$_1$-C$_4$)alkyl, or (C$_1$-C$_4$)alkoxy, wherein the alkyl and alkoxyl are each optionally substituted with one or more halogen. In one embodiment of a compound of formula (I), R' is hydrogen, F, Cl, Br, (C$_1$-C$_4$)alkyl, CF$_3$, or OCF$_3$. In one embodiment of a compound of formula (I), R' is hydrogen or (C$_1$-C$_4$)alkyl. In one embodiment of a compound of formula (I), R' is hydrogen or methyl. In one embodiment of a compound of formula (I), R' is hydrogen. In another embodiment of a compound of formula (I), R' is methyl. In yet another embodiment of a compound of formula (I), R' is Cl. In one embodiment of a compound of formula (I), R' is Br.

In one embodiment of a compound of formula (I), n is 2. In another embodiment of a compound of formula (I), n is 3. In yet another embodiment of a compound of formula (I), n is 4. In yet another embodiment of a compound of formula (I), n is 2 or 3. In yet another embodiment of a compound of formula (I), n is 3 or 4.

In one embodiment of a compound of formula (I), each occurrence of R is independently hydrogen, (C$_1$-C$_6$)alkyl, (C$_2$-C$_8$)alkenyl, (C$_2$-C$_8$)alkynyl, or (C$_3$-C$_8$)cycloalkyl. In one embodiment of a compound of formula (I), each occurrence of R is independently (C$_1$-C$_4$)alkyl. In one embodiment of a compound of formula (I), each occurrence of R is independently methyl, ethyl, isopropyl, or tert-butyl. In one embodiment of a compound of formula (I), each occurrence of R is independently isopropyl.

In one embodiment, provided herein is a compound of formula (I):

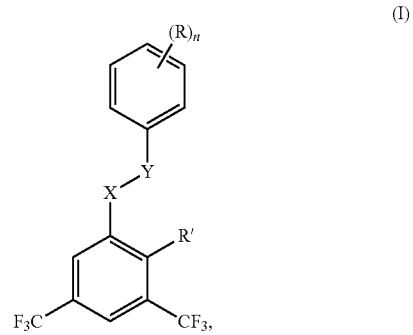

or an enantiomer, a mixture of enantiomers, or a mixture of two or more diastereomers thereof;
or a pharmaceutically acceptable salt, solvate, hydrate, or prodrug thereof; wherein X is NH, and Y is S(O)$_2$; or X is S(O)$_2$, and Y is NH;

R' is hydrogen, halogen, cyano, OH, OC(O)R$_a$, C(O)R$_a$, C(O)OR$_a$, C(O)NR$_a$R$_b$, NR$_a$C(O)R$_b$, NR$_a$R$_b$, OS(O)R$_a$, SR$_a$, S(O)R$_a$, S(O)$_2$R$_a$, S(O)$_2$NR$_a$R$_b$, NR$_a$S(O)$_2$R$_b$, (C$_1$-C$_8$)alkyl, (C$_2$-C$_8$)alkenyl, (C$_2$-C$_8$)alkynyl, (C$_1$-C$_8$)alkoxy, (C$_2$-C$_8$)alkenyloxy, (C$_2$-C$_8$)alkynyloxy, (C$_3$-C$_8$)cycloalkyl, or (C$_3$-C$_8$)cycloalkyloxy, wherein the alkyl, alkenyl, alkynyl, alkoxy, alkenyloxy, alkynyloxy, cycloalkyl, and cycloalkyloxy are each optionally substituted with one or more halogen;

n is 2, 3, or 4;

each occurrence of R is independently, (C$_2$-C$_6$)alkyl, (C$_2$-C$_8$)alkenyl, (C$_2$-C$_8$)alkynyl, or (C$_3$-C$_8$)cycloalkyl, each of which is optionally substituted with one or more halogen; and R$_a$ and R$_b$ are each independently hydrogen, (C$_1$-C$_8$)alkyl, (C$_2$-C$_8$)alkenyl, (C$_2$-C$_8$)alkynyl, (C$_1$-C$_8$)heteroalkyl, (C$_3$-C$_8$)cycloalkyl, (C$_7$-C$_{12}$)aralkyl, phenyl, (5 to 6 membered)heteroaryl, or (3 to 7 membered)heterocyclyl; or Ra and Rb together form a 3 to 10 membered ring.

In one embodiment of a compound of formula (I), X is NH, and Y is S(O)2. In another embodiment of a compound of formula (I), X is S(O)2, and Y is NH.

In one embodiment of a compound of formula (I), R' is hydrogen, halogen, cyano, (C1-C8)alkyl, (C2-C$_8$)alkenyl, (C$_2$-C$_8$)alkynyl, (C$_1$-C$_8$)alkoxy, (C$_2$-C$_8$)alkenyloxy, (C$_2$-C$_8$)alkynyloxy, (C$_3$-C$_8$)cycloalkyl or (C$_3$-C$_8$)cycloalkyloxy, wherein the alkyl, alkenyl, alkynyl, alkoxy, alkenyloxy, alkynyloxy, cycloalkyl, and cycloalkyloxy are each optionally substituted with one or more halogen. In one embodiment of a compound of formula (I), R' is hydrogen, halogen, (C$_1$-C$_8$)alkyl, or (C$_1$-C$_8$)alkoxy, wherein the alkyl and alkoxyl are each optionally substituted with one or more halogen. In one embodiment of a compound of formula (I), R' is hydrogen, halogen, (C$_1$-C$_4$)alkyl, or (C$_1$-C$_4$)alkoxy, wherein the alkyl and alkoxyl are each optionally substituted with one or more halogen. In one embodiment of a compound of formula (I), R' is hydrogen, F, Cl, Br, (C$_1$-C$_4$)alkyl, CF$_3$, or OCF$_3$. In one embodiment of a compound of formula (I), R' is hydrogen or (C$_1$-C$_4$)alkyl. In one embodiment of a compound of formula (I), R' is hydrogen or methyl. In one embodiment of a compound of formula (I), R' is hydrogen. In another embodiment of a compound of formula (I), R' is methyl. In another embodiment of a compound of formula (I), R' is Cl.

In one embodiment of a compound of formula (I), n is 2. In another embodiment of a compound of formula (I), n is 3. In yet another embodiment of a compound of formula (I), n is 4. In yet another embodiment of a compound of formula (I), n is 2 or 3. In yet another embodiment of a compound of formula (I), n is 3 or 4.

In one embodiment of a compound of formula (I), each occurrence of R is independently, $(C_2-C_6)$alkyl, $(C_2-C_8)$alkenyl, $(C_2-C_8)$alkynyl, or $(C_3-C_8)$cycloalkyl. In one embodiment of a compound of formula (I), each occurrence of R is independently $(C_2-C_4)$alkyl. In one embodiment of a compound of formula (I), each occurrence of R is independently ethyl, or isopropyl. In one embodiment of a compound of formula (I), each occurrence of R is independently isopropyl.

In one embodiment, provided herein is a compound of formula (II):

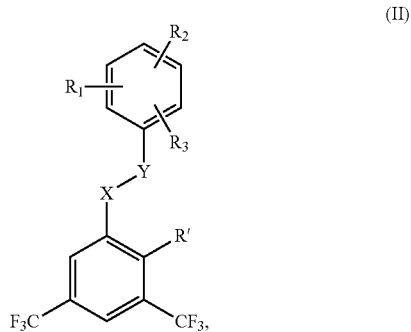

or an enantiomer, a mixture of enantiomers, or a mixture of two or more diastereomers thereof;
or a pharmaceutically acceptable salt, solvate, hydrate, or prodrug thereof; wherein:
  X is NH, and Y is $S(O)_2$; or X is $S(O)_2$, and Y is NH;
  R' is hydrogen, halogen, cyano, OH, $OC(O)R_a$, $C(O)R_a$, $C(O)OR_a$, $C(O)NR_aR_b$, $NR_aC(O)R_b$, $NR_aR_b$, $OS(O)R_a$, $SR_a$, $S(O)R_a$, $S(O)_2R_a$, $S(O)_2NR_aR_b$, $NR_aS(O)_2R_b$, $(C_1-C_8)$alkyl, $(C_2-C_8)$alkenyl, $(C_2-C_8)$alkynyl, $(C_1-C_8)$alkoxy, $(C_2-C_8)$alkenyloxy, $(C_2-C_8)$alkynyloxy, $(C_3-C_8)$cycloalkyl, or $(C_3-C_8)$cycloalkyloxy, wherein the alkyl, alkenyl, alkynyl, alkoxy, alkenyloxy, alkynyloxy, cycloalkyl, and cycloalkyloxy are each optionally substituted with one or more halogen;
  $R_1$ is independently $(C_1-C_6)$alkyl, $(C_2-C_8)$alkenyl, $(C_2-C_8)$alkynyl, or $(C_3-C_8)$cycloalkyl, each of which is optionally substituted with one or more halogen;
  $R_2$ is independently hydrogen, $(C_1-C_6)$alkyl, $(C_2-C_8)$alkenyl, $(C_2-C_8)$alkynyl, or $(C_3-C_8)$cycloalkyl, each of which is optionally substituted with one or more halogen; and
  $R_3$ is independently $(C_1-C_6)$alkyl, $(C_2-C_8)$alkenyl, $(C_2-C_8)$alkynyl, or $(C_3-C_8)$cycloalkyl, each of which is optionally substituted with one or more halogen; and
  $R_a$ and $R_b$ are each independently hydrogen, $(C_1-C_8)$alkyl, $(C_2-C_8)$alkenyl, $(C_2-C_8)$alkynyl, $(C_1-C_8)$heteroalkyl, $(C_3-C_8)$cycloalkyl, $(C_7-C_{12})$aralkyl, phenyl, (5 to 6 membered) heteroaryl, or (3 to 7 membered)heterocyclyl; or $R_a$ and $R_b$ together form a 3 to 10 membered ring.

In one embodiment of a compound of formula (II), X is NH, and Y is $S(O)_2$. In another embodiment of a compound of formula (II), X is $S(O)_2$, and Y is NH.

In one embodiment of a compound of formula (II), R' is hydrogen, halogen, cyano, $(C_1-C_8)$alkyl, $(C_2-C_8)$alkenyl, $(C_2-C_8)$alkynyl, $(C_1-C_8)$alkoxy, $(C_2-C_8)$alkenyloxy, $(C_2-C_8)$alkynyloxy, $(C_3-C_8)$cycloalkyl or $(C_3-C_8)$cycloalkyloxy, wherein the alkyl, alkenyl, alkynyl, alkoxy, alkenyloxy, alkynyloxy, cycloalkyl, and cycloalkyloxy are each optionally substituted with one or more halogen. In one embodiment of a compound of formula (II), R' is hydrogen, halogen, $(C_1-C_8)$alkyl, or $(C_1-C_8)$alkoxy, wherein the alkyl and alkoxyl are each optionally substituted with one or more halogen. In one embodiment of a compound of formula (II), R' is hydrogen, halogen, $(C_1-C_4)$alkyl, or $(C_1-C_4)$alkoxy, wherein the alkyl and alkoxyl are each optionally substituted with one or more halogen. In one embodiment of a compound of formula (II), R' is hydrogen, F, Cl, Br, $(C_1-C_4)$alkyl, $CF_3$, or $OCF_3$. In one embodiment of a compound of formula (II), R' is hydrogen or $(C_1-C_4)$alkyl. In one embodiment of a compound of formula (II), R' is hydrogen or methyl. In one embodiment of a compound of formula (II), R' is hydrogen. In another embodiment of a compound of formula (II), R' is methyl. In another embodiment of a compound of formula (II), R' is Cl. In one embodiment of a compound of formula (I), R' is Br.

In one embodiment of a compound of formula (II), $R_1$ is $(C_1-C_4)$alkyl. In one embodiment of a compound of formula (II), $R_1$ is methyl, ethyl, or isopropyl. In one embodiment of a compound of formula (II), $R_2$ is hydrogen, or $(C_1-C_4)$alkyl. In one embodiment of a compound of formula (II), $R_2$ is methyl, isopropyl, or tert-butyl. In one embodiment of a compound of formula (II), $R_3$ is $(C_1-C_4)$alkyl. In one embodiment of a compound of formula (II), $R_3$ is methyl, ethyl or isopropyl.

In one embodiment, provided herein is a compound of formula (II):

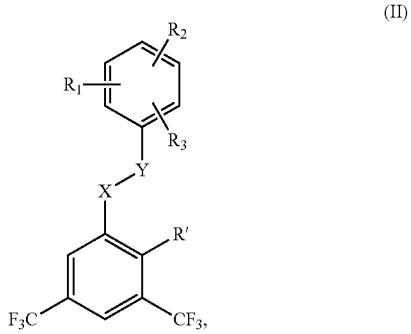

or an enantiomer, a mixture of enantiomers, or a mixture of two or more diastereomers thereof;
or a pharmaceutically acceptable salt, solvate, hydrate, or prodrug thereof; wherein:
  X is NH, and Y is $S(O)_2$; or X is $S(O)_2$, and Y is NH;
  R' is hydrogen, halogen, cyano, OH, $OC(O)R_a$, $C(O)R_a$, $C(O)OR_a$, $C(O)NR_aR_b$, $NR_aC(O)R_b$, $NR_aR_b$, $OS(O)R_a$, $SR_a$, $S(O)R_a$, $S(O)_2R_a$, $S(O)_2NR_aR_b$, $NR_aS(O)_2R_b$, $(C_1-C_8)$alkyl, $(C_2-C_8)$alkenyl, $(C_2-C_8)$alkynyl, $(C_1-C_8)$alkoxy, $(C_2-C_8)$alkenyloxy, $(C_2-C_8)$alkynyloxy, $(C_3-C_8)$cycloalkyl, or $(C_3-C_8)$cycloalkyloxy, wherein the alkyl, alkenyl, alkynyl, alkoxy, alkenyloxy, alkynyloxy, cycloalkyl, and cycloalkyloxy are each optionally substituted with one or more halogen;
  $R_1$, $R_2$, and $R_3$ are independently $(C_2-C_6)$alkyl, $(C_2-C_8)$alkenyl, $(C_2-C_8)$alkynyl, or $(C_3-C_8)$cycloalkyl, each of which is optionally substituted with one or more halogen; and $R_a$ and $R_b$ are each independently hydrogen, $(C_1-C_8)$alkyl, $(C_2-C_8)$alkenyl, $(C_2-C_8)$alkynyl, $(C_1-C_8)$heteroalkyl, $(C_3-C_8)$cycloalkyl, $(C_7-C_{12})$aralkyl, phenyl, (5 to 6 membered) heteroaryl, or (3 to 7 membered)heterocyclyl; or $R_a$ and $R_b$ together form a 3 to 10 membered ring.

In one embodiment of a compound of formula (II), X is NH, and Y is $S(O)_2$. In another embodiment of a compound of formula (II), X is $S(O)_2$, and Y is NH.

In one embodiment of a compound of formula (II), R' is hydrogen, halogen, cyano, $(C_1-C_8)$alkyl, $(C_2-C_8)$alkenyl, $(C_2-C_8)$alkynyl, $(C_1-C_8)$alkoxy, $(C_2-C_8)$alkenyloxy, $(C_2-C_8)$alkynyloxy, $(C_3-C_8)$cycloalkyl or $(C_3-C_8)$cycloalkyloxy, wherein the alkyl, alkenyl, alkynyl, alkoxy, alkenyloxy, alkynyloxy, cycloalkyl, and cycloalkyloxy are each optionally substituted with one or more halogen. In one embodiment of a compound of formula (II), R' is hydrogen, halogen, $(C_1-C_8)$alkyl, or $(C_1-C_8)$alkoxy, wherein the alkyl and alkoxyl are each optionally substituted with one or more halogen. In one embodiment of a compound of formula (II), R' is hydrogen, halogen, $(C_1-C_4)$alkyl, or $(C_1-C_4)$alkoxy, wherein the alkyl and alkoxyl are each optionally substituted with one or more halogen. In one embodiment of a compound of formula (II), R' is hydrogen, F, Cl, Br, $(C_1-C_4)$alkyl, $CF_3$, or $OCF_3$. In one embodiment of a compound of formula (II), R' is hydrogen or $(C_1-C_4)$alkyl. In one embodiment of a compound of formula (II), R' is hydrogen or methyl. In one embodiment of a compound of formula (II), R' is hydrogen. In another embodiment of a compound of formula (II), R' is methyl. In another embodiment of a compound of formula (II), R' is Cl.

In one embodiment of a compound of formula (II), $R_1$, $R_2$, and $R_3$ are independently $(C_2-C_6)$alkyl, $(C_2-C_8)$alkenyl, $(C_2-C_8)$alkynyl, or $(C_3-C_8)$cycloalkyl. In one embodiment of a compound of formula (II), $R_1$ is $(C_2-C_4)$alkyl. In one embodiment of a compound of formula (II), $R_1$ is isopropyl. In one embodiment of a compound of formula (II), $R_2$ is $(C_2-C_4)$alkyl. In one embodiment of a compound of formula (II), $R_2$ is isopropyl. In one embodiment of a compound of formula (II), $R_3$ is $(C_2-C_4)$alkyl. In one embodiment of a compound of formula (II), $R_3$ is isopropyl.

In one embodiment, provided herein is a compound of formula (III):

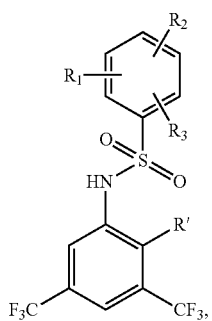

(III)

or an enantiomer, a mixture of enantiomers, or a mixture of two or more diastereomers thereof;
or a pharmaceutically acceptable salt, solvate, hydrate, or prodrug thereof; wherein R', $R_1$, $R_2$, and $R_3$ are each as defined herein.

In one embodiment of a compound of formula (III), $R_1$ is $(C_1-C_4)$alkyl. In one embodiment of a compound of formula (III), $R_1$ is methyl, ethyl, or isopropyl. In one embodiment of a compound of formula (III), $R_2$ is hydrogen, or $(C_1-C_4)$alkyl. In one embodiment of a compound of formula (III), $R_2$ is methyl, isopropyl, or tert-butyl. In one embodiment of a compound of formula (III), $R_3$ is $(C_1-C_4)$alkyl. In one embodiment of a compound of formula (III), $R_3$ is methyl, ethyl or isopropyl.

In one embodiment, provided herein is a compound of formula (III):

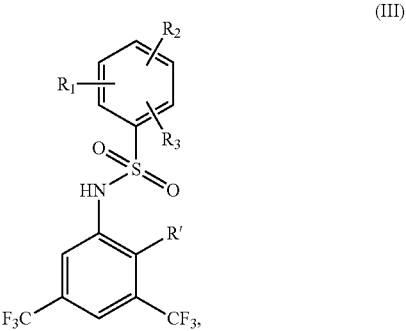

(III)

or an enantiomer, a mixture of enantiomers, or a mixture of two or more diastereomers thereof;
or a pharmaceutically acceptable salt, solvate, hydrate, or prodrug thereof; wherein:

R' is hydrogen, halogen, cyano, OH, $OC(O)R_a$, $C(O)R_a$, $C(O)OR_a$, $C(O)NR_aR_b$, $NR_aC(O)R_b$, $NR_aR_b$, $OS(O)R_a$, $SR_a$, $S(O)R_a$, $S(O)_2R_a$, $S(O)_2NR_aR_b$, $NR_aS(O)_2R_b$, $(C_1-C_8)$alkyl, $(C_2-C_8)$alkenyl, $(C_2-C_8)$alkynyl, $(C_1-C_8)$alkoxy, $(C_2-C_8)$alkenyloxy, $(C_2-C_8)$alkynyloxy, $(C_3-C_8)$cycloalkyl, or $(C_3-C_8)$cycloalkyloxy, wherein the alkyl, alkenyl, alkynyl, alkoxy, alkenyloxy, alkynyloxy, cycloalkyl, and cycloalkyloxy are each optionally substituted with one or more halogen;

$R_1$, $R_2$, and $R_3$ are independently $(C_2-C_6)$alkyl, $(C_2-C_8)$alkenyl, $(C_2-C_8)$alkynyl, or $(C_3-C_8)$cycloalkyl, each of which is optionally substituted with one or more halogen; and $R_a$ and $R_b$ are each independently hydrogen, $(C_1-C_8)$alkyl, $(C_2-C_8)$alkenyl, $(C_2-C_8)$alkynyl, $(C_1-C_8)$heteroalkyl, $(C_3-C_8)$cycloalkyl, $(C_7-C_{12})$aralkyl, phenyl, (5 to 6 membered) heteroaryl, or (3 to 7 membered)heterocyclyl; or $R_a$ and $R_b$ together form a 3 to 10 membered ring.

In one embodiment of a compound of formula (III), R' is hydrogen, halogen, cyano, $(C_1-C_8)$alkyl, $(C_2-C_8)$alkenyl, $(C_2-C_8)$alkynyl, $(C_1-C_8)$alkoxy, $(C_2-C_8)$alkenyloxy, $(C_2-C_8)$alkynyloxy, $(C_3-C_8)$cycloalkyl or $(C_3-C_8)$cycloalkyloxy, wherein the alkyl, alkenyl, alkynyl, alkoxy, alkenyloxy, alkynyloxy, cycloalkyl, and cycloalkyloxy are each optionally substituted with one or more halogen. In one embodiment of a compound of formula (III), R' is hydrogen, halogen, $(C_1-C_8)$alkyl, or $(C_1-C_8)$alkoxy, wherein the alkyl and alkoxyl are each optionally substituted with one or more halogen. In one embodiment of a compound of formula (III), R' is hydrogen, halogen, $(C_1-C_4)$alkyl, or $(C_1-C_4)$alkoxy, wherein the alkyl and alkoxyl are each optionally substituted with one or more halogen. In one embodiment of a compound of formula (III), R' is hydrogen, F, Cl, Br, $(C_1-C_4)$alkyl, $CF_3$, or $OCF_3$. In one embodiment of a compound of formula (III), R' is hydrogen or $(C_1-C_4)$alkyl. In one embodiment of a compound of formula (III), R' is hydrogen or methyl. In one embodiment of a compound of formula (III), R' is hydrogen. In another embodiment of a compound of formula (III), R' is methyl. In yet another embodiment of a compound of formula (III), R' is Cl.

In one embodiment of a compound of formula (III), $R_1$, $R_2$, and $R_3$ are independently $(C_2-C_6)$alkyl, $(C_2-C_8)$alkenyl, $(C_2-C_8)$alkynyl, or $(C_3-C_8)$cycloalkyl. In one embodiment of a compound of formula (III), $R_1$ is $(C_2-C_4)$alkyl. In one embodiment of a compound of formula (III), $R_1$ is isopropyl. In one embodiment of a compound of formula (III), $R_2$ is $(C_2-C_4)$alkyl. In one embodiment of a compound of formula (III), $R_2$ is isopropyl. In one embodiment of a compound of formula (III), $R_3$ is $(C_2-C_4)$alkyl. In one embodiment of a compound of formula (III), $R_3$ is isopropyl.

In one embodiment, provided herein is a compound of formula (IV):

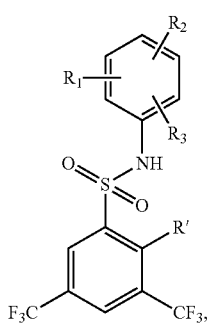

(IV)

or an enantiomer, a mixture of enantiomers, or a mixture of two or more diastereomers thereof;
or a pharmaceutically acceptable salt, solvate, hydrate, or prodrug thereof; wherein R', $R_1$, $R_2$, and $R_3$ are each as defined herein.

In one embodiment of a compound of formula (IV), $R_1$ is $(C_1-C_4)$alkyl. In one embodiment of a compound of formula (IV), $R_1$ is methyl, ethyl, or isopropyl. In one embodiment of a compound of formula (IV), $R_2$ is hydrogen, or $(C_1-C_4)$alkyl. In one embodiment of a compound of formula (IV), $R_2$ is methyl, isopropyl, or tert-butyl. In one embodiment of a compound of formula (IV), $R_3$ is $(C_1-C_4)$alkyl. In one embodiment of a compound of formula (IV), $R_3$ is methyl, ethyl or isopropyl.

In one embodiment, provided herein is a compound of formula (IV):

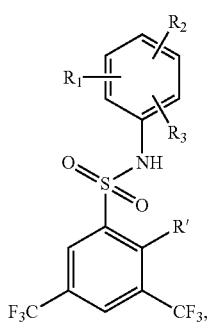

(IV)

or an enantiomer, a mixture of enantiomers, or a mixture of two or more diastereomers thereof;
or a pharmaceutically acceptable salt, solvate, hydrate, or prodrug thereof; wherein:
R' is hydrogen, halogen, cyano, OH, OC(O)$R_a$, C(O)$R_a$, C(O)OR$_a$, C(O)NR$_a$R$_b$, NR$_a$C(O)R$_b$, NR$_a$R$_b$, OS(O)R$_a$, SR$_a$, S(O)R$_a$, S(O)$_2$R$_a$, S(O)$_2$NR$_a$R$_b$, NR$_a$S(O)$_2$R$_b$, $(C_1-C_8)$alkyl, $(C_2-C_8)$alkenyl, $(C_2-C_8)$alkynyl, $(C_1-C_8)$alkoxy, $(C_2-C_8)$alkenyloxy, $(C_2-C_8)$alkynyloxy, $(C_3-C_8)$cycloalkyl, or $(C_3-C_8)$cycloalkyloxy, wherein the alkyl, alkenyl, alkynyl, alkoxy, alkenyloxy, alkynyloxy, cycloalkyl, and cycloalkyloxy are each optionally substituted with one or more halogen;

$R_1$, $R_2$, and $R_3$ are independently $(C_2-C_6)$alkyl, $(C_2-C_8)$alkenyl, $(C_2-C_8)$alkynyl, or $(C_3-C_8)$cycloalkyl, each of which is optionally substituted with one or more halogen; and $R_a$ and $R_b$ are each independently hydrogen, $(C_1-C_8)$alkyl, $(C_2-C_8)$alkenyl, $(C_2-C_8)$alkynyl, $(C_1-C_8)$heteroalkyl, $(C_3-C_8)$cycloalkyl, $(C_7-C_{12})$aralkyl, phenyl, (5 to 6 membered) heteroaryl, or (3 to 7 membered)heterocyclyl; or $R_a$ and $R_b$ together form a 3 to 10 membered ring.

In one embodiment of a compound of formula (IV), R' is hydrogen, halogen, cyano, $(C_1-C_8)$alkyl, $(C_2-C_8)$alkenyl, $(C_2-C_8)$alkynyl, $(C_1-C_8)$alkoxy, $(C_2-C_8)$alkenyloxy, $(C_2-C_8)$alkynyloxy, $(C_3-C_8)$cycloalkyl or $(C_3-C_8)$cycloalkyloxy, wherein the alkyl, alkenyl, alkynyl, alkoxy, alkenyloxy, alkynyloxy, cycloalkyl, and cycloalkyloxy are each optionally substituted with one or more halogen. In one embodiment of a compound of formula (IV), R' is hydrogen, halogen, $(C_1-C_8)$alkyl, or $(C_1-C_8)$alkoxy, wherein the alkyl and alkoxyl are each optionally substituted with one or more halogen. In one embodiment of a compound of formula (IV), R' is hydrogen, halogen, $(C_1-C_4)$alkyl, or $(C_1-C_4)$alkoxy, wherein the alkyl and alkoxyl are each optionally substituted with one or more halogen. In one embodiment of a compound of formula (IV), R' is hydrogen, F, Cl, Br, $(C_1-C_4)$alkyl, $CF_3$, or $OCF_3$. In one embodiment of a compound of formula (IV), R' is hydrogen or $(C_1-C_4)$alkyl. In one embodiment of a compound of formula (IV), R' is hydrogen or methyl. In one embodiment of a compound of formula (IV), R' is hydrogen. In another embodiment of a compound of formula (IV), R' is methyl. In yet another embodiment of a compound of formula (IV), R' is Cl.

In one embodiment of a compound of formula (IV), $R_1$, $R_2$, and $R_3$ are independently $(C_2-C_6)$alkyl, $(C_2-C_8)$alkenyl, $(C_2-C_8)$alkynyl, or $(C_3-C_8)$cycloalkyl. In one embodiment of a compound of formula (IV), $R_1$ is $(C_2-C_4)$alkyl. In one embodiment of a compound of formula (IV), $R_1$ is isopropyl. In one embodiment of a compound of formula (IV), $R_2$ is $(C_2-C_4)$alkyl. In one embodiment of a compound of formula (IV), $R_2$ is isopropyl. In one embodiment of a compound of formula (IV), $R_3$ is $(C_2-C_4)$alkyl. In one embodiment of a compound of formula (IV), $R_3$ is isopropyl.

In one embodiment, provided herein is a compound of formula (II-A):

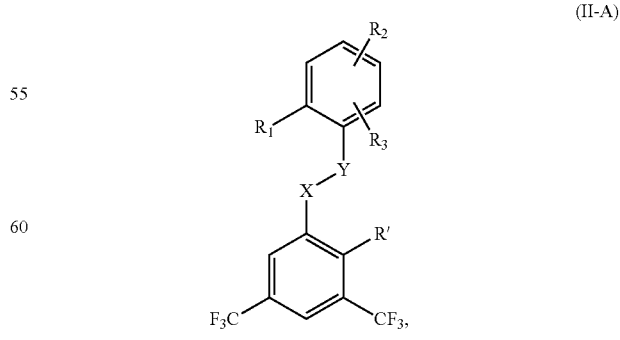

(II-A)

or an enantiomer, a mixture of enantiomers, or a mixture of two or more diastereomers thereof;

or a pharmaceutically acceptable salt, solvate, hydrate, or prodrug thereof; wherein R', $R_1$, $R_2$, and $R_3$ are each as defined herein.

In one embodiment of a compound of formula (II-A), $R_1$ is $(C_1-C_4)$alkyl. In one embodiment of a compound of formula (II-A), $R_1$ is methyl, ethyl, or isopropyl. In one embodiment of a compound of formula (II-A), $R_2$ is hydrogen, or $(C_1-C_4)$alkyl. In one embodiment of a compound of formula (II-A), $R_2$ is methyl, isopropyl, or tert-butyl. In one embodiment of a compound of formula (II-A), $R_3$ is $(C_1-C_4)$alkyl. In one embodiment of a compound of formula (II-A), $R_3$ is methyl, ethyl or isopropyl.

In one embodiment, provided herein is a compound of formula (II-A):

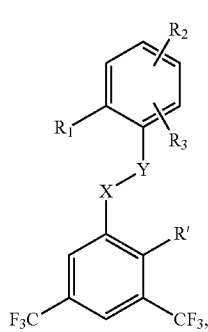

(II-A)

or an enantiomer, a mixture of enantiomers, or a mixture of two or more diastereomers thereof;
or a pharmaceutically acceptable salt, solvate, hydrate, or prodrug thereof; wherein:

X is NH, and Y is $S(O)_2$; or X is $S(O)_2$, and Y is NH;

R' is hydrogen, halogen, cyano, OH, $OC(O)R_a$, $C(O)R_a$, $C(O)OR_a$, $C(O)NR_aR_b$, $NR_aC(O)R_b$, $NR_aR_b$, $OS(O)R_a$, $SR_a$, $S(O)R_a$, $S(O)_2R_a$, $S(O)_2NR_aR_b$, $NR_aS(O)_2R_b$, $(C_1-C_8)$alkyl, $(C_2-C_8)$alkenyl, $(C_2-C_8)$alkynyl, $(C_1-C_8)$alkoxy, $(C_2-C_8)$alkenyloxy, $(C_2-C_8)$alkynyloxy, $(C_3-C_8)$cycloalkyl, or $(C_3-C_8)$cycloalkyloxy, wherein the alkyl, alkenyl, alkynyl, alkoxy, alkenyloxy, alkynyloxy, cycloalkyl, and cycloalkyloxy are each optionally substituted with one or more halogen;

$R_1$, $R_2$, and $R_3$ are independently $(C_2-C_6)$alkyl, $(C_2-C_8)$alkenyl, $(C_2-C_8)$alkynyl, or $(C_3-C_8)$cycloalkyl, each of which is optionally substituted with one or more halogen; and $R_a$ and $R_b$ are each independently hydrogen, $(C_1-C_8)$alkyl, $(C_2-C_8)$alkenyl, $(C_2-C_8)$alkynyl, $(C_1-C_8)$heteroalkyl, $(C_3-C_8)$cycloalkyl, $(C_7-C_{12})$aralkyl, phenyl, (5 to 6 membered) heteroaryl, or (3 to 7 membered)heterocyclyl; or $R_a$ and $R_b$ together form a 3 to 10 membered ring.

In one embodiment of a compound of formula (II-A), X is NH, and Y is $S(O)_2$. In another embodiment of a compound of formula (II-A), X is $S(O)_2$, and Y is NH.

In one embodiment of a compound of formula (II-A), R' is hydrogen, halogen, cyano, $(C_1-C_8)$alkyl, $(C_2-C_8)$alkenyl, $(C_2-C_8)$alkynyl, $(C_1-C_8)$alkoxy, $(C_2-C_8)$alkenyloxy, $(C_2-C_8)$alkynyloxy, $(C_3-C_8)$cycloalkyl or $(C_3-C_8)$cycloalkyloxy, wherein the alkyl, alkenyl, alkynyl, alkoxy, alkenyloxy, alkynyloxy, cycloalkyl, and cycloalkyloxy are each optionally substituted with one or more halogen. In one embodiment of a compound of formula (II-A), R' is hydrogen, halogen, $(C_1-C_8)$alkyl, or $(C_1-C_8)$alkoxy, wherein the alkyl and alkoxyl are each optionally substituted with one or more halogen. In one embodiment of a compound of formula (II-A), R' is hydrogen, halogen, $(C_1-C_4)$alkyl, or $(C_1-C_4)$alkoxy, wherein the alkyl and alkoxyl are each optionally substituted with one or more halogen. In one embodiment of a compound of formula (II-A), R' is hydrogen, F, Cl, Br, $(C_1-C_4)$alkyl, $CF_3$, or $OCF_3$. In one embodiment of a compound of formula (II-A), R' is hydrogen or $(C_1-C_4)$alkyl. In one embodiment of a compound of formula (II-A), R' is hydrogen or methyl. In one embodiment of a compound of formula (II-A), R' is hydrogen. In another embodiment of a compound of formula (II-A), R' is methyl. In yet another embodiment of a compound of formula (II-A), R' is Cl.

In one embodiment of a compound of formula (II-A), $R_1$, $R_2$, and $R_3$ are independently $(C_2-C_6)$alkyl, $(C_2-C_8)$alkenyl, $(C_2-C_8)$alkynyl, or $(C_3-C_8)$cycloalkyl. In one embodiment of a compound of formula (II-A), $R_1$ is $(C_2-C_4)$alkyl. In one embodiment of a compound of formula (II-A), $R_1$ is isopropyl. In one embodiment of a compound of formula (II-A), $R_2$ is $(C_2-C_4)$alkyl. In one embodiment of a compound of formula (II-A), $R_2$ is isopropyl. In one embodiment of a compound of formula (II-A), $R_3$ is $(C_2-C_4)$alkyl. In one embodiment of a compound of formula (II-A), $R_3$ is isopropyl.

In one embodiment, provided herein is a compound of formula (II-A-1):

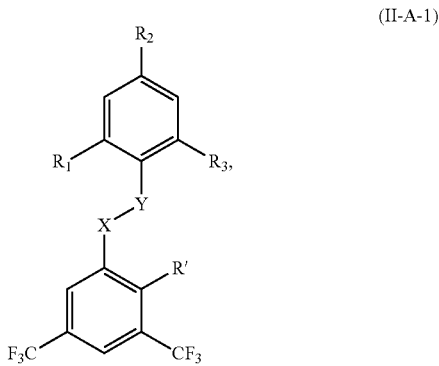

(II-A-1)

or an enantiomer, a mixture of enantiomers, or a mixture of two or more diastereomers thereof;

or a pharmaceutically acceptable salt, solvate, hydrate, or prodrug thereof; wherein R', $R_1$, $R_2$, and $R_3$ are each as defined herein.

In one embodiment of a compound of formula (II-A-1), $R_1$ is $(C_1-C_4)$alkyl. In one embodiment of a compound of formula (II-A-1), $R_1$ is methyl, ethyl, or isopropyl. In one embodiment of a compound of formula (II-A-1), $R_2$ is hydrogen, or $(C_1-C_4)$alkyl. In one embodiment of a compound of formula (II-A-1), $R_2$ is methyl, isopropyl, or tert-butyl. In one embodiment of a compound of formula (II-A-1), $R_3$ is $(C_1-C_4)$alkyl. In one embodiment of a compound of formula (II-A-1), $R_3$ is methyl, ethyl or isopropyl.

In one embodiment, provided herein is a compound of formula (II-A-1):

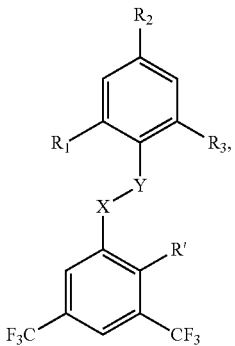

(II-A-1)

or an enantiomer, a mixture of enantiomers, or a mixture of two or more diastereomers thereof;
or a pharmaceutically acceptable salt, solvate, hydrate, or prodrug thereof; wherein:

X is NH, and Y is $S(O)_2$; or X is $S(O)_2$, and Y is NH;
R' is hydrogen, halogen, cyano, OH, $OC(O)R_a$, $C(O)R_a$, $C(O)OR_a$, $C(O)NR_aR_b$, $NR_aC(O)R_b$, $NR_aR_b$, $OS(O)R_a$, $SR_a$, $S(O)R_a$, $S(O)_2R_a$, $S(O)_2NR_aR_b$, $NR_aS(O)_2R_b$, $(C_1-C_8)$ alkyl, $(C_2-C_8)$alkenyl, $(C_2-C_8)$alkynyl, $(C_1-C_8)$alkoxy, $(C_2-C_8)$alkenyloxy, $(C_2-C_8)$alkynyloxy, $(C_3-C_8)$cycloalkyl, or $(C_3-C_8)$cycloalkyloxy, wherein the alkyl, alkenyl, alkynyl, alkoxy, alkenyloxy, alkynyloxy, cycloalkyl, and cycloalkyloxy are each optionally substituted with one or more halogen;

$R_1$, $R_2$, and $R_3$ are independently $(C_2-C_6)$alkyl, $(C_2-C_8)$ alkenyl, $(C_2-C_8)$alkynyl, or $(C_3-C_8)$cycloalkyl, each of which is optionally substituted with one or more halogen; and $R_a$ and $R_b$ are each independently hydrogen, $(C_1-C_8)$alkyl, $(C_2-C_8)$alkenyl, $(C_2-C_8)$alkynyl, $(C_1-C_8)$heteroalkyl, $(C_3-C_8)$cycloalkyl, $(C_7-C_{12})$aralkyl, phenyl, (5 to 6 membered) heteroaryl, or (3 to 7 membered)heterocyclyl; or $R_a$ and $R_b$ together form a 3 to 10 membered ring.

In one embodiment of a compound of formula (II-A-1), X is NH, and Y is $S(O)_2$. In another embodiment of a compound of formula (II-A-1), X is $S(O)_2$, and Y is NH.

In one embodiment of a compound of formula (II-A-1), R' is hydrogen, halogen, cyano, $(C_1-C_8)$alkyl, $(C_2-C_8)$alkenyl, $(C_2-C_8)$alkynyl, $(C_1-C_8)$alkoxy, $(C_2-C_8)$alkenyloxy, $(C_2-C_8)$ alkynyloxy, $(C_3-C_8)$cycloalkyl or $(C_3-C_8)$cycloalkyloxy, wherein the alkyl, alkenyl, alkynyl, alkoxy, alkenyloxy, alkynyloxy, cycloalkyl, and cycloalkyloxy are each optionally substituted with one or more halogen. In one embodiment of a compound of formula (II-A-1), R' is hydrogen, halogen, $(C_1-C_8)$alkyl, or $(C_1-C_8)$alkoxy, wherein the alkyl and alkoxyl are each optionally substituted with one or more halogen. In one embodiment of a compound of formula (II-A-1), R' is hydrogen, halogen, $(C_1-C_4)$alkyl, or $(C_1-C_4)$ alkoxy, wherein the alkyl and alkoxyl are each optionally substituted with one or more halogen. In one embodiment of a compound of formula (II-A-1), R' is hydrogen, F, Cl, Br, $(C_1-C_4)$alkyl, $CF_3$, or $OCF_3$. In one embodiment of a compound of formula (II-A-1), R' is hydrogen or $(C_1-C_4)$alkyl. In one embodiment of a compound of formula (II-A-1), R' is hydrogen or methyl. In one embodiment of a compound of formula (II-A-1), R' is hydrogen. In another embodiment of a compound of formula (II-A-1), R' is methyl. In yet another embodiment of a compound of formula (II-A-1), R' is Cl.

In one embodiment of a compound of formula (II-A-1), $R_1$, $R_2$, and $R_3$ are independently $(C_2-C_6)$alkyl, $(C_2-C_8)$ alkenyl, $(C_2-C_8)$alkynyl, or $(C_3-C_8)$cycloalkyl. In one embodiment of a compound of formula (II-A-1), $R_1$ is $(C_2-C_4)$alkyl. In one embodiment of a compound of formula (II-A-1), $R_1$ is isopropyl. In one embodiment of a compound of formula (II-A-1), $R_2$ is $(C_2-C_4)$alkyl. In one embodiment of a compound of formula (II-A-1), $R_2$ is isopropyl. In one embodiment of a compound of formula (II-A-1), $R_3$ is $(C_2-C_4)$alkyl. In one embodiment of a compound of formula (II-A-1), $R_3$ is isopropyl.

In one embodiment, provided herein is a compound of formula (III-A-1):

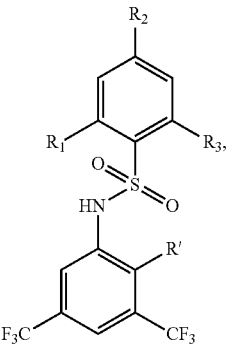

(III-A-1)

or an enantiomer, a mixture of enantiomers, or a mixture of two or more diastereomers thereof;
or a pharmaceutically acceptable salt, solvate, hydrate, or prodrug thereof; wherein R', $R_1$, $R_2$, and $R_3$ are each as defined herein.

In one embodiment of a compound of formula (III-A-1), $R_1$ is $(C_1-C_4)$alkyl. In one embodiment of a compound of formula (III-A-1), $R_1$ is methyl, ethyl, or isopropyl. In one embodiment of a compound of formula (III-A-1), $R_2$ is hydrogen, or $(C_1-C_4)$alkyl. In one embodiment of a compound of formula (III-A-1), $R_2$ is methyl, isopropyl, or tert-butyl. In one embodiment of a compound of formula (III-A-1), $R_3$ is $(C_1-C_4)$alkyl. In one embodiment of a compound of formula (III-A-1), $R_3$ is methyl, ethyl or isopropyl.

In one embodiment, provided herein is a compound of formula (III-A-1):

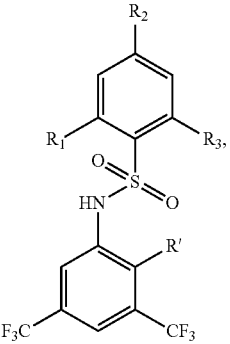

(III-A-1)

or an enantiomer, a mixture of enantiomers, or a mixture of two or more diastereomers thereof;

or a pharmaceutically acceptable salt, solvate, hydrate, or prodrug thereof; wherein:

X is NH, and Y is S(O)$_2$; or X is S(O)$_2$, and Y is NH;

R' is hydrogen, halogen, cyano, OH, OC(O)R$_a$, C(O)R$_a$, C(O)OR$_a$, C(O)NR$_a$R$_b$, NR$_a$C(O)R$_b$, NR$_a$R$_b$, OS(O)R$_a$, SR$_a$, S(O)R$_a$, S(O)$_2$R$_a$, S(O)$_2$NR$_a$R$_b$, NR$_a$S(O)$_2$R$_b$, (C$_1$-C$_8$)alkyl, (C$_2$-C$_8$)alkenyl, (C$_2$-C$_8$)alkynyl, (C$_1$-C$_8$)alkoxy, (C$_2$-C$_8$)alkenyloxy, (C$_2$-C$_8$)alkynyloxy, (C$_3$-C$_8$)cycloalkyl, or (C$_3$-C$_8$)cycloalkyloxy, wherein the alkyl, alkenyl, alkynyl, alkoxy, alkenyloxy, alkynyloxy, cycloalkyl, and cycloalkyloxy are each optionally substituted with one or more halogen;

R$_1$, R$_2$, and R$_3$ are independently (C$_2$-C$_6$)alkyl, (C$_2$-C$_8$)alkenyl, (C$_2$-C$_8$)alkynyl, or (C$_3$-C$_8$)cycloalkyl, each of which is optionally substituted with one or more halogen; and R$_a$ and R$_b$ are each independently hydrogen, (C$_1$-C$_8$)alkyl, (C$_2$-C$_8$)alkenyl, (C$_2$-C$_8$)alkynyl, (C$_1$-C$_8$)heteroalkyl, (C$_3$-C$_8$)cycloalkyl, (C$_7$-C$_{12}$)aralkyl, phenyl, (5 to 6 membered) heteroaryl, or (3 to 7 membered)heterocyclyl; or R$_a$. and R$_b$ together form a 3 to 10 membered ring.

In one embodiment of a compound of formula (III-A-1), X is NH, and Y is S(O)$_2$. In another embodiment of a compound of formula (III-A-1), X is S(O)$_2$, and Y is NH.

In one embodiment of a compound of formula (III-A-1), R' is hydrogen, halogen, cyano, (C$_1$-C$_8$)alkyl, (C$_2$-C$_8$)alkenyl, (C$_2$-C$_8$)alkynyl, (C$_1$-C$_8$)alkoxy, (C$_2$-C$_8$)alkenyloxy, (C$_2$-C$_8$)alkynyloxy, (C$_3$-C$_8$)cycloalkyl or (C$_3$-C$_8$)cycloalkyloxy, wherein the alkyl, alkenyl, alkynyl, alkoxy, alkenyloxy, alkynyloxy, cycloalkyl, and cycloalkyloxy are each optionally substituted with one or more halogen. In one embodiment of a compound of formula (III-A-1), R' is hydrogen, halogen, (C$_1$-C$_8$)alkyl, or (C$_1$-C$_8$)alkoxy, wherein the alkyl and alkoxyl are each optionally substituted with one or more halogen. In one embodiment of a compound of formula (III-A-1), R' is hydrogen, halogen, (C$_1$-C$_4$)alkyl, or (C$_1$-C$_4$)alkoxy, wherein the alkyl and alkoxyl are each optionally substituted with one or more halogen. In one embodiment of a compound of formula (III-A-1), R' is hydrogen, F, Cl, Br, (C$_1$-C$_4$)alkyl, CF$_3$, or OCF$_3$. In one embodiment of a compound of formula (III-A-1), R' is hydrogen or (C$_1$-C$_4$)alkyl. In one embodiment of a compound of formula (III-A-1), R' is hydrogen or methyl. In one embodiment of a compound of formula (III-A-1), R' is hydrogen. In another embodiment of a compound of formula (III-A-1), R' is methyl. In yet another embodiment of a compound of formula (III-A-1), R' is Cl.

In one embodiment of a compound of formula (III-A-1), R$_1$, R$_2$, and R$_3$ are independently (C$_2$-C$_6$)alkyl, (C$_2$-C$_8$)alkenyl, (C$_2$-C$_8$)alkynyl, or (C$_3$-C$_8$)cycloalkyl. In one embodiment of a compound of formula (III-A-1), R$_1$ is (C$_2$-C$_4$)alkyl. In one embodiment of a compound of formula (III-A-1), R$_1$ is isopropyl. In one embodiment of a compound of formula (III-A-1), R$_2$ is (C$_2$-C$_4$)alkyl. In one embodiment of a compound of formula (III-A-1), R$_2$ is isopropyl. In one embodiment of a compound of formula (III-A-1), R$_3$ is (C$_2$-C$_4$)alkyl. In one embodiment of a compound of formula (III-A-1), R$_3$ is isopropyl.

In one embodiment, specific examples of the compound of formula (III-A-1) include, but are not limited to, the following:

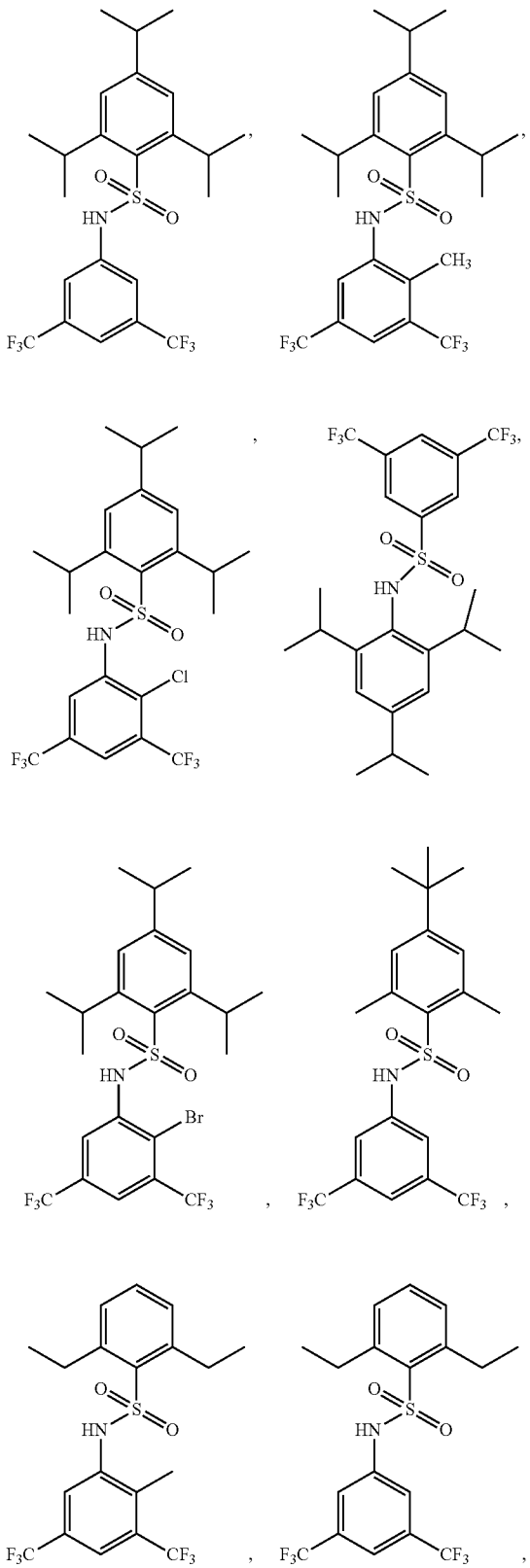

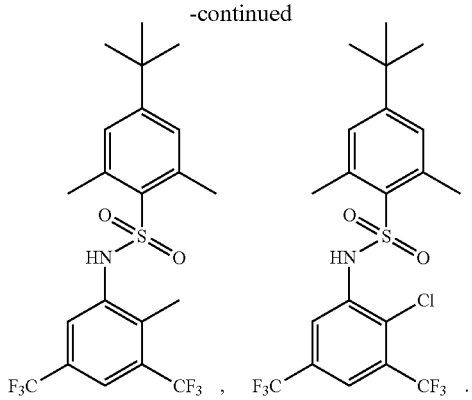

All of the combinations of the above embodiments are encompassed by this invention.

It should be noted that if there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it. Where the compound provided herein contains an alkenyl or alkenylene group, the compound may exist as one or mixture of geometric cis/trans (or Z/E) isomers. Where structural isomers are inter-convertible, the compound may exist as a single tautomer or a mixture of tautomers. This can take the form of proton tautomerism in the compound that contains, for example, an imino, keto, or oxime group; or so-called valence tautomerism in the compound that contain an aromatic moiety. It follows that a single compound may exhibit more than one type of isomerism.

The compounds provided herein may be enantiomerically pure, such as a single enantiomer or a single diastereomer, or be stereoisomeric mixtures, such as a mixture of enantiomers, e.g., a racemic mixture of two enantiomers; or a mixture of two or more diastereomers. In some instances, for compounds that undergo epimerization in vivo, one of skill in the art will recognize that administration of a compound in its (R) form is equivalent to administration of the compound in its (S) form. Conventional techniques for the preparation/isolation of individual enantiomers include synthesis from a suitable optically pure precursor, asymmetric synthesis from achiral starting materials, or resolution of an enantiomeric mixture, for example, by chiral chromatography, recrystallization, resolution, diastereomeric salt formation, or derivatization into diastereomeric adducts followed by separation.

When the compound provided herein contains an acidic or basic moiety, it may also be provided as a pharmaceutically acceptable salt (See, e.g., Berge et al., *J. Pharm. Sci.* 1977, 66, 1-19; and *Handbook of Pharmaceutical Salts, Properties, and Use*, Stahl and Wermuth, ed.; Wiley-VCH and VHCA, Zurich, 2002).

Suitable acids for use in the preparation of pharmaceutically acceptable salts include, but are not limited to, acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, boric acid, (+)-camphoric acid, camphorsulfonic acid, (+)-(1S)-camphor-10-sulfonic acid, capric acid, caproic acid, caprylic acid, cinnamic acid, citric acid, cyclamic acid, cyclohexanesulfamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucuronic acid, L-glutamic acid, α-oxoglutaric acid, glycolic acid, hippuric acid, hydrobromic acid, hydrochloric acid, hydroiodic acid, (+)-L-lactic acid, (±)-DL-lactic acid, lactobionic acid, lauric acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, perchloric acid, phosphoric acid, L-pyroglutamic acid, saccharic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid, undecylenic acid, and valeric acid.

Suitable bases for use in the preparation of pharmaceutically acceptable salts, including, but not limited to, inorganic bases, such as magnesium hydroxide, calcium hydroxide, potassium hydroxide, zinc hydroxide, or sodium hydroxide; and organic bases, such as primary, secondary, tertiary, and quaternary, aliphatic and aromatic amines, including L-arginine, benethamine, benzathine, choline, deanol, diethanolamine, diethylamine, dimethylamine, dipropylamine, diisopropylamine, 2-(diethylamino)-ethanol, ethanolamine, ethylamine, ethylenediamine, isopropylamine, N-methylglucamine, hydrabamine, 1H-imidazole, L-lysine, morpholine, 4-(2-hydroxyethyl)-morpholine, methylamine, piperidine, piperazine, propylamine, pyrrolidine, 1-(2-hydroxyethyl)-pyrrolidine, pyridine, quinuclidine, quinoline, isoquinoline, secondary amines, triethanolamine, trimethylamine, triethylamine, N-methyl-D-glucamine, 2-amino-2-(hydroxymethyl)-1,3-propanediol, and tromethamine.

In certain embodiments, the compounds provided herein are pharmacologically acceptable salts of the compounds with one or more of hydrochloric, sulfuric, phosphoric, acetic, citric, oxalic, malonic, salicylic, malic, fumaric, succinic, ascorbic, maleic, methanesulfonic, and isoethonic acids; or with one or more of potassium carbonate, sodium or potassium hydroxide, ammonia, triethylamine, and triethanolamine.

The compound provided herein may also be provided as a prodrug, which is a functional derivative of the compound, for example, of Formula I and is readily convertible into the parent compound in vivo. Prodrugs are often useful because, in some situations, they may be easier to administer than the parent compound. They may, for instance, be bioavailable by oral administration whereas the parent compound is not. The prodrug may also have enhanced solubility in pharmaceutical compositions over the parent compound. A prodrug may be converted into the parent drug by various mechanisms, including enzymatic processes and metabolic hydrolysis. See, e.g., Harper, *Progress in Drug Research* 1962, 4, 221-294; Morozowich et al. in Design of Biopharmaceutical Properties through Prodrugs and Analogs, Roche ed., APHA Acad. Pharm. Sci. 1977; Bioreversible Carriers in Drug in Drug Design, Theory and Application, Roche ed., APHA Acad. Pharm. Sci. 1987; Design of Prodrugs, Bundgaard, Elsevier, 1985; Wang et al., *Curr. Pharm. Design* 1999, 5, 265-287; Pauletti et al., *Adv. Drug. Delivery Rev.* 1997, 27, 235-256; Mizen et al., *Pharm. Biotech.* 1998, 11, 345-365; Gaignault et al., *Pract. Med. Chem.* 1996, 671-696; Asgharnejad in Transport Processes in Pharmaceutical Systems, Amidon et al., ed., Marcell Dekker, 185-218, 2000; Balant et al., *Eur. J. Drug Metab. Pharmacokinet.* 1990, 15, 143-53; Balimane & Sinko, *Adv. Drug Delivery Rev.* 1999, 39, 183-209; Browne, *Clin. Neuropharmacol.* 1997, 20, 1-12; Bundgaard, *Arch. Pharm. Chem.* 1979, 86, 1-39; Bundgaard, *Controlled Drug Delivery* 1987, 17, 179-96; Bundgaard, *Adv. Drug Delivery Rev.* 1992, 8, 1-38; Fleisher et al., *Adv. Drug Delivery Rev.* 1996, 19, 115-130; Fleisher et al., *Methods Enzymol.* 1985, 112, 360-381; Farquhar et al., *J. Pharm. Sci.* 1983, 72, 324-325; Freeman et al., *J. Chem. Soc., Chem. Commun.* 1991, 875-877; Friis and Bundgaard, *Eur. J. Pharm. Sci.* 1996, 4, 49-59; Gangwar et al., *Des. Biopharm. Prop. Prodrugs Analogs*, 1977, 409-421; Nathwani and Wood, *Drugs* 1993, 45, 866-94; Sinhababu and Thakker, *Adv. Drug Delivery Rev.* 1996, 19, 241-273; Stella et al., *Drugs* 1985, 29, 455-73; Tan et al., *Adv. Drug Delivery Rev.* 1999, 39, 117-151; Taylor, *Adv. Drug Delivery Rev.* 1996, 19, 131-148; Valentino and Borchardt, *Drug Discovery Today* 1997, 2, 148-155; Wiebe and Knaus, *Adv. Drug Delivery Rev.* 1999, 39, 63-80; and Waller et al., *Br. J. Clin. Pharmac.* 1989, 28, 497-507.

C. METHODS OF SYNTHESIS

Schemes below provide exemplary synthetic methods for the preparation of the compounds provided herein. One of ordinary skill in the art will understand that similar methods may be employed to prepare the compounds provided herein. In other words, one of ordinary skill in the art will recognize that suitable adjustments to reagents, protecting groups, reaction conditions, and reaction sequences may be employed to prepare a desired embodiment. The reaction may be scaled upwards or downwards to suit the amount of material to be prepared. In one embodiment, the compounds provided herein may be prepared by the procedures and techniques similar to those disclosed in the Examples. In one embodiment, the compounds provided herein may be prepared by procedures and techniques known in the art for coupling sulfonyl chlorides with amines. In one embodiment, the sulfonyl chlorides are prepared by procedures and techniques known in the art.

In one embodiment, the starting material used to prepare the compounds provided herein may be obtained from a commercial source. In one embodiment, the starting material used to prepare the compounds provided herein may be prepared following the procedures or conditions known in the art.

In one embodiment, the compounds provided herein may be prepared following Scheme 1. In one embodiment, the compounds are prepared by adding an excess or approximately equal molar amount of the sulfonyl chloride to a solution of a suitable amine, and a base, such as, e.g., N,N-diisopropylethylamine, in a solvent, such as, e.g., dichloromethane. In one embodiment, the compounds are prepared by adding an excess or approximately equal molar amount of the sulfonyl chloride to a solution of a suitable amine in a basic solvent, such as, e.g., pyridine. In one embodiment, after the reaction is stirred at room temperature until the reaction is complete, as monitored by, e.g., thin layer chromatography. In one embodiment, the reaction undergoes an aqueous workup washing with dilute HCl, followed by saturated aqueous $NaHCO_3$ solution and brine. In one embodiment, the reaction undergoes an aqueous workup washing with 0.1N HCl, followed by 0.1 N NaOH solution and brine. In one embodiment, after the aqueous workup the reaction mixture is dried over $MgSO_4$ and concentrated. In one embodiment, the compound may be further purified by column chromatography or by passing through a silica gel plug using an eluent, such as ethyl acetate/hexanes. In one embodiment, the compound may be further purified using trituration with hexanes. In one embodiment, the compound is analyzed by LCMS. In one embodiment, the compound is analyzed by $^1$H NMR.

In one embodiment, a compound of formula (I), wherein X is NH and Y is $S(O)_2$, may be prepared following Scheme 1, wherein the intermediates I-1 and I-2 may be obtained from a commercial source or prepared following procedures known in the art. R, R', and n are as defined herein elsewhere. In one embodiment, the base used in the reaction of Scheme 1 is triethylamine or diisopropylethylamine. In one embodiment, the reaction of Scheme 1 is carried out in a basic solvent. In one embodiment, the reaction of Scheme 1 is carried out in dry pyridine.

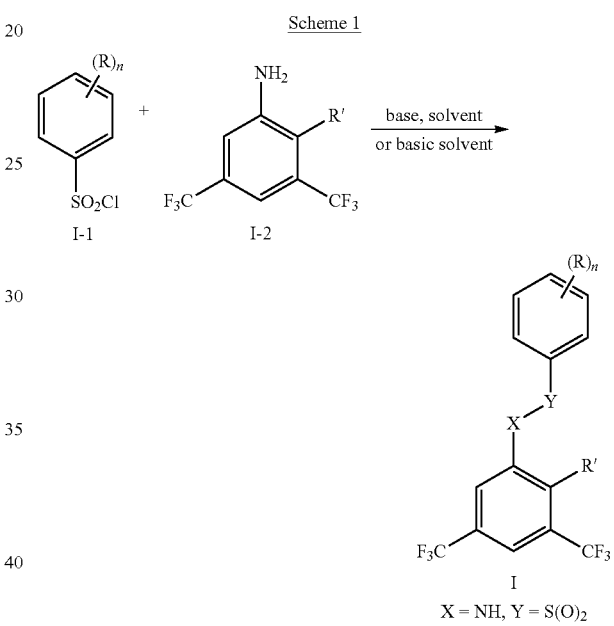

Scheme 1

In one embodiment, a compound of formula (I), wherein X is $S(O)_2$ and Y is NH, may be prepared following Scheme 2, wherein the intermediates I-3 and I-4 may be obtained from a commercial source or prepared following procedures known in the art. R, R', and n are as defined herein elsewhere. In one embodiment, the base used in the reaction of Scheme 2 is triethylamine or diisopropylethylamine. In one embodiment, the reaction of Scheme 2 is carried out in a basic solvent. In one embodiment, the reaction of Scheme 2 is carried out in dry pyridine.

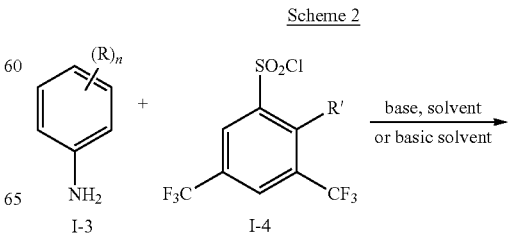

Scheme 2

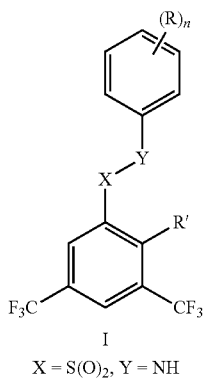

X = S(O)₂, Y = NH

In one embodiment, the compounds provided herein may be made by the procedures and techniques disclosed in the Examples, as well as known organic synthesis techniques for coupling sulfonyl chlorides and amines.

D. PHARMACEUTICAL COMPOSITIONS

In one embodiment, provided herein is a pharmaceutical composition comprising a compound of formula (I) as defined herein elsewhere, or an enantiomer, a mixture of enantiomers or a mixture of diastereomers thereof, or a pharmaceutically acceptable salt, solvate, hydrate or prodrug thereof, and at least one pharmaceutically acceptable excipient, adjuvant, carrier, buffer, or stabiliser.

In one embodiment, the pharmaceutically acceptable excipient, adjuvant, carrier, buffer, or stabiliser is non-toxic and does not interfere with the efficacy of the active ingredient. The precise nature of the carrier or other material will depend on the route of administration, which may be oral or by injection, such as cutaneous, subcutaneous, or intravenous injection.

In one embodiment, the pharmaceutical compositions are provided in a dosage form for oral administration, which comprise a compound provided herein, e.g., a compound of formula (I), or an enantiomer, a mixture of enantiomers or a mixture of diastereomers thereof, or a pharmaceutically acceptable salt, solvate, hydrate or prodrug thereof, and one or more pharmaceutically acceptable excipients or carriers. The pharmaceutical compositions provided herein that are formulated for oral administration may be in tablet, capsule, powder, or liquid form. A tablet may comprise a solid carrier or an adjuvant. Liquid pharmaceutical compositions generally comprise a liquid carrier such as water, petroleum, animal or vegetable oils, or mineral oil or synthetic oil. Physiological saline solution, dextrose or other saccharide solution, or glycols such as ethylene glycol, propylene glycol, or polyethylene glycol may be included. A capsule may comprise a solid carrier such as gelatin.

In another embodiment, the pharmaceutical compositions are provided in a dosage form for parenteral administration, and one or more pharmaceutically acceptable excipients or carriers. Where pharmaceutical compositions may be formulated for intravenous, cutaneous or subcutaneous injection, the active ingredient will be in the form of a parenterally acceptable aqueous solution, which is pyrogen-free and has a suitable pH, isotonicity, and stability. Those of relevant skill in the art are well able to prepare suitable solutions using, for example, isotonic vehicles, such as Sodium Chloride injection, Ringer's injection, or Lactated Ringer's injection. Preservatives, stabilisers, buffers, antioxidants, and/or other additives may be included as required.

In yet another embodiment, the pharmaceutical compositions are provided in a dosage form for topical administration, which comprise a compound provided herein, and one or more pharmaceutically acceptable excipients or carriers.

In one embodiment, the pharmaceutical compositions can also be formulated as modified release dosage forms, including delayed-, extended-, prolonged-, sustained-, pulsatile-, controlled-, accelerated- and fast-, targeted-, programmed-release, and gastric retention dosage forms. These dosage forms can be prepared according to conventional methods and techniques known to those skilled in the art (see, e.g., Remington: *The Science and Practice of Pharmacy, supra; Modified-Release Drug Delivery Technology,* 2nd Ed., Rathbone et al., eds., Marcel Dekker, Inc.: New York, N.Y., 2008).

In one embodiment, the pharmaceutical compositions provided herein can be provided in a unit-dosage form or multiple-dosage form. A unit-dosage form, as used herein, refers to physically discrete a unit suitable for administration to a human and animal subject, and packaged individually as is known in the art. Each unit-dose contains a predetermined quantity of an active ingredient(s) sufficient to produce the desired therapeutic effect, in association with the required pharmaceutical carriers or excipients. Examples of a unit-dosage form include an ampoule, syringe, and individually packaged tablet and capsule. A unit-dosage form may be administered in fractions or multiples thereof. A multiple-dosage form is a plurality of identical unit-dosage forms packaged in a single container to be administered in segregated unit-dosage form. Examples of a multiple-dosage form include a vial, bottle of tablets or capsules, or bottle of pints or gallons.

In one embodiment, the pharmaceutical compositions provided herein can be administered at once, or multiple times at intervals of time. It is understood that the precise dosage and duration of treatment may vary with the age, weight, and condition of the patient being treated, and may be determined empirically using known testing protocols or by extrapolation from in vivo or in vitro test or diagnostic data. It is further understood that for any particular individual, specific dosage regimens should be adjusted over time according to the individual need and the professional judgment of the person administering or supervising the administration of the formulations.

In another embodiment, the pharmaceutical compositions provided herein further comprise one or more chemotherapeutic agents as defined herein.

In yet another embodiment, provided herein is the use of a compound of formula (I), or an enantiomer, a mixture of enantiomers or a mixture of diastereomers thereof, or a pharmaceutically acceptable salt, solvate, hydrate or prodrug thereof, in the manufacture of a medicament for the treatment of one or more disorders disclosed herein. In certain embodiments, the medicament is in tablet, capsule, powder, or liquid form. In certain embodiments, the medicament is formulated as described herein.

1. Oral Administration

In one embodiment, the pharmaceutical compositions provided herein for oral administration can be provided in solid, semisolid, or liquid dosage forms for oral administration. As used herein, oral administration also includes buccal, lingual, and sublingual administration. Suitable oral dosage forms include, but are not limited to, tablets, fast-melts, chewable tablets, capsules, pills, strips, troches, lozenges, pastilles, cachets, pellets, medicated chewing gum, bulk powders, effervescent or non-effervescent powders or granules, oral mists, solutions, emulsions, suspensions, wafers, sprinkles, elixirs, and syrups. In addition to the active ingredient(s), the pharmaceutical compositions can contain one or more pharmaceutically acceptable carriers or excipients, including, but not limited to, binders, fillers, diluents, disintegrants, wetting agents, lubricants, glidants, coloring agents, dye-migration inhibitors, sweetening agents, flavoring agents, emulsifying agents, suspending and dispersing agents, preservatives, solvents, non-aqueous liquids, organic acids, and sources of carbon dioxide.

In one embodiment, binders or granulators impart cohesiveness to a tablet to ensure the tablet remaining intact after compression. Suitable binders or granulators include, but are not limited to, starches, such as corn starch, potato starch, and pre-gelatinized starch (e.g., STARCH 1500); gelatin; sugars, such as sucrose, glucose, dextrose, molasses, and lactose; natural and synthetic gums, such as acacia, alginic acid, alginates, extract of Irish moss, panwar gum, ghatti gum, mucilage of isabgol husks, carboxymethylcellulose, methylcellulose, polyvinylpyrrolidone (PVP), Veegum, larch arabogalactan, powdered tragacanth, and guar gum; celluloses, such as ethyl cellulose, cellulose acetate, carboxymethyl cellulose calcium, sodium carboxymethyl cellulose, methyl cellulose, hydroxyethylcellulose (HEC), hydroxypropylcellulose (HPC), hydroxypropyl methyl cellulose (HPMC); microcrystalline celluloses, such as AVICEL-PH-101, AVICEL-PH-103, AVICEL RC-581, AVICEL-PH-105 (FMC Corp., Marcus Hook, Pa.); and mixtures thereof. Suitable fillers include, but are not limited to, talc, calcium carbonate, microcrystalline cellulose, powdered cellulose, dextrates, kaolin, mannitol, silicic acid, sorbitol, starch, pre-gelatinized starch, and mixtures thereof. The amount of a binder or filler in the pharmaceutical compositions provided herein varies upon the type of formulation, and is readily discernible to those of ordinary skill in the art. The binder or filler may be present from about 50 to about 99% by weight in the pharmaceutical compositions provided herein.

In one embodiment, suitable diluents include, but are not limited to, dicalcium phosphate, calcium sulfate, lactose, sorbitol, sucrose, inositol, cellulose, kaolin, mannitol, sodium chloride, dry starch, and powdered sugar. Certain diluents, such as mannitol, lactose, sorbitol, sucrose, and inositol, when present in sufficient quantity, can impart properties to some compressed tablets that permit disintegration in the mouth by chewing. Such compressed tablets can be used as chewable tablets. The amount of a diluent in the pharmaceutical compositions provided herein varies upon the type of formulation, and is readily discernible to those of ordinary skill in the art.

In one embodiment, suitable disintegrants include, but are not limited to, agar; bentonite; celluloses, such as methylcellulose and carboxymethylcellulose; wood products; natural sponge; cation-exchange resins; alginic acid; gums, such as guar gum and Veegum HV; citrus pulp; cross-linked celluloses, such as croscarmellose; cross-linked polymers, such as crospovidone; cross-linked starches; calcium carbonate; microcrystalline cellulose, such as sodium starch glycolate; polacrilin potassium; starches, such as corn starch, potato starch, tapioca starch, and pre-gelatinized starch; clays; aligns; and mixtures thereof. The amount of a disintegrant in the pharmaceutical compositions provided herein varies upon the type of formulation, and is readily discernible to those of ordinary skill in the art. The amount of a disintegrant in the pharmaceutical compositions provided herein varies upon the type of formulation, and is readily discernible to those of ordinary skill in the art. The pharmaceutical compositions provided herein may contain from about 0.5 to about 15% or from about 1 to about 5% by weight of a disintegrant.

In one embodiment, suitable lubricants include, but are not limited to, calcium stearate; magnesium stearate; mineral oil; light mineral oil; glycerin; sorbitol; mannitol; glycols, such as glycerol behenate and polyethylene glycol (PEG); stearic acid; sodium lauryl sulfate; talc; hydrogenated vegetable oil, including peanut oil, cottonseed oil, sunflower oil, sesame oil, olive oil, corn oil, and soybean oil; zinc stearate; ethyl oleate; ethyl laureate; agar; starch; lycopodium; silica or silica gels, such as AEROSIL® 200 (W.R. Grace Co., Baltimore, Md.) and CAB-O-SIL® (Cabot Co. of Boston, Mass.); and mixtures thereof. The pharmaceutical compositions provided herein may contain about 0.1 to about 5% by weight of a lubricant.

In one embodiment, suitable glidants include, but are not limited to, colloidal silicon dioxide, CAB-O-SIL® (Cabot Co. of Boston, Mass.), and asbestos-free talc. Suitable coloring agents include, but are not limited to, any of the approved, certified, water soluble FD&C dyes, and water insoluble FD&C dyes suspended on alumina hydrate, and color lakes and mixtures thereof. A color lake is the combination by adsorption of a water-soluble dye to a hydrous oxide of a heavy metal, resulting in an insoluble form of the dye. Suitable flavoring agents include, but are not limited to, natural flavors extracted from plants, such as fruits, and synthetic blends of compounds which produce a pleasant taste sensation, such as peppermint and methyl salicylate. Suitable sweetening agents include, but are not limited to, sucrose, lactose, mannitol, syrups, glycerin, and artificial sweeteners, such as saccharin and aspartame. Suitable emulsifying agents include, but are not limited to, gelatin, acacia, tragacanth, bentonite, and surfactants, such as polyoxyethylene sorbitan monooleate (TWEEN® 20), polyoxyethylene sorbitan monooleate 80 (TWEEN® 80), and triethanolamine oleate. Suitable suspending and dispersing agents include, but are not limited to, sodium carboxymethylcellulose, pectin, tragacanth, Veegum, acacia, sodium carbomethylcellulose, hydroxypropyl methylcellulose, and polyvinylpyrrolidone. Suitable preservatives include, but are not limited to, glycerin, methyl and propylparaben, benzoic add, sodium benzoate and alcohol. Suitable wetting agents include, but are not limited to, propylene glycol monostearate, sorbitan monooleate, diethylene glycol monolaurate, and polyoxyethylene lauryl ether. Suitable solvents include, but are not limited to, glycerin, sorbitol, ethyl alcohol, and syrup. Suitable non-aqueous liquids utilized in emulsions include, but are not limited to, mineral oil and cottonseed oil. Suitable organic acids include, but are not limited to, citric and tartaric acid. Suitable sources of carbon dioxide include, but are not limited to, sodium bicarbonate and sodium carbonate.

It should be understood that many carriers and excipients may serve several functions, even within the same formulation.

In one embodiment, the pharmaceutical compositions provided herein for oral administration can be provided as compressed tablets, tablet triturates, chewable lozenges, rapidly dissolving tablets, multiple compressed tablets, or enteric-coating tablets, sugar-coated, or film-coated tablets. Enteric-coated tablets are compressed tablets coated with substances that resist the action of stomach acid but dissolve or disintegrate in the intestine, thus protecting the active ingredients from the acidic environment of the stomach.

Enteric-coatings include, but are not limited to, fatty acids, fats, phenyl salicylate, waxes, shellac, ammoniated shellac, and cellulose acetate phthalates. Sugar-coated tablets are compressed tablets surrounded by a sugar coating, which may be beneficial in covering up objectionable tastes or odors and in protecting the tablets from oxidation. Film-coated tablets are compressed tablets that are covered with a thin layer or film of a water-soluble material. Film coatings include, but are not limited to, hydroxyethylcellulose, sodium carboxymethylcellulose, polyethylene glycol 4000, and cellulose acetate phthalate. Film coating imparts the same general characteristics as sugar coating. Multiple compressed tablets are compressed tablets made by more than one compression cycle, including layered tablets, and press-coated or dry-coated tablets.

In one embodiment, the tablet dosage forms can be prepared from the active ingredient in powdered, crystalline, or granular forms, alone or in combination with one or more carriers or excipients described herein, including binders, disintegrants, controlled-release polymers, lubricants, diluents, and/or colorants. Flavoring and sweetening agents are especially useful in the formation of chewable tablets and lozenges.

In one embodiment, the pharmaceutical compositions provided herein for oral administration can be provided as soft or hard capsules, which can be made from gelatin, methylcellulose, starch, or calcium alginate. The hard gelatin capsule, also known as the dry-filled capsule (DFC), consists of two sections, one slipping over the other, thus completely enclosing the active ingredient. The soft elastic capsule (SEC) is a soft, globular shell, such as a gelatin shell, which is plasticized by the addition of glycerin, sorbitol, or a similar polyol. The soft gelatin shells may contain a preservative to prevent the growth of microorganisms. Suitable preservatives are those as described herein, including methyl- and propyl-parabens, and sorbic acid. The liquid, semisolid, and solid dosage forms provided herein may be encapsulated in a capsule. Suitable liquid and semisolid dosage forms include solutions and suspensions in propylene carbonate, vegetable oils, or triglycerides. Capsules containing such solutions can be prepared as described in U.S. Pat. Nos. 4,328,245; 4,409,239; and 4,410,545. The capsules may also be coated as known by those of skill in the art in order to modify or sustain dissolution of the active ingredient.

In one embodiment, the pharmaceutical compositions provided herein for oral administration can be provided in liquid and semisolid dosage forms, including emulsions, solutions, suspensions, elixirs, and syrups. An emulsion is a two-phase system, in which one liquid is dispersed in the form of small globules throughout another liquid, which can be oil-in-water or water-in-oil. Emulsions may include a pharmaceutically acceptable non-aqueous liquid or solvent, emulsifying agent, and preservative. Suspensions may include a pharmaceutically acceptable suspending agent and preservative. Aqueous alcoholic solutions may include a pharmaceutically acceptable acetal, such as a di(lower alkyl) acetal of a lower alkyl aldehyde, e.g., acetaldehyde diethyl acetal; and a water-miscible solvent having one or more hydroxyl groups, such as propylene glycol and ethanol. Elixirs are clear, sweetened, and hydroalcoholic solutions. Syrups are concentrated aqueous solutions of a sugar, for example, sucrose, and may also contain a preservative. For a liquid dosage form, for example, a solution in a polyethylene glycol may be diluted with a sufficient quantity of a pharmaceutically acceptable liquid carrier, e.g., water, to be measured conveniently for administration.

In one embodiment, other useful liquid and semisolid dosage forms include, but are not limited to, those containing the active ingredient(s) provided herein, and a dialkylated mono- or poly-alkylene glycol, including, 1,2-dimethoxymethane, diglyme, triglyme, tetraglyme, polyethylene glycol-350-dimethyl ether, polyethylene glycol-550-dimethyl ether, polyethylene glycol-750-dimethyl ether, wherein 350, 550, and 750 refer to the approximate average molecular weight of the polyethylene glycol. These formulations can further comprise one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, bisulfite, sodium metabisulfite, thiodipropionic acid and its esters, and dithiocarbamates.

In one embodiment, the pharmaceutical compositions provided herein for oral administration can be also provided in the forms of liposomes, micelles, microspheres, or nanosystems. Micellar dosage forms can be prepared as described in U.S. Pat. No. 6,350,458.

In one embodiment, the pharmaceutical compositions provided herein for oral administration can be provided as non-effervescent or effervescent, granules and powders, to be reconstituted into a liquid dosage form. Pharmaceutically acceptable carriers and excipients used in the non-effervescent granules or powders may include diluents, sweeteners, and wetting agents. Pharmaceutically acceptable carriers and excipients used in the effervescent granules or powders may include organic acids and a source of carbon dioxide.

In one embodiment, coloring and flavoring agents can be used in all of the above dosage forms.

In one embodiment, the pharmaceutical compositions provided herein for oral administration can be formulated as immediate or modified release dosage forms, including delayed-, sustained, pulsed-, controlled, targeted-, and programmed-release forms.

2. Parenteral Administration

In one embodiment, the pharmaceutical compositions provided herein can be administered parenterally by injection, infusion, or implantation, for local or systemic administration. Parenteral administration, as used herein, include intravenous, intraarterial, intraperitoneal, intrathecal, intraventricular, intraurethral, intrasternal, intracranial, intramuscular, intrasynovial, intravesical, and subcutaneous administration.

In one embodiment, the pharmaceutical compositions provided herein for parenteral administration can be formulated in any dosage forms that are suitable for parenteral administration, including solutions, suspensions, emulsions, micelles, liposomes, microspheres, nanosystems, and solid forms suitable for solutions or suspensions in liquid prior to injection. Such dosage forms can be prepared according to conventional methods known to those skilled in the art of pharmaceutical science (see, e.g., Remington: *The Science and Practice of Pharmacy*, supra).

In one embodiment, the pharmaceutical compositions intended for parenteral administration can include one or more pharmaceutically acceptable carriers and excipients, including, but not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, cryoprotectants, lyoprotectants, thickening agents, pH adjusting agents, and inert gases.

In one embodiment, suitable aqueous vehicles include, but are not limited to, water, saline, physiological saline or phosphate buffered saline (PBS), sodium chloride injection, Ringers injection, isotonic dextrose injection, sterile water injection, dextrose and lactated Ringers injection. Suitable non-aqueous vehicles include, but are not limited to, fixed oils of vegetable origin, castor oil, corn oil, cottonseed oil, olive oil, peanut oil, peppermint oil, safflower oil, sesame oil, soybean oil, hydrogenated vegetable oils, hydrogenated soybean oil, and medium-chain triglycerides of coconut oil, and palm seed oil. Suitable water-miscible vehicles include, but are not limited to, ethanol, 1,3-butanediol, liquid polyethylene glycol (e.g., polyethylene glycol 300 and polyethylene glycol 400), propylene glycol, glycerin, N-methyl-2-pyrrolidone, N,N-dimethylacetamide, and dimethyl sulfoxide.

In one embodiment, suitable antimicrobial agents or preservatives include, but are not limited to, phenols, cresols, mercurials, benzyl alcohol, chlorobutanol, methyl and propyl p-hydroxybenzoates, thimerosal, benzalkonium chloride (e.g., benzethonium chloride), methyl- and propyl-parabens, and sorbic acid. Suitable isotonic agents include, but are not limited to, sodium chloride, glycerin, and dextrose. Suitable buffering agents include, but are not limited to, phosphate and citrate. Suitable antioxidants are those as described herein, including bisulfite and sodium metabisulfite. Suitable local anesthetics include, but are not limited to, procaine hydrochloride. Suitable suspending and dispersing agents are those as described herein, including sodium carboxymethylcelluose, hydroxypropyl methylcellulose, and polyvinylpyrrolidone. Suitable emulsifying agents are those described herein, including polyoxyethylene sorbitan monolaurate, polyoxyethylene sorbitan monooleate 80, and triethanolamine oleate. Suitable sequestering or chelating agents include, but are not limited to EDTA. Suitable pH adjusting agents include, but are not limited to, sodium hydroxide, hydrochloric acid, citric acid, and lactic acid. Suitable complexing agents include, but are not limited to, cyclodextrins, including α-cyclodextrin, β-cyclodextrin, hydroxypropyl-β-cyclodextrin, sulfobutylether-β-cyclodextrin, and sulfobutylether 7-β-cyclodextrin (CAPTISOL®, CyDex, Lenexa, Kans.).

In one embodiment, when the pharmaceutical compositions provided herein are formulated for multiple dosage administration, the multiple dosage parenteral formulations must contain an antimicrobial agent at bacteriostatic or fungistatic concentrations. All parenteral formulations must be sterile, as known and practiced in the art.

In one embodiment, the pharmaceutical compositions for parenteral administration are provided as ready-to-use sterile solutions. In another embodiment, the pharmaceutical compositions are provided as sterile dry soluble products, including lyophilized powders and hypodermic tablets, to be reconstituted with a vehicle prior to use. In yet another embodiment, the pharmaceutical compositions are provided as ready-to-use sterile suspensions. In yet another embodiment, the pharmaceutical compositions are provided as sterile dry insoluble products to be reconstituted with a vehicle prior to use. In still another embodiment, the pharmaceutical compositions are provided as ready-to-use sterile emulsions.

In one embodiment, the pharmaceutical compositions provided herein for parenteral administration can be formulated as immediate or modified release dosage forms, including delayed-, sustained, pulsed-, controlled, targeted-, and programmed-release forms.

In one embodiment, the pharmaceutical compositions provided herein for parenteral administration can be formulated as a suspension, solid, semi-solid, or thixotropic liquid, for administration as an implanted depot. In one embodiment, the pharmaceutical compositions provided herein are dispersed in a solid inner matrix, which is surrounded by an outer polymeric membrane that is insoluble in body fluids but allows the active ingredient in the pharmaceutical compositions diffuse through.

In one embodiment, suitable inner matrixes include, but are not limited to, polymethylmethacrylate, polybutyl-methacrylate, plasticized or unplasticized polyvinylchloride, plasticized nylon, plasticized polyethylene terephthalate, natural rubber, polyisoprene, polyisobutylene, polybutadiene, polyethylene, ethylene-vinyl acetate copolymers, silicone rubbers, polydimethylsiloxanes, silicone carbonate copolymers, hydrophilic polymers, such as hydrogels of esters of acrylic and methacrylic acid, collagen, cross-linked polyvinyl alcohol, and cross-linked partially hydrolyzed polyvinyl acetate.

In one embodiment, suitable outer polymeric membranes include but are not limited to, polyethylene, polypropylene, ethylene/propylene copolymers, ethylene/ethyl acrylate copolymers, ethylene/vinyl acetate copolymers, silicone rubbers, polydimethyl siloxanes, neoprene rubber, chlorinated polyethylene, polyvinylchloride, vinyl chloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer.

3. Topical Administration

In one embodiment, the pharmaceutical compositions provided herein can be administered topically to the skin, orifices, or mucosa. The topical administration, as used herein, includes (intra)dermal, conjunctival, intracorneal, intraocular, ophthalmic, auricular, transdermal, nasal, vaginal, urethral, respiratory, and rectal administration.

In one embodiment, the pharmaceutical compositions provided herein can be formulated in any dosage forms that are suitable for topical administration for local or systemic effect, including emulsions, solutions, suspensions, creams, gels, hydrogels, ointments, dusting powders, dressings, elixirs, lotions, suspensions, tinctures, pastes, foams, films, aerosols, irrigations, sprays, suppositories, bandages, and dermal patches. The topical formulation of the pharmaceutical compositions provided herein can also comprise liposomes, micelles, microspheres, nanosystems, and mixtures thereof.

In one embodiment, pharmaceutically acceptable carriers and excipients suitable for use in the topical formulations provided herein include, but are not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, penetration enhancers, cryoprotectants, lyoprotectants, thickening agents, and inert gases.

In one embodiment, the pharmaceutical compositions can also be administered topically by electroporation, iontophoresis, phonophoresis, sonophoresis, or microneedle or needle-free injection, such as POWDERJECT™ (Chiron Corp., Emeryville, Calif.), and BIOJECT™ (Bioject Medical Technologies Inc., Tualatin, Oreg.).

In one embodiment, the pharmaceutical compositions provided herein can be provided in the forms of ointments, creams, and gels. Suitable ointment vehicles include oleaginous or hydrocarbon vehicles, including lard, benzoinated lard, olive oil, cottonseed oil, and other oils, white petrolatum; emulsifiable or absorption vehicles, such as hydrophilic petrolatum, hydroxystearin sulfate, and anhydrous lanolin; water-removable vehicles, such as hydrophilic ointment; water-soluble ointment vehicles, including polyethylene glycols of varying molecular weight; emulsion vehicles, either water-in-oil (W/O) emulsions or oil-in-water (O/W) emulsions, including cetyl alcohol, glyceryl monostearate, lanolin, and stearic acid (see, e.g., Remington: *The Science and Practice of Pharmacy*, supra). These vehicles are emollient but generally require addition of antioxidants and preservatives.

In one embodiment, suitable cream base can be oil-in-water or water-in-oil. Suitable cream vehicles may be water-washable, and contain an oil phase, an emulsifier, and an aqueous phase. The oil phase is also called the "internal" phase, which is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation may be a nonionic, anionic, cationic, or amphoteric surfactant.

In one embodiment, gels are semisolid, suspension-type systems. Single-phase gels contain organic macromolecules distributed substantially uniformly throughout the liquid carrier. Suitable gelling agents include, but are not limited to, crosslinked acrylic acid polymers, such as carbomers, carboxypolyalkylenes, and CARBOPOL®; hydrophilic polymers, such as polyethylene oxides, polyoxyethylene-polyoxypropylene copolymers, and polyvinylalcohol; cellulosic polymers, such as hydroxypropyl cellulose, hydroxyethyl cellulose, hydroxypropyl methylcellulose, hydroxypropyl methylcellulose phthalate, and methylcellulose; gums, such as tragacanth and xanthan gum; sodium alginate; and gelatin. In order to prepare a uniform gel, dispersing agents such as alcohol or glycerin can be added, or the gelling agent can be dispersed by trituration, mechanical mixing, and/or stirring.

In one embodiment, the pharmaceutical compositions provided herein can be administered rectally, urethrally, vaginally, or perivaginally in the forms of suppositories, pessaries, bougies, poultices or cataplasm, pastes, powders, dressings, creams, plasters, contraceptives, ointments, solutions, emulsions, suspensions, tampons, gels, foams, sprays, or enemas. These dosage forms can be manufactured using conventional processes as described in Remington: *The Science and Practice of Pharmacy*, supra.

In one embodiment, rectal, urethral, and vaginal suppositories are solid bodies for insertion into body orifices, which are solid at ordinary temperatures but melt or soften at body temperature to release the active ingredient(s) inside the orifices. Pharmaceutically acceptable carriers utilized in rectal and vaginal suppositories include bases or vehicles, such as stiffening agents, which produce a melting point in the proximity of body temperature, when formulated with the pharmaceutical compositions provided herein; and antioxidants as described herein, including bisulfite and sodium metabisulfite. Suitable vehicles include, but are not limited to, cocoa butter (theobroma oil), glycerin-gelatin, carbowax (polyoxyethylene glycol), spermaceti, paraffin, white and yellow wax, and appropriate mixtures of mono-, di- and triglycerides of fatty acids, and hydrogels, such as polyvinyl alcohol, hydroxyethyl methacrylate, and polyacrylic acid. Combinations of the various vehicles can also be used. Rectal and vaginal suppositories may be prepared by compressing or molding. The typical weight of a rectal and vaginal suppository is about 2 to about 3 g.

In one embodiment, the pharmaceutical compositions provided herein can be administered ophthalmically in the forms of solutions, suspensions, ointments, emulsions, gel-forming solutions, powders for solutions, gels, ocular inserts, and implants.

In one embodiment, the pharmaceutical compositions provided herein can be administered intranasally or by inhalation to the respiratory tract. The pharmaceutical compositions can be provided in the form of an aerosol or solution for delivery using a pressurized container, pump, spray, atomizer, such as an atomizer using electrohydrodynamics to produce a fine mist, or nebulizer, alone or in combination with a suitable propellant, such as 1,1,1,2-tetrafluoroethane or 1,1,1,2,3,3,3-heptafluoropropane. The pharmaceutical compositions can also be provided as a dry powder for insufflation, alone or in combination with an inert carrier such as lactose or phospholipids; and nasal drops. For intranasal use, the powder can comprise a bioadhesive agent, including chitosan or cyclodextrin.

In one embodiment, solutions or suspensions for use in a pressurized container, pump, spray, atomizer, or nebulizer can be formulated to contain ethanol, aqueous ethanol, or a suitable alternative agent for dispersing, solubilizing, or extending release of the active ingredient provided herein; a propellant as solvent; and/or a surfactant, such as sorbitan trioleate, oleic acid, or an oligolactic acid.

In one embodiment, the pharmaceutical compositions provided herein can be micronized to a size suitable for delivery by inhalation, such as about 50 micrometers or less, or about 10 micrometers or less. Particles of such sizes can be prepared using a comminuting method known to those skilled in the art, such as spiral jet milling, fluid bed jet milling, supercritical fluid processing to form nanoparticles, high pressure homogenization, or spray drying.

In one embodiment, capsules, blisters, and cartridges for use in an inhaler or insufflator can be formulated to contain a powder mix of the pharmaceutical compositions provided herein; a suitable powder base, such as lactose or starch; and a performance modifier, such as l-leucine, mannitol, or magnesium stearate. The lactose may be anhydrous or in the form of the monohydrate. Other suitable excipients or carriers include, but are not limited to, dextran, glucose, maltose, sorbitol, xylitol, fructose, sucrose, and trehalose. The pharmaceutical compositions provided herein for inhaled/intranasal administration can further comprise a suitable flavor, such as menthol and levomenthol; and/or sweeteners, such as saccharin and saccharin sodium.

In one embodiment, the pharmaceutical compositions provided herein for topical administration can be formulated to be immediate release or modified release, including delayed-, sustained-, pulsed-, controlled-, targeted-, and programmed release.

4. Modified Release

In one embodiment, the pharmaceutical compositions provided herein can be formulated as a modified release dosage form. As used herein, the term "modified release" refers to a dosage form in which the rate or place of release of the active ingredient(s) is different from that of an immediate dosage form when administered by the same route. Modified release dosage forms include, but are not limited to, delayed-, extended-, prolonged-, sustained-, pulsatile-, controlled-, accelerated- and fast-, targeted-, programmed-release, and gastric retention dosage forms. The pharmaceutical compositions in modified release dosage forms can be prepared using a variety of modified release devices and methods known to those skilled in the art, including, but not limited to, matrix controlled release devices, osmotic controlled release devices, multiparticulate controlled release devices, ion-exchange resins, enteric coatings, multilayered coatings, microspheres, liposomes, and combinations thereof. The release rate of the active ingredient(s) can also be modified by varying the particle sizes and polymorphism of the active ingredient(s).

Examples of modified release include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,639,480; 5,733,566; 5,739,108; 5,891,474; 5,922,356; 5,972,891; 5,980,945; 5,993,855; 6,045,830; 6,087,324; 6,113,943; 6,197,350; 6,248,363; 6,264,970; 6,267,981; 6,376,461; 6,419,961; 6,589,548; 6,613,358; and 6,699,500.

(a) Matrix Controlled Release Devices

In one embodiment, the pharmaceutical compositions provided herein in a modified release dosage form can be fabricated using a matrix controlled release device known to those skilled in the art (see, e.g., Takada et al. in Encyclopedia of Controlled Drug Delivery, Vol. 2, Mathiowitz Ed., Wiley, 1999).

In certain embodiments, the pharmaceutical compositions provided herein in a modified release dosage form is formulated using an erodible matrix device, which is water-swellable, erodible, or soluble polymers, including, but not limited to, synthetic polymers, and naturally occurring polymers and derivatives, such as polysaccharides and proteins.

In one embodiment, materials useful in forming an erodible matrix include, but are not limited to, chitin, chitosan, dextran, and pullulan; gum agar, gum arabic, gum karaya, locust bean gum, gum tragacanth, carrageenans, gum ghatti, guar gum, xanthan gum, and scleroglucan; starches such as dextrin and maltodextrin; hydrophilic colloids, such as pectin; phosphatides, such as lecithin; alginates; propylene glycol alginate; gelatin; collagen; cellulosics, such as ethyl cellulose (EC), methylethyl cellulose (MEC), carboxymethyl cellulose (CMC), CMEC, hydroxyethyl cellulose (HEC), hydroxypropyl cellulose (HPC), cellulose acetate (CA), cellulose propionate (CP), cellulose butyrate (CB), cellulose acetate butyrate (CAB), CAP, CAT, hydroxypropyl methyl cellulose (HPMC), HPMCP, HPMCAS, hydroxypropyl methyl cellulose acetate trimellitate (HPMCAT), and ethyl hydroxyethyl cellulose (EHEC); polyvinyl pyrrolidone; polyvinyl alcohol; polyvinyl acetate; glycerol fatty acid esters; polyacrylamide; polyacrylic acid; copolymers of ethacrylic acid or methacrylic acid (EUDRAGIT®, Rohm America, Inc., Piscataway, N.J.); poly(2-hydroxyethyl-methacrylate); polylactides; copolymers of L-glutamic acid and ethyl-L-glutamate; degradable lactic acid-glycolic acid copolymers; poly-D-(–)-3-hydroxybutyric acid; and other acrylic acid derivatives, such as homopolymers and copolymers of butylmethacrylate, methyl methacrylate, ethyl methacrylate, ethylacrylate, (2-dimethylaminoethyl)methacrylate, and (trimethylaminoethyl)methacrylate chloride.

In certain embodiments, the pharmaceutical compositions provided herein are formulated with a non-erodible matrix device. The active ingredient(s) is dissolved or dispersed in an inert matrix and is released primarily by diffusion through the inert matrix once administered. Materials suitable for use as a non-erodible matrix device include, but are not limited to, insoluble plastics, such as polyethylene, polypropylene, polyisoprene, polyisobutylene, polybutadiene, polymethylmethacrylate, polybutylmethacrylate, chlorinated polyethylene, polyvinylchloride, methyl acrylate-methyl methacrylate copolymers, ethylene-vinyl acetate copolymers, ethylene/propylene copolymers, ethylene/ethyl acrylate copolymers, vinyl chloride copolymers with vinyl acetate, vinylidene chloride, ethylene and propylene, ionomer polyethylene terephthalate, butyl rubbers, epichlorohydrin rubbers, ethylene/vinyl alcohol copolymer, ethylene/vinyl acetate/vinyl alcohol terpolymer, ethylene/vinyloxyethanol copolymer, polyvinyl chloride, plasticized nylon, plasticized polyethylene terephthalate, natural rubber, silicone rubbers, polydimethylsiloxanes, and silicone carbonate copolymers; hydrophilic polymers, such as ethyl cellulose, cellulose acetate, crospovidone, and cross-linked partially hydrolyzed polyvinyl acetate; and fatty compounds, such as carnauba wax, microcrystalline wax, and triglycerides.

In one embodiment, in a matrix controlled release system, the desired release kinetics can be controlled, for example, via the polymer type employed, the polymer viscosity, the particle sizes of the polymer and/or the active ingredient(s), the ratio of the active ingredient(s) versus the polymer, and other excipients or carriers in the compositions.

In one embodiment, the pharmaceutical compositions provided herein in a modified release dosage form can be prepared by methods known to those skilled in the art, including direct compression, dry or wet granulation followed by compression, and melt-granulation followed by compression.

(b) Osmotic Controlled Release Devices

In one embodiment, the pharmaceutical compositions provided herein in a modified release dosage form can be fabricated using an osmotic controlled release device, including, but not limited to, one-chamber system, two-chamber system, asymmetric membrane technology (AMT), and extruding core system (ECS). In general, such devices have at least two components: (a) a core which contains an active ingredient; and (b) a semipermeable membrane with at least one delivery port, which encapsulates the core. The semipermeable membrane controls the influx of water to the core from an aqueous environment of use so as to cause drug release by extrusion through the delivery port(s).

In one embodiment, in addition to the active ingredient(s), the core of the osmotic device optionally includes an osmotic agent, which creates a driving force for transport of water from the environment of use into the core of the device. One class of osmotic agents is water-swellable hydrophilic polymers, which are also referred to as "osmopolymers" and "hydrogels." Suitable water-swellable hydrophilic polymers as osmotic agents include, but are not limited to, hydrophilic vinyl and acrylic polymers, polysaccharides such as calcium alginate, polyethylene oxide (PEO), polyethylene glycol (PEG), polypropylene glycol (PPG), poly(2-hydroxyethyl methacrylate), poly(acrylic) acid, poly(methacrylic) acid, polyvinylpyrrolidone (PVP), crosslinked PVP, polyvinyl alcohol (PVA), PVA/PVP copolymers, PVA/PVP copolymers with hydrophobic monomers such as methyl methacrylate and vinyl acetate, hydrophilic polyurethanes containing large PEO blocks, sodium croscarmellose, carrageenan, hydroxyethyl cellulose (HEC), hydroxypropyl cellulose (HPC), hydroxypropyl methyl cellulose (HPMC), carboxymethyl cellulose (CMC) and carboxyethyl, cellulose (CEC), sodium alginate, polycarbophil, gelatin, xanthan gum, and sodium starch glycolate.

In one embodiment, the other class of osmotic agents is osmogens, which are capable of imbibing water to affect an osmotic pressure gradient across the barrier of the surrounding coating. Suitable osmogens include, but are not limited to, inorganic salts, such as magnesium sulfate, magnesium chloride, calcium chloride, sodium chloride, lithium chloride, potassium sulfate, potassium phosphates, sodium carbonate, sodium sulfite, lithium sulfate, potassium chloride, and sodium sulfate; sugars, such as dextrose, fructose, glucose, inositol, lactose, maltose, mannitol, raffinose, sorbitol, sucrose, trehalose, and xylitol; organic acids, such as ascorbic acid, benzoic acid, fumaric acid, citric acid, maleic acid, sebacic acid, sorbic acid, adipic acid, edetic acid, glutamic acid, p-toluenesulfonic acid, succinic acid, and tartaric acid; urea; and mixtures thereof In one embodiment, osmotic agents of different dissolution rates can be employed to influence how rapidly the active ingredient(s) is initially delivered from the dosage form. For example, amorphous sugars, such as MANNOGEM™ EZ (SPI Pharma, Lewes, Del.) can be used to provide faster delivery during the first couple of hours to promptly produce the desired therapeutic effect, and gradually and continually release of the remaining amount to maintain the desired level of therapeutic or prophylactic effect over an extended period of time. In this case, the active ingredient(s) is released at such a rate to replace the amount of the active ingredient metabolized and excreted.

In one embodiment, the core can also include a wide variety of other excipients and carriers as described herein to enhance the performance of the dosage form or to promote stability or processing.

In one embodiment, materials useful in forming the semipermeable membrane include various grades of acrylics, vinyls, ethers, polyamides, polyesters, and cellulosic derivatives that are water-permeable and water-insoluble at physiologically relevant pHs, or are susceptible to being rendered water-insoluble by chemical alteration, such as crosslinking Examples of suitable polymers useful in forming the coating, include plasticized, unplasticized, and reinforced cellulose acetate (CA), cellulose diacetate, cellulose triacetate, CA propionate, cellulose nitrate, cellulose acetate butyrate (CAB), CA ethyl carbamate, CAP, CA methyl carbamate, CA succinate, cellulose acetate trimellitate (CAT), CA dimethylaminoacetate, CA ethyl carbonate, CA chloroacetate, CA ethyl oxalate, CA methyl sulfonate, CA butyl sulfonate, CA p-toluene sulfonate, agar acetate, amylose triacetate, beta glucan acetate, beta glucan triacetate, acetaldehyde dimethyl acetate, triacetate of locust bean gum, hydroxylated ethylene-vinylacetate, EC, PEG, PPG, PEG/PPG copolymers, PVP, HEC, HPC, CMC, CMEC, HPMC, HPMCP, HPMCAS, HPMCAT, poly(acrylic) acids and esters and poly-(methacrylic) acids and esters and copolymers thereof, starch, dextran, dextrin, chitosan, collagen, gelatin, polyalkenes, polyethers, polysulfones, polyethersulfones, polystyrenes, polyvinyl halides, polyvinyl esters and ethers, natural waxes, and synthetic waxes.

In one embodiment, semipermeable membrane can also be a hydrophobic microporous membrane, wherein the pores are substantially filled with a gas and are not wetted by the aqueous medium but are permeable to water vapor, as disclosed in U.S. Pat. No. 5,798,119. Such hydrophobic but water-vapor permeable membrane are typically composed of hydrophobic polymers such as polyalkenes, polyethylene, polypropylene, polytetrafluoroethylene, polyacrylic acid derivatives, polyethers, polysulfones, polyethersulfones, polystyrenes, polyvinyl halides, polyvinylidene fluoride, polyvinyl esters and ethers, natural waxes, and synthetic waxes.

In one embodiment, the delivery port(s) on the semipermeable membrane can be formed post-coating by mechanical or laser drilling. Delivery port(s) can also be formed in situ by erosion of a plug of water-soluble material or by rupture of a thinner portion of the membrane over an indentation in the core. In addition, delivery ports can be formed during coating process, as in the case of asymmetric membrane coatings of the type disclosed in U.S. Pat. Nos. 5,612,059 and 5,698,220.

In one embodiment, the total amount of the active ingredient(s) released and the release rate can substantially by modulated via the thickness and porosity of the semipermeable membrane, the composition of the core, and the number, size, and position of the delivery ports.

In one embodiment, the pharmaceutical compositions in an osmotic controlled-release dosage form can further comprise additional conventional excipients or carriers as described herein to promote performance or processing of the formulation.

In one embodiment, the osmotic controlled-release dosage forms can be prepared according to conventional methods and techniques known to those skilled in the art (see, e.g., Remington: *The Science and Practice of Pharmacy*, supra; Santus & Baker, *J. Controlled Release* 1995, 35, 1-21; Verma et al., *Drug Development and Industrial Pharmacy* 2000, 26, 695-708; Verma et al., *J. Controlled Release* 2002, 79, 7-27).

In certain embodiments, the pharmaceutical compositions provided herein are formulated as AMT controlled-release dosage form, which comprises an asymmetric osmotic membrane that coats a core comprising the active ingredient(s) and other pharmaceutically acceptable excipients or carriers. See, e.g., U.S. Pat. No. 5,612,059 and WO 2002/17918. The AMT controlled-release dosage forms can be prepared according to conventional methods and techniques known to those skilled in the art, including direct compression, dry granulation, wet granulation, and a dip-coating method.

In certain embodiments, the pharmaceutical compositions provided herein are formulated as ESC controlled-release dosage form, which comprises an osmotic membrane that coats a core comprising the active ingredient(s), a hydroxylethyl cellulose, and other pharmaceutically acceptable excipients or carriers.

(c) Multiparticulate Controlled Release Devices

In one embodiment, the pharmaceutical compositions provided herein in a modified release dosage form can be fabricated as a multiparticulate controlled release device, which comprises a multiplicity of particles, granules, or pellets, ranging from about 10 µm to about 3 mm, about 50 µm to about 2.5 mm, or from about 100 µm to about 1 mm in diameter. Such multiparticulates can be made by the processes known to those skilled in the art, including wet- and dry-granulation, extrusion/spheronization, roller-compaction, melt-congealing, and by spray-coating seed cores. See, e.g., *Multiparticulate Oral Drug Delivery*; Marcel Dekker: 1994; *Pharmaceutical Pelletization Technology*; Marcel Dekker: 1989.

In one embodiment, other excipients or carriers as described herein can be blended with the pharmaceutical compositions to aid in processing and forming the multiparticulates. The resulting particles can themselves constitute the multiparticulate device or can be coated by various film-forming materials, such as enteric polymers, water-swellable, and water-soluble polymers. The multiparticulates can be further processed as a capsule or a tablet.

(d) Targeted Delivery

In one embodiment, the pharmaceutical compositions provided herein can also be formulated to be targeted to a particular tissue, receptor, or other area of the body of the subject to be treated, including liposome-, resealed erythrocyte-, and antibody-based delivery systems. Examples include, but are not limited to, those disclosed in U.S. Pat. Nos. 6,316,652; 6,274,552; 6,271,359; 6,253,872; 6,139,865; 6,131,570; 6,120,751; 6,071,495; 6,060,082; 6,048,736; 6,039,975; 6,004,534; 5,985,307; 5,972,366; 5,900,252; 5,840,674; 5,759,542; and 5,709,874.

(e) Targeted Delivery with Special Carriers

In one embodiment, the pharmaceutical compositions provided herein can also be formulated or engineered to be bound to a particular carrier, including but not limited to albumin, PEG (polyethylene glycol), PEGylated albumin polymers, PG (poly(l-glutamic acid)) polymers and such as to form polymer-drug conjugates. Examples include, but are not limited to, those disclosed in U.S. Pat. Nos. 5,977,163; 5,648,506; 6,703,417; 5,439,686; 5,498,421; 6,096,331; 6,506,405; 6,537,579; 6,749,868; 6,753,006; 7,820,788; 7,923,536; 8,034,375; 8,138,229; 8,268,348; and 8,314,156 each of which is incorporated herein by reference.

5. Kits

In one embodiment, provided herein are kits which, when used by the medical practitioner, can simplify the administration of appropriate amounts of active ingredients to a subject. In certain embodiments, the kit provided herein includes a container and a dosage form of a compound provided herein, including a single enantiomer or a mixture of enantiomers or diastereomers thereof; or a pharmaceutically acceptable salt, solvate, or prodrug thereof In certain embodiments, the kit includes a container comprising a dosage form of the compound provided herein, including a single enantiomer or a mixture of enantiomers or diastereomers thereof; or a pharmaceutically acceptable salt, solvate, or prodrug thereof, in a container comprising one or more other therapeutic agent(s) described herein.

In one embodiment, active ingredients provided herein are not administered to a patient at the same time or by the same route of administration. In another embodiment, provided are kits which can simplify the administration of appropriate amounts of active ingredients.

In one embodiment, a kit comprises a dosage form of a compound provided herein. Kits can further comprise one or more second active ingredients as described herein, or a pharmacologically active mutant or derivative thereof, or a combination thereof In other embodiments, kits can further comprise devices that are used to administer the active ingredients. Examples of such devices include, but are not limited to, syringes, drip bags, patches, and inhalers.

In one embodiment, kits can further comprise cells or blood for transplantation as well as pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

In one embodiment, the compounds provided herein can also be provided as an article of manufacture using packaging materials well known to those of skill in the art. See, e.g., U.S. Pat. Nos. 5,323,907; 5,052,558; and 5,033,252. Examples of pharmaceutical packaging materials include, but are not limited to, blister packs, bottles, tubes, inhalers, pumps, bags, vials, containers, syringes, and any packaging material suitable for a selected formulation and intended mode of administration and treatment.

E. METHODS OF USE

1. In Vitro Assays and In Vivo Assays

In one embodiment, provided herein is a method of inhibiting or reducing the activity of eIF4E. In one embodiment, provided herein is a method of downregulating protein translation initiation with a compound provided herein, e.g., a compound of formula (I). In one embodiment, without being limited by a particular theory, the method comprises contacting a compound provided herein, e.g., a compound of formula (I), with one or more molecular targets in the translation initiation complex eIF4F, which comprises eIF4E, eIF4G (a scaffold protein), and eIF4A (an RNA helicase). In one embodiment, without being limited by a particular theory, the method comprises disrupting the interaction between eIF4E and the 7-methylguanosine 5' cap with a compound provided herein, e.g., a compound of formula (I). In one embodiment, the method provided herein comprises selectively downregulating protein translation initiation with a compound provided herein, e.g., a compound of formula (I). In one embodiment, the compound provided herein has minimal on-target toxicity. In one embodiment, the compound provided herein has a large therapeutic index. In one embodiment, the compound provided herein inhibits cancer growth while having minimal toxicity in normal cells.

In one embodiment, the compound selectively targets the protein translation pathway. In one embodiment, without being limited by a particular theory, the compound selectively disrupts the eIF4F complex.

In one embodiment, provided herein are methods comprising the step of contacting a compound provided herein with one or more cells of a certain type of fibrosis including but not limited to organ specific fibrosis (heart, liver, lung, kidney, bone marrow, skin, pancreas), other forms of fibrosis (retroperitoneal, nephrogenic, and cystic), and connective tissue disorders (atherosclerosis, cirrhosis, scleroderma, keloids, Crohn's disease, and endometriosis). In one embodiment, provided herein are methods comprising the step of contacting a compound provided herein with one or more cells of a certain type of cancer, including but not limited to, metastatic cancer, breast cancer (e.g., triple negative breast cancer, ER+ breast cancer, or ER− breast cancer), basal cell carcinoma, skin cancer, lung cancer, small cell lung cancer, non-small cell lung cancer, brain cancer, medulloblastoma, glioblastoma, colorectal cancer, ovarian cancer, liver cancer, pancreatic cancer (e.g., carcinoma, angiosarcoma, adenosarcoma), gastric cancer, gastroesophageal junction cancer, prostate cancer, cervical cancer, bladder cancer, head and neck cancer, lymphoma (e.g., mantle cell lymphoma, diffuse large B-cell lymphoma), solid tumors that cannot be removed by surgery, locally advanced solid tumors, metastatic solid tumors, leukemia (e.g., acute myeloid leukemia (AML), acute lymphoblastic leukemia (ALL), or chronic myeloid leukemia (CML)), or recurrent or refractory tumors. In one embodiment, provided herein are methods comprising the step of contacting a compound provided herein with one or more cells of a certain type of disorder, including but not limited to, basal cell nevus syndrome (Gorlin syndrome). In one embodiment, provided herein are methods comprising the step of contacting a compound provided herein with one or more cells of a certain type of disorder, including but not limited to, basal cell carcinoma associated with Gorlin syndrome. In certain embodiments, the methods may be conducted in vivo, in vitro, and/or ex vivo. In certain embodiments, the methods may be conducted in an animal, e.g., mice or rats. In certain embodiments, the methods provided herein further comprise the step of implanting a certain cancer cell type (e.g., breast cancer) in an animal (e.g., mice or rats) using a method known in the art, followed by the step of treating the animal with a compound provided herein. The time between the implanting step and the treatment step may vary to allow the establishment and/or metastasis of cancer in the animal.

In one embodiment, the compound provided herein modulates secreted cytokines from activated peripheral blood mononuclear cells (PBMCs) and augments cytotoxicity in certain cancer cell lines, including, but not limited to, MDA-MB-468 (triple negative breast cancer), XPA-1 (pancreatic cancer), and Panc-1 (pancreatic cancer).

In one embodiment, provided herein is a method of inhibiting or reducing the activity of cancer associated fibroblasts in the tumor stroma. In one embodiment, the compound provided herein inhibits or reduces alpha-smooth muscle actin.

In one embodiment, the cells are sensitive to a compound provided herein, e.g., a compound of formula (I), or an enantiomer, a mixture of enantiomers or a mixture of diastereomers thereof, wherein the $EC_{50}$ of the compound is less than about 0.001 µM, less than about 0.005 µM, less than about 0.01 µM, less than about 0.05 µM, less than about 0.1 µM, less than about 0.3 µM, less than about 0.5 µM, less than about 0.7 µM, less than about 1 µM, less than about 3 µM, less than about 5 µM, less than about 10 µM, less than about 15 µM, or less than about 30 µM. In one embodiment, the cells are sensitive to a compound provided herein, e.g., a compound of formula (I), or an enantiomer, a mixture of enantiomers or a mixture of diastereomers thereof, where the $EC_{50}$ of the compound is between about 0.001 µM and about 30 µM, between about 0.01 µM and about 30 µM, between about 0.1 µM and about 30 µM, between about 1 µM and about 30 µM, between about 3 µM and about 30 µM, or between about 10 µM and about 30 µM. In one embodiment, the cells are sensitive to a compound provided herein, e.g., a compound of formula (I), or an enantiomer, a mixture of enantiomers or a mixture of diastereomers thereof, wherein the $EC_{50}$ of the compound is about 0.001 µM, about 0.005 µM, about 0.01 µM, about 0.05 µM, about 0.1 µM, about 0.3 µM, about 0.5 µM, about 0.7 µM, about 1 µM, about 3 µM, about 5 µM, about 10 µM, about 15 µM, about 30 µM, or greater than 30 µM.

2. Treatment, Prevention, and/or Amelioration of Disorders

In one embodiment, provided herein is a method of treating, preventing, or ameliorating one or more symptoms of a disorder mediated by protein translation, comprising administering a compound provided herein, e.g., a compound of formula (I), or an enantiomer, a mixture of enantiomers, or a mixture of two or more diastereomers thereof, or a pharmaceutically acceptable salt, solvate, hydrate, or prodrug thereof, or a pharmaceutical composition provided herein. In one embodiment, provided herein is a method of treating, preventing, or ameliorating one or more symptoms of a disorder mediated by eIF4E, comprising administering a compound provided herein, e.g., a compound of formula (I), or an enantiomer, a mixture of enantiomers, or a mixture of two or more diastereomers thereof, or a pharmaceutically acceptable salt, solvate, hydrate, or prodrug thereof, or a pharmaceutical composition provided herein. In one embodiment, the disorder is cancer, a proliferative disorder, breast cancer, triple negative breast cancer, ER+ breast cancer, ER− breast cancer, basal cell nevus syndrome (Gorlin syndrome), basal cell carcinoma, skin cancer, lung cancer, small cell lung cancer, non-small cell lung cancer, brain cancer, medulloblastoma, glioblastoma, colorectal cancer, ovarian cancer, liver cancer, pancreatic cancer, pancreatic carcinoma, pancreatic angiosarcoma, pancreatic adenosarcoma, gastric cancer, gastroesophageal junction cancer, prostate cancer, cervical cancer, bladder cancer, head and neck cancer, lymphoma, mantle cell lymphoma, diffuse large B-cell lymphoma, solid tumors that cannot be removed by surgery, locally advanced solid tumors, metastatic solid tumors, leukemia, acute myeloid leukemia (AML), acute lymphoblastic leukemia (ALL), chronic myeloid leukemia (CML), or recurrent or refractory tumors. In one embodiment, the disorder is basal cell carcinoma associated with Gorlin syndrome.

In one embodiment, provided herein is a method for the treatment, prevention, or amelioration of one or more symptoms of a disorder, such as cancer, a proliferative disorder, or a disorder mediated by angiogenesis, in a subject, comprising administering to the subject a therapeutically effective amount of a compound provided herein, e.g., a compound of formula (I), or an enantiomer, a mixture of enantiomers or a mixture of diasteromers thereof, or a pharmaceutically acceptable salt, solvate, hydrate or prodrug thereof. In one embodiment, the subject is a human. In one embodiment, the subject is a mammal. In one embodiment, the subject is a rodent, such as, e.g., mice or rats. In one embodiment, the subject is a primate. In one embodiment, the subject is a non-human primate, a farm animal such as cattle, a sport animal such as horses, or a pet such as dogs or cats.

In one embodiment, provided herein is use of a compound, e.g., a compound of formula (I), or an enantiomer, a mixture of enantiomers or a mixture of diastereomers thereof, or a pharmaceutically acceptable salt, solvate, hydrate or prodrug thereof, or a pharmaceutical composition comprising the compound, in the manufacture of a medicament for the treatment, prevention, or amelioration of a disorder provided herein. In one embodiment, provided herein is a compound, e.g., a compound of formula (I), or an enantiomer, a mixture of enantiomers or a mixture of diastereomers thereof, or a pharmaceutically acceptable salt, solvate, hydrate or prodrug thereof, or a pharmaceutical composition comprising the compound, for use in the treatment, prevention, or amelioration of a disorder provided herein. In one embodiment, the disorder is cancer. In one embodiment, the disorder is a proliferative disorder. In one embodiment, provided herein is use of a compound, e.g., a compound of formula (I), or an enantiomer, a mixture of enantiomers or a mixture of diastereomers thereof, or a pharmaceutically acceptable salt, solvate, hydrate or prodrug thereof, or a pharmaceutical composition comprising the compound, in the manufacture of a medicament for the treatment of cancer.

In one embodiment, the disorder that can be treated, prevented, or ameliorated is a disorder, disease, or condition associated with eIF4E levels in a subject, comprising administering to the subject a therapeutically effective amount of a compound provided herein, e.g., a compound of formula (I), or an enantiomer, a mixture of enantiomers or a mixture of diastereomers thereof, or a pharmaceutically acceptable salt, solvate, hydrate or prodrug thereof. In one embodiment, the disorder that can be treated, prevented, or ameliorated is a disorder, disease, or condition associated with protein translation initiation in a subject, comprising administering to the subject a therapeutically effective amount of a compound provided herein, e.g., a compound of formula (I), or an enantiomer, a mixture of enantiomers or a mixture of diastereomers thereof, or a pharmaceutically acceptable salt, solvate, hydrate or prodrug thereof. In one embodiment, the disorder that can be treated, prevented, or ameliorated is a disorder, disease, or condition responsive to the modulation of eIF4E levels in a subject, comprising administering to the subject a therapeutically effective amount of a compound provided herein, e.g., a compound of formula (I), or an enantiomer, a mixture of enantiomers or a mixture of diastereomers thereof, or a pharmaceutically acceptable salt, solvate, hydrate or prodrug thereof. In one embodiment, the disorder that can be treated, prevented, or ameliorated is a disorder, disease, or condition mediated by eIF4F complex in a subject, comprising administering to the subject a therapeutically effective amount of a compound provided herein, e.g., a compound of formula (I), or an enantiomer, a mixture of enantiomers or a mixture of diastereomers thereof, or a pharmaceutically acceptable salt, solvate, hydrate or prodrug thereof In one embodiment, the disorder that can be treated, prevented, or ameliorated is cancer or a proliferative disorder, including but not limited to, breast cancer (e.g., triple negative breast cancer, ER+ breast cancer, or ER− breast cancer), basal cell carcinoma, skin cancer, lung cancer, small cell lung cancer, non-small cell lung cancer, brain cancer, medulloblastoma, glioblastoma, colorectal cancer, ovarian cancer, liver cancer, pancreatic cancer (e.g., carcinoma, angiosarcoma, adenosarcoma), gastric cancer, gastroesophageal junction cancer, prostate cancer, cervical cancer, bladder cancer, head and neck cancer, lymphoma (e.g., mantle cell lymphoma, diffuse large B-cell lymphoma), solid tumors that cannot be removed by surgery, locally advanced solid tumors, metastatic solid tumors, leukemia (e.g., acute myeloid leukemia (AML), acute lymphoblastic leukemia (ALL), or chronic myeloid leukemia (CML)), or recurrent or refractory tumors. In one embodiment, the disorder that can be treated, prevented, or ameliorated includes, but is not limited to, basal cell nevus syndrome (Gorlin syndrome). In one embodiment, the disorder that can be treated, prevented, or ameliorated includes, but is not limited to, basal cell carcinoma associated with Gorlin syndrome.

In one embodiment, the compounds provided herein inhibit angiogenesis and are useful in the treatment of diseases or conditions mediated by angiogenesis. In one embodiment, the compounds provided herein are useful for treating tumors, e.g., solid tumors, such as, e.g., colon, lung, pancreatic, ovarian, breast and glioma. In one embodiment, the compounds provided herein are useful for treating macular degeneration, such as, e.g., wet age-related macular degeneration. In one embodiment, the compounds provided herein are useful for treating inflammatory/immune diseases, such as, e.g., Crohn's disease, inflammatory bowel disease, Sjogren's syndrome, asthma, organ transplant rejection, systemic lupus erythmatoses, rheumatoid arthritis, psoriatic arthritis, psoriasis, and multiple sclerosis. In one embodiment, the compounds provided herein are useful as a depilatory.

In one embodiment, the method provided herein comprises the step of identifying in a subject the presence of a certain type of cancer. In one embodiment, the method provided herein comprises the step of identifying in a subject the presence of a type of cancer that is sensitive to eIF4E modulation. In one embodiment, the method provided herein comprises the step of administering a compound provided herein, e.g., a compound of formula (I), or an enantiomer, a mixture of enantiomers or a mixture of diastereomers thereof, or a pharmaceutically acceptable salt, solvate, hydrate or prodrug thereof, to a subject having a certain type of cancer.

In one embodiment, provided herein are methods of treating, preventing, or ameliorating cancer in the primary tumor, in the lymph nodes, and/or after distant metastasis, comprising administering a compound provided herein, e.g., a compound of formula (I), or an enantiomer, a mixture of enantiomers or a mixture of diastereomers thereof, or a pharmaceutically acceptable salt, solvate, hydrate or prodrug thereof, to a subject in need thereof. In one embodiment, provided herein are methods of treating, preventing, or ameliorating cancer in the primary tumor, comprising administering a compound provided herein, e.g., a compound of formula (I), or an enantiomer, a mixture of enantiomers or a mixture of diastereomers thereof, or a pharmaceutically acceptable salt, solvate, hydrate or prodrug thereof, to a subject in need thereof. In one embodiment, provided herein are methods of preventing metastasis comprising administering a compound provided herein, e.g., a compound of formula (I), or an enantiomer, a mixture of enantiomers or a mixture of diastereomers thereof, or a pharmaceutically acceptable salt, solvate, hydrate or prodrug thereof, to a subject in need thereof. In one embodiment, provided herein are methods of treating, preventing, or ameliorating cancer in the lymph nodes, comprising administering a compound provided herein, e.g., a compound of formula (I), or an enantiomer, a mixture of enantiomers or a mixture of diastereomers thereof, or a pharmaceutically acceptable salt, solvate, hydrate or prodrug thereof, to a subject in need thereof. In one embodiment, provided herein are methods of treating, preventing, or ameliorating cancer after distant metastasis, comprising administering a compound provided herein, e.g., a compound of formula (I), or an enantiomer, a mixture of enantiomers or a mixture of diastereomers thereof, or a pharmaceutically acceptable salt, solvate, hydrate or prodrug thereof, to a subject in need thereof.

In one embodiment, provided herein are methods of treating, preventing, or ameliorating cancer in a subject having surgically resectable cancer, locally advanced cancer, regionally advanced cancer, and/or distant metastatic cancer, comprising administering a compound provided herein, e.g., a compound of formula (I), or an enantiomer, a mixture of enantiomers or a mixture of diastereomers thereof, or a pharmaceutically acceptable salt, solvate, hydrate or prodrug thereof, to a subject in need thereof. In one embodiment, provided herein are methods of treating, preventing, or ameliorating cancer in a subject having surgically resectable cancer, comprising administering a compound provided herein, e.g., a compound of formula (I), or an enantiomer, a mixture of enantiomers or a mixture of diastereomers thereof, or a pharmaceutically acceptable salt, solvate, hydrate or prodrug thereof, to a subject in need thereof. In one embodiment, provided herein are methods of treating, preventing, or ameliorating cancer in a subject having locally advanced cancer, comprising administering a compound provided herein, e.g., a compound of formula (I), or an enantiomer, a mixture of enantiomers or a mixture of diastereomers thereof, or a pharmaceutically acceptable salt, solvate, hydrate or prodrug thereof, to a subject in need thereof. In one embodiment, provided herein are methods of treating, preventing, or ameliorating cancer in a subject having regionally advanced cancer, comprising administering a compound provided herein, e.g., a compound of formula (I), or an enantiomer, a mixture of enantiomers or a mixture of diastereomers thereof, or a pharmaceutically acceptable salt, solvate, hydrate or prodrug thereof, to a subject in need thereof. In one embodiment, provided herein are methods of treating, preventing, or ameliorating cancer in a subject having distant metastatic cancer, comprising administering a compound provided herein, e.g., a compound of formula (I), or an enantiomer, a mixture of enantiomers or a mixture of diastereomers thereof, or a pharmaceutically acceptable salt, solvate, hydrate or prodrug thereof, to a subject in need thereof.

In one embodiment, provided herein are methods of treating, preventing, or ameliorating breast cancer comprising administering a compound provided herein, e.g., a compound of formula (I), or an enantiomer, a mixture of enantiomers or a mixture of diastereomers thereof, or a pharmaceutically acceptable salt, solvate, hydrate or prodrug thereof, to a subject having breast cancer. In one embodiment, provided herein is a method of treating, preventing, or ameliorating triple negative breast cancer comprising administering a compound provided herein, e.g., a compound of formula (I), or an enantiomer, a mixture of enantiomers or a mixture of diastereomers thereof, or a pharmaceutically acceptable salt, solvate, hydrate or prodrug thereof.

In one embodiment, provided herein are methods of treating, preventing, or ameliorating certain stages of breast cancer, including but not limited to, Stage 0, Stage I, Stage IIA, Stage IIB, Stage IIIA, Stage IIIB, Stage IIIC, and Stage IV, by administering a compound provided herein, e.g., a compound of formula (I), or an enantiomer, a mixture of enantiomers or a mixture of diastereomers thereof, or a pharmaceutically acceptable salt, solvate, hydrate or prodrug thereof, to a subject in need thereof. The staging of breast cancer may be defined according to methods known in the art, for example, according to the guidelines provided by the American Joint Committee on Cancer (AJCC). In one embodiment, the staging of breast cancer is designated and grouped based on the TNM classification, i.e., a classification based on the status of primary tumor (e.g., TX, T0, T1s, T1, T2, T3, T4), regional lymph nodes (e.g., NX, N0, N1, N2, N3), and/or distant metastasis (e.g., MX, M0, M1), in a subject having breast cancer. See, e.g., Breast in: American Joint Committee on Cancer: AJCC Cancer Staging Manual, 6th ed., New York, N.Y., Springer, 2002, 171-80.

In one embodiment, provided herein are methods for treating subjects having breast cancer, including, e.g., particular breast cancer subtypes, using a compound provided herein, e.g., a compound of formula (I), or an enantiomer, a mixture of enantiomers or a mixture of diastereomers thereof, or a pharmaceutically acceptable salt, solvate, hydrate or prodrug thereof. In one embodiment, the tumor is estrogen receptor-negative, progesterone receptor-negative and HER2-negative. In one embodiment, provided herein are methods comprising the step of identifying in a subject the presence of a particular type of breast cancer, including e.g., triple negative breast cancer, and the step of administering a compound provided herein, e.g., a compound of formula (I), or an enantiomer, a mixture of enantiomers or a mixture of diastereomers thereof, or a pharmaceutically acceptable salt, solvate, hydrate or prodrug thereof, to the subject.

In one embodiment, the disorders, diseases, or conditions treatable with a compound provided herein, include, but are not limited to, (1) inflammatory or allergic diseases, including systemic anaphylaxis and hypersensitivity disorders, atopic dermatitis, urticaria, drug allergies, insect sting allergies, food allergies (including celiac disease and the like), and mastocytosis; (2) inflammatory bowel diseases, including Crohn's disease, ulcerative colitis, ileitis, and enteritis; (3) vasculitis, and Behcet's syndrome; (4) psoriasis and inflammatory dermatoses, including dermatitis, eczema, atopic dermatitis, allergic contact dermatitis, urticaria, viral cutaneous pathologies including those derived from human papillomavirus, HIV or RLV infection, bacterial, flugal, and other parasital cutaneous pathologies, and cutaneous lupus erythematosus; (5) asthma and respiratory allergic diseases, including allergic asthma, exercise induced asthma, allergic rhinitis, otitis media, allergic conjunctivitis, hypersensitivity lung diseases, and chronic obstructive pulmonary disease; (6) autoimmune diseases, including arthritis (including rheumatoid and psoriatic), systemic lupus erythematosus, type I diabetes, myasthenia gravis, multiple sclerosis, Graves' disease, and glomerulonephritis; (7) graft rejection (including allograft rejection and graft-v-host disease), e.g., skin graft rejection, solid organ transplant rejection, bone marrow transplant rejection; (8) fever; (9) cardiovascular disorders, including acute heart failure, hypotension, hypertension, angina pectoris, myocardial infarction, cardiomyopathy, congestive heart failure, atherosclerosis, coronary artery disease, restenosis, and vascular stenosis; (10) cerebrovascular disorders, including traumatic brain injury, stroke, ischemic reperfusion injury and aneurysm; (11) cancers of the breast, skin, prostate, cervix, uterus, ovary, testes, bladder, lung, liver, larynx, oral cavity, colon and gastrointestinal tract (e.g., esophagus, stomach, pancreas), brain, thyroid, blood, and lymphatic system; (12) fibrosis, connective tissue disease, and sarcoidosis, (13) genital and reproductive conditions, including erectile dysfunction; (14) gastrointestinal disorders, including gastritis, ulcers, nausea, pancreatitis, and vomiting; (15) neurologic disorders, including Alzheimer's disease; (16) sleep disorders, including insomnia, narcolepsy, sleep apnea syndrome, and Pickwick Syndrome; (17) pain; (18) renal disorders; (19) ocular disorders, including glaucoma; and (20) infectious diseases, including HIV.

In one embodiment, the cancer treatable with the methods provided herein includes, but is not limited to, (1) leukemias, including, but not limited to, acute leukemia, acute lymphocytic leukemia, acute lymphoblastic leukemia, acute myelocytic leukemias such as myeloblastic, promyelocytic, myelomonocytic, monocytic, erythroleukemia leukemias and myelodysplastic syndrome or a symptom thereof (such as anemia, thrombocytopenia, neutropenia, bicytopenia or pancytopenia), refractory anemia (RA), RA with ringed sideroblasts (RARS), RA with excess blasts (RAEB), RAEB in transformation (RAEB-T), preleukemia, and chronic myelomonocytic leukemia (CMML), (2) chronic leukemias, including, but not limited to, chronic myelocytic (granulocytic) leukemia, chronic lymphocytic leukemia, and hairy cell leukemia; (3) polycythemia vera; (4) lymphomas, including, but not limited to, Hodgkin's disease and non-Hodgkin's disease; (5) multiple myelomas, including, but not limited to, smoldering multiple myeloma, nonsecretory myeloma, osteosclerotic myeloma, plasma cell leukemia, solitary plasmacytoma, and extramedullary plasmacytoma; (6) Waldenstrom's macroglobulinemia; (7) monoclonal gammopathy of undetermined significance; (8) benign monoclonal gammopathy; (9) heavy chain disease; (10) bone and connective tissue sarcomas, including, but not limited to, bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, metastatic cancers, neurilemmoma, rhabdomyosarcoma, and synovial sarcoma; (11) brain tumors, including, but not limited to, glioma, astrocytoma, brain stem glioma, ependymoma, oligodendroglioma, nonglial tumor, acoustic neurinoma, craniopharyngioma, medulloblastoma, meningioma, pineocytoma, pineoblastoma, and primary brain lymphoma; (12) breast cancer, including, but not limited to, adenocarcinoma, lobular (small cell) carcinoma, intraductal carcinoma, medullary breast cancer, mucinous breast cancer, tubular breast cancer, papillary breast cancer, primary cancers, Paget's disease, and inflammatory breast cancer; (13) adrenal cancer, including, but not limited to, pheochromocytom and adrenocortical carcinoma; (14) thyroid cancer, including, but not limited to, papillary or follicular thyroid cancer, medullary thyroid cancer, and anaplastic thyroid cancer; (15) pancreatic cancer, including, but not limited to, insulinoma, gastrinoma, glucagonoma, vipoma, somatostatin-secreting tumor, and carcinoid or islet cell tumor; (16) pituitary cancer, including, but not limited to, Cushing's disease, prolactin-secreting tumor, acromegaly, and diabetes insipius; (17) eye cancer, including, but not limited, to ocular melanoma such as iris melanoma, choroidal melanoma, and cilliary body melanoma, and retinoblastoma; (18) vaginal cancer, including, but not limited to, squamous cell carcinoma, adenocarcinoma, and melanoma; (19) vulvar cancer, including, but not limited to, squamous cell carcinoma, melanoma, adenocarcinoma, basal cell carcinoma, sarcoma, and Paget's disease; (20) cervical cancers, including, but not limited to, squamous cell carcinoma, and adenocarcinoma; (21) uterine cancer, including, but not limited to, endometrial carcinoma and uterine sarcoma; (22) ovarian cancer, including, but not limited to, ovarian epithelial carcinoma, borderline tumor, germ cell tumor, and stromal tumor; (23) esophageal cancer, including, but not limited to, squamous cancer, adenocarcinoma, adenoid cystic carcinoma, mucoepidermoid carcinoma, adenosquamous carcinoma, sarcoma, melanoma, plasmacytoma, verrucous carcinoma, and oat cell (small cell) carcinoma; (24) stomach cancer, including, but not limited to, adenocarcinoma, fungating (polypoid), ulcerating, superficial spreading, diffusely spreading, malignant lymphoma, liposarcoma, fibrosarcoma, and carcinosarcoma; (25) colon cancer; (26) rectal cancer; (27) liver cancer, including, but not limited to, hepatocellular carcinoma and hepatoblastoma; (28) gallbladder cancer, including, but not limited to, adenocarcinoma; (29) cholangiocarcinomas, including, but not limited to, pappillary, nodular, and diffuse; (30) lung cancer, including, but not limited to, non-small cell lung cancer, squamous cell carcinoma (epidermoid carcinoma), adenocarcinoma, large-cell carcinoma, and small-cell lung cancer; (31) testicular cancer, including, but not limited to, germinal tumor, seminoma, anaplastic, classic (typical), spermatocytic, non-seminoma, embryonal carcinoma, teratoma carcinoma, and choriocarcinoma (yolk-sac tumor); (32) prostate cancer, including, but not limited to, adenocarcinoma, leiomyosarcoma, and rhabdomyosarcoma; (33) penal cancer; (34) oral cancer, including, but not limited to, squamous cell carcinoma; (35) basal cancer; (36) salivary gland cancer, including, but not limited to, adenocarcinoma, mucoepidermoid carcinoma, and adenoidcystic carcinoma; (37) pharynx cancer, including, but not limited to, squamous cell cancer and verrucous; (38) skin cancer, including, but not limited to, basal cell carcinoma, squamous cell carcinoma and melanoma, superficial spreading melanoma, nodular melanoma, lentigo malignant melanoma, and acral lentiginous melanoma; (39) kidney cancer, including, but not limited to, renal cell cancer, adenocarcinoma, hypernephroma, fibrosarcoma, and transitional cell cancer (renal pelvis and/or uterer); (40) Wilms' tumor; (41) bladder cancer, including, but not limited to, transitional cell carcinoma, squamous cell cancer, adenocarcinoma, and carcinosarcoma; and other cancer, including, not limited to, myxosarcoma, osteogenic sarcoma, endotheliosarcoma, lymphangio-endotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma, and papillary adenocarcinomas (See Fishman et al., 1985, *Medicine*, 2d Ed., J.B. Lippincott Co., Philadelphia and Murphy et al., 1997, *Informed Decisions: The Complete Book of Cancer Diagnosis, Treatment, and Recovery*, Viking Penguin, Penguin Books U.S.A., Inc., United States of America).

Particular embodiments provide treating a subject having cancer using one or more of the methods provided herein, together with surgery. Particular embodiments provide treating a subject having cancer using one or more of the methods provided herein, together with chemotherapy. Particular embodiments provide treating a subject having cancer using one or more of the methods provided herein, together with immunotherapy. Particular embodiments provide treating a subject having cancer using one or more of the methods provided herein, together with targeted therapy. Particular embodiments provide treating a subject having cancer using one or more of the methods provided herein, together with radiation therapy. Particular embodiments provide treating a subject having cancer using one or more of the methods provided herein, together with two or more of the treatments selected from surgery, chemotherapy, immunotherapy, targeted therapy, and radiation therapy.

In certain embodiments, the subject to be treated with one of the methods provided herein has not been treated with anticancer therapy prior to the administration of a compound provided herein. In certain embodiments, the subject to be treated with one of the methods provided herein has been treated with one or more anticancer therapies prior to the administration of a compound provided herein. In certain embodiments, the subject to be treated with one of the methods provided herein has been treated with a cancer therapeutic agent, as described herein. In certain embodiments, the subject to be treated with one of the methods provided herein has developed drug resistance to anticancer therapy. In certain embodiments, the subject to be treated with the methods provided herein has a relapsed cancer. In certain embodiments, the subject to be treated with the methods provided herein has a refractory cancer. In certain embodiments, the subject to be treated with the methods provided herein has a metastatic cancer.

In one embodiment, provided herein are methods for treating a subject having a cancer, comprising administering to the subject a therapeutically effective amount of a compound provided herein, e.g., a compound of formula (I), or an enantiomer, a mixture of enantiomers or a mixture of diastereomers thereof, or a pharmaceutically acceptable salt, solvate, hydrate or prodrug thereof; wherein the cancer is resistant to conventional therapy (e.g., resistant to other anticancer drugs). In one embodiment, the cancer treated by a compound provided herein, e.g., a compound of formula (I), is resistant to one or more anticancer drug(s), including, but not limited to, vincristine, taxol, cytarabine, and/or doxorubicin. In one embodiment, the cancer is resistant to a therapeutic agent described herein (e.g., Section E.5, infra). In one embodiment, the cancer is vincristine-resistant. In one embodiment, the cancer is taxol-resistant. In one embodiment, the cancer is cytarabine-resistant. In one embodiment, the cancer is doxorubicin-resistant. In one embodiment, the cancer is resistant to a therapeutic agent that modulates microtubule formation. In one embodiment, the cancer is resistant to a therapeutic agent that is associated with p-glycoprotein mediated multidrug resistance.

In one embodiment, the methods provided herein encompass treating a subject regardless of patient's age, although some diseases or disorders are more common in certain age groups. Further provided herein is a method for treating a subject who has undergone surgery in an attempt to treat the disease or condition at issue. Further provided herein is a method for treating a subject who has not undergone surgery as an attempt to treat the disease or condition at issue. Because the subjects with cancer have heterogeneous clinical manifestations and varying clinical outcomes, the treatment given to a particular subject may vary, depending on his/her prognosis. The skilled clinician will be able to readily determine without undue experimentation, specific secondary agents, types of surgery, and types of non-drug based standard therapy that can be effectively used to treat an individual subject with cancer.

In each embodiment provided herein, the method may further comprise one or more diagnostic steps, to determine, e.g., the type of cancer, the presence of particular cell types, and/or the staging of the disease in a subject.

In each embodiment provided herein, the method may further comprise a disease evaluation step after the compound or pharmaceutical composition has been administered to the subject, to determine, e.g., changes in one or more molecular markers as described herein elsewhere, changes in tumor size and location, and/or other benchmarks used by those skilled in the art to determine the prognosis of cancer in a subject.

3. Biomarkers

In certain embodiments, appropriate biomarkers may be used to determine or predict the effect of the methods provided herein on the disease state and to provide guidance as to the dosing schedule and dosage amount. In particular embodiments, the greater benefit is an overall survival benefit. In particular embodiments, the greater benefit is tumor stasis and remission. In particular embodiments, the greater benefit is prevention of tumor recurrence. In one embodiment, provided herein is a method for determining whether a patient diagnosed with cancer has an increased probability of obtaining a greater benefit from treatment with a compound provided herein by assessing the level of eIF4E in the tumor biopsy samples obtained from the patient. In one embodiment, provided herein is a method for determining whether a patient diagnosed with cancer has an increased probability of obtaining a greater benefit from treatment with a compound provided herein by assessing the sensitivity of cancer cells obtained from the patient to the downregulation of protein translation initiation. In one embodiment, the method comprises assessing the activity of a compound provided herein in tumor biopsy samples in vitro. In one embodiment, the method comprises assessing the levels of one or more growth factors and/or cytokines that are important in cancer progression and weakly translated. In one embodiment, the growth factor markers and cytokine markers include, but are not limited to, VEFG, FGF, IL-1, and TGF-β. In one embodiment, provided herein is a method for determining the response of a patient to the treatment of a compound provided herein, by assessing one or more of the molecular biomarkers described herein. In one embodiment, the dosage of a compound used in treating a patient is adjusted based on the result of biomarker responses in the particular patient after initial treatment with the compound.

4. Administration of Compounds

Depending on the disorder, disease, or condition to be treated, and the subject's condition, the compounds or pharmaceutical compositions provided herein can be administered by oral, parenteral (e.g., intramuscular, intraperitoneal, intravenous, ICV, intracistemal injection or infusion, subcutaneous injection, or implant), inhalation, nasal, vaginal, rectal, sublingual, or topical (e.g., transdermal or local) routes of administration and can be formulated, alone or together, in suitable dosage unit with pharmaceutically acceptable excipients, carriers, adjuvants, and vehicles appropriate for each route of administration. Also provided is administration of the compounds or pharmaceutical compositions provided herein in a depot formulation, in which the active ingredient is released over a predefined time period. In one embodiment, the compound or composition is administered orally. In another embodiment, the compound or composition is administered parenterally. In yet another embodiment, the compound or composition is administered intravenously.

Certain methods herein provide the administration of a compound provided herein by intravenous (IV), subcutaneous (SC) or oral routes administration. Certain embodiments herein provide co-administration of a compound provided herein with one or more additional active agents to provide a synergistic therapeutic effect in subjects in need thereof. The co-administered agent(s) may be a cancer therapeutic agent, as described herein. In certain embodiments, the co-administered agent(s) may be dosed, e.g., orally or by injection (e.g., IV or SC).

Certain embodiments herein provide methods for treating disorders of abnormal cell proliferation comprising administering a compound provided herein using, e.g., IV, SC and/or oral administration methods. In certain embodiments, treatment cycles comprise multiple doses administered to a subject in need thereof over multiple days (e.g., 1, 2, 3, 4, 5, 6, 7, 8, 9, 10, 11, 12, 13, 14, or greater than 14 days), optionally followed by treatment dosing holidays (e.g., 1, 2, 3, 4, 5, 6, 7, 8, 9, 10, 11, 12, 13, 14, or greater than 14 days). Suitable dosage amounts for the methods provided herein include, e.g., therapeutically effective amounts and prophylactically effective amounts. For example, in certain embodiments, the amount of a compound provided herein administered in the methods provided herein may range, e.g., between about 10 mg/day and about 2,000 mg/day, between about 20 mg/day and about 1,000 mg/day, between about 50 mg/day and about 1,000 mg/day, between about 100 mg/day and about 1,000 mg/day, between about 100 mg/day and about 500 mg/day, between about 100 mg/day and about 200 mg/day, or between about 200 mg/day and about 500 mg/day. In certain embodiments, particular dosages are, e.g., up to about 10 mg/day, up to about 20 mg/day, up to about 40 mg/day, up to about 60 mg/day, up to about 80 mg/day, up to about 100 mg/day, up to about 120 mg/day, up to about 140 mg/day, up to about 150 mg/day, up to about 160 mg/day, up to about 180 mg/day, up to about 200 mg/day, up to about 220 mg/day, up to about 240 mg/day, up to about 250 mg/day, up to about 260 mg/day, up to about 280 mg/day, up to about 300 mg/day, up to about 320 mg/day, up to about 350 mg/day, up to about 400 mg/day, up to about 450 mg/day, up to about 500 mg/day, up to about 750 mg/day, or up to about 1000 mg/day. In certain embodiments, particular dosages are, e.g., about 10 mg/day, about 20 mg/day, about 50 mg/day, about 75 mg/day, about 100 mg/day, about 120 mg/day, about 150 mg/day, about 200 mg/day, about 250 mg/day, about 300 mg/day, about 350 mg/day, about 400 mg/day, about 450 mg/day, about 500 mg/day, about 600 mg/day, about 700 mg/day, about 800 mg/day, about 900 mg/day, about 1,000 mg/day, about 1,200 mg/day, or about 1,500 mg/day.

In one embodiment, the amount of a compound provided herein in the pharmaceutical composition or dosage form provided herein may range, e.g., between about 5 mg and about 2,000 mg, between about 10 mg and about 2,000 mg, between about 20 mg and about 2,000 mg, between about 50 mg and about 1,000 mg, between about 100 mg and about 500 mg, between about 150 mg and about 500 mg, or between about 150 mg and about 250 mg. In certain embodiments, the amount of a compound provided herein in the pharmaceutical composition or dosage form provided herein is, e.g., about 10 mg, about 20 mg, about 50 mg, about 75 mg, about 100 mg, about 120 mg, about 150 mg, about 200 mg, about 250 mg, about 300 mg, about 350 mg, about 400 mg, about 450 mg, about 500 mg, about 600 mg, about 700 mg, about 800 mg, about 900 mg, about 1,000 mg, about 1,200 mg, or about 1,500 mg. In certain embodiments, the amount of a compound provided herein in the pharmaceutical composition or dosage form provided herein is, e.g., up to about 10 mg, up to about 20 mg, up to about 50 mg, up to about 75 mg, up to about 100 mg, up to about 120 mg, up to about 150 mg, up to about 200 mg, up to about 250 mg, up to about 300 mg, up to about 350 mg, up to about 400 mg, up to about 450 mg, up to about 500 mg, up to about 600 mg, up to about 700 mg, up to about 800 mg, up to about 900 mg, up to about 1,000 mg, up to about 1,200 mg, or up to about 1,500 mg.

In one embodiment, the compound or composition can be delivered as a single dose such as, e.g., a single bolus injection, or oral tablets or pills; or over time such as, e.g., continuous infusion over time or divided bolus doses over time. In one embodiment, the compound or composition can be administered repetitively if necessary, for example, until the patient experiences stable disease or regression, or until the patient experiences disease progression or unacceptable toxicity. For example, stable disease for solid tumors generally means that the perpendicular diameter of measurable lesions has not increased by 25% or more from the last measurement.

See, e.g., Response Evaluation Criteria in Solid Tumors (RECIST) Guidelines, *Journal of the National Cancer Institute* 92(3): 205-216 (2000). Stable disease or lack thereof is determined by methods known in the art such as evaluation of patient's symptoms, physical examination, visualization of the tumor that has been imaged using X-ray, CAT, PET, or MRI scan and other commonly accepted evaluation modalities.

In one embodiment, the compound or composition can be administered once daily (QD), or divided into multiple daily doses such as twice daily (BID), three times daily (TID), and four times daily (QID). In one embodiment, the administration can be continuous (i.e., daily for consecutive days or every day), intermittent, e.g., in cycles (i.e., including days, weeks, or months of rest when no drug is administered). In one embodiment, the compound or composition is administered daily, for example, once or more than once each day for a period of time. In one embodiment, the compound or composition is administered daily for an uninterrupted period of at least 7 days, in some embodiments, up to 52 weeks. In one embodiment, the compound or composition is administered intermittently, i.e., stopping and starting at either regular or irregular intervals. In one embodiment, the compound or composition is administered for one to six days per week. In one embodiment, the compound or composition is administered in cycles (e.g., daily administration for two to eight consecutive weeks, then a rest period with no administration for up to one week). In one embodiment, the compound or composition is administered on alternate days. In one embodiment, the compound or composition is administered in cycles (e.g., administered daily or continuously for a certain period interrupted with a rest period).

In one embodiment, the frequency of administration ranges from about daily to about monthly. In certain embodiments, the compound or composition is administered once a day, twice a day, three times a day, four times a day, once every other day, twice a week, once every week, once every two weeks, once every three weeks, or once every four weeks.

In one embodiment, the compound or composition is administered daily from one day to six months, from one week to three months, from one week to four weeks, from one week to three weeks, or from one week to two weeks. In certain embodiments, the compound or composition is administered daily for one week, two weeks, three weeks, or four weeks. In one embodiment, the compound or composition is administered once per day for about 1 week, about 2 weeks, about 3 weeks, about 4 weeks, about 6 weeks, about 9 weeks, about 12 weeks, about 15 weeks, about 18 weeks, about 21 weeks, or about 26 weeks. In certain embodiments, the compound or composition is administered intermittently. In certain embodiments, the compound or composition is administered continuously. In certain embodiments, the compound or composition is administered to a subject in cycles. Cycling therapy involves the administration of an active agent for a period of time, followed by a rest for a period of time, and repeating this sequential administration. Cycling therapy can reduce the development of resistance, avoid or reduce the side effects, and/or improves the efficacy of the treatment.

It is understood that the duration of the treatment may vary with the age, weight, and condition of the subject being treated, and may be determined empirically using known testing protocols or according to the professional judgment of the person providing or supervising the treatment. The skilled clinician will be able to readily determine, without undue experimentation, an effective drug dose and treatment duration, for treating an individual subject having a particular type of cancer.

5. Co-Administered Therapeutic Agents

In one embodiment, the method provided herein for treating, preventing, or ameliorating a disorder provided herein comprise co-administering a compound provided herein, e.g., a compound of formula (I), or an enantiomer, a mixture of enantiomers or a mixture of diastereomers thereof, or a pharmaceutically acceptable salt, solvate, hydrate or prodrug thereof, with one or more therapeutic agents, such as, e.g., cancer therapeutic agents, to yield a synergistic therapeutic effect. In one embodiment, the disorder being treated, prevented, or ameliorated is cancer. In one embodiment, the co-administered therapeutic agents include, but are not limited to, e.g., cytotoxic agents, antimetabolites, antifolates, HDAC inhibitors such as MGCD0103 (a.k.a. N-(2-aminophenyl)-4-((4-(pyridin-3-yl) pyrimidin-2-ylamino)methyl)benzamide), DNA intercalating agents, DNA cross-linking agents, DNA alkylating agents, DNA cleaving agents, topoisomerase inhibitors, CDK inhibitors, JAK inhibitors, anti-angiogenic agents, Bcr-Abl inhibitors, HER2 inhibitors, EGFR inhibitors, VEGFR inhibitors, PDGFR inhibitors, HGFR inhibitors, IGFR inhibitors, c-Kit inhibitors, Ras pathway inhibitors, PI3K inhibitors, multi-targeted kinase inhibitors, mTOR inhibitors, antiestrogens, anti-androgens, aromatase inhibitors, somatostatin analogs, ER modulators, anti-tubulin agents, vinca alkaloids, taxanes, HSP inhibitors, Smoothened antagonists, telomerase inhibitors, COX-2 inhibitors, anti-metastatic agents, immunosuppressants, biologics such as antibodies, and hormonal therapies. The co-administered agent may be dosed, e.g., orally or by injection. In one embodiment, each method provided herein may independently, further comprise the step of administering a second therapeutic agent, including, e.g., an anticancer agent.

In one embodiment, one or more therapeutic agent is/are an anticancer agent to be coadministered with a compound provided herein e.g., a compound of formula (I), or an enantiomer, a mixture of enantiomers or a mixture of diastereomers thereof, or a pharmaceutically acceptable salt, solvate, hydrate or prodrug thereof. In one embodiment, the anticancer agent is an antimetabolite, including, but not limited to, 5-fluoro uracil, methotrexate, cytarabine, high dose cytarabine, and fludarabine. In one embodiment, the anticancer agent is an antimicrotubule agent, including, but not limited to, vinca alkaloids (e.g., vincristine and vinblastine) and taxanes (e.g., paclitaxel and docetaxel). In one embodiment, the anticancer agent is an alkylating agent, including, but not limited to, cyclophosphamide, melphalan, carmustine, and nitrosoureas (e.g., hydroxyurea and bischloroethylnitrosurea). In one embodiment, the anticancer agent is a platinum agent, including, but not limited to, cisplatin, carboplatin, oxaliplatin, satraplatin (JM-216), and CI-973. In one embodiment, the anticancer agent is an anthracycline, including, but not limited to, doxrubicin and daunorubicin. In one embodiment, the anticancer agent is an antitumor antibiotic, including, but not limited to, mitomycin, idarubicin, adriamycin, and daunomycin (also known as daunorubicin). In one embodiment, the anticancer agent is a topoisomerase inhibitor, e.g., etoposide and camptothecins. In one embodiment, the anticancer agent is selected from the group consisting of adriamycin, busulfan, cytarabine, cyclophosphamide, dexamethasone, fludarabine, fluorouracil, hydroxyurea, interferons, oblimersen, platinum derivatives, taxol, topotecan, and vincristine.

In one embodiment, the route of the administration of the compound provided herein is independent of the route of the administration of a second therapy. In one embodiment, the compound provided herein is administered orally. In another embodiment, the compound provided herein is administered intravenously. In accordance with these embodiments, i.e., administering the compound provided herein orally or intravenously, the second therapy can be administered orally, parenterally, intraperitoneally, intravenously, intraarterially, transdermally, sublingually, intramuscularly, rectally, transbuccally, intranasally, liposomally, via inhalation, vaginally, intraoccularly, via local delivery by catheter or stent, subcutaneously, intraadiposally, intraarticularly, intrathecally, or in a slow release dosage form. In one embodiment, the compound provided herein and a second therapy are administered by the same mode of administration, e.g., orally or intravenously. In another embodiment, the compound provided herein is administered by one mode of administration, e.g., orally, whereas the second agent (e.g., an anticancer agent) is administered by another mode of administration, e.g., intravenously. In another embodiment, the compound provided herein is administered by one mode of administration, e.g., intravenously, whereas the second agent (e.g., an anticancer agent) is administered by another mode of administration, e.g., orally.

Suitable other therapeutic agents can also include, but are not limited to, (1) alpha-adrenergic agents; (2) antiarrhythmic agents; (3) anti-atherosclerotic agents, such as ACAT inhibitors; (4) antibiotics, such as anthracyclines, bleomycins, mitomycin, dactinomycin, and plicamycin; (5) anticancer agents and cytotoxic agents, e.g., alkylating agents, such as nitrogen mustards, alkyl sulfonates, nitrosoureas, ethylenimines, and triazenes; (6) anticoagulants, such as acenocoumarol, argatroban, bivalirudin, lepirudin, fondaparinux, heparin, phenindione, warfarin, and ximelagatran; (7) antidiabetic agents, such as biguanides (e.g., metformin), glucosidase inhibitors (e.g., acarbose), insulins, meglitinides (e.g., repaglinide), sulfonylureas (e.g., glimepiride, glyburide, and glipizide), thiozolidinediones (e.g., troglitazone, rosiglitazone, and pioglitazone), and PPAR-gamma agonists; (8) antifungal agents, such as amorolfine, amphotericin B, anidulafungin, bifonazole, butenafine, butoconazole, caspofungin, ciclopirox, clotrimazole, econazole, fenticonazole, filipin, fluconazole, isoconazole, itraconazole, ketoconazole, micafungin, miconazole, naftifine, natamycin, nystatin, oxyconazole, ravuconazole, posaconazole, rimocidin, sertaconazole, sulconazole, terbinafine, terconazole, tioconazole, and voriconazole; (9) antiinflammatories, e.g., non-steroidal anti-inflammatory agents, such as aceclofenac, acemetacin, amoxiprin, aspirin, azapropazone, benorilate, bromfenac, carprofen, celecoxib, choline magnesium salicylate, diclofenac, diflunisal, etodolac, etoricoxib, faislamine, fenbufen, fenoprofen, flurbiprofen, ibuprofen, indometacin, ketoprofen, ketorolac, lornoxicam, loxoprofen, lumiracoxib, meclofenamic acid, mefenamic acid, meloxicam, metamizole, methyl salicylate, magnesium salicylate, nabumetone, naproxen, nimesulide, oxyphenbutazone, parecoxib, phenylbutazone, piroxicam, salicyl salicylate, sulindac, sulfinpyrazone, suprofen, tenoxicam, tiaprofenic acid, and tolmetin; (10) antimetabolites, such as folate antagonists, purine analogues, and pyrimidine analogues; (11) anti-platelet agents, such as GPIIb/IIIa blockers (e.g., abciximab, eptifibatide, and tirofiban), P2Y(AC) antagonists (e.g., clopidogrel, ticlopidine and CS-747), cilostazol, dipyridamole, and aspirin; (12) antiproliferatives, such as methotrexate, FK506 (tacrolimus), and mycophenolate mofetil; (13) anti-TNF antibodies or soluble TNF receptor, such as etanercept, rapamycin, and leflunimide; (14) aP2 inhibitors; (15) beta-adrenergic agents, such as carvedilol and metoprolol; (16) bile acid sequestrants, such as questran; (17) calcium channel blockers, such as amlodipine besylate; (18) chemotherapeutic agents; (19) cyclooxygenase-2 (COX-2) inhibitors, such as celecoxib and rofecoxib; (20) cyclosporine; (21) cytotoxic drugs, such as azathioprine and cyclophosphamide; (22) diuretics, such as chlorothiazide, hydrochlorothiazide, flumethiazide, hydroflumethiazide, bendroflumethiazide, methylchlorothiazide, trichloromethiazide, polythiazide, benzothiazide, ethacrynic acid, ticrynafen, chlorthalidone, furosenide, muzolimine, bumetanide, triamterene, amiloride, and spironolactone; (23) endothelin converting enzyme (ECE) inhibitors, such as phosphoramidon; (24) enzymes, such as L-asparaginase; (25) Factor VIIa Inhibitors and Factor Xa Inhibitors; (26) farnesyl-protein transferase inhibitors; (27) fibrates; (28) growth factor inhibitors, such as modulators of PDGF activity; (29) growth hormone secretagogues; (30) HMG CoA reductase inhibitors, such as pravastatin, lovastatin, atorvastatin, simvastatin, NK-104 (a.k.a. itavastatin, nisvastatin, or nisbastatin), and ZD-4522 (also known as rosuvastatin, atavastatin, or visastatin); neutral endopeptidase (NEP) inhibitors; (31) hormonal agents, such as glucocorticoids (e.g., cortisone), estrogens/antiestrogens, androgens/antiandrogens, progestins, and luteinizing hormone-releasing hormone antagonists, and octreotide acetate; (32) immunosuppressants; (33) mineralocorticoid receptor antagonists, such as spironolactone and eplerenone; (34) microtubule-disruptor agents, such as ecteinascidins; (35) microtubule-stabilizing agents, such as pacitaxel, docetaxel, and epothilones A-F; (36) MTP Inhibitors; (37) niacin; (38) phosphodiesterase inhibitors, such as PDE III inhibitors (e.g., cilostazol) and PDE V inhibitors (e.g., sildenafil, tadalafil, and vardenafil); (39) plant-derived products, such as vinca alkaloids, epipodophyllotoxins, and taxanes; (40) platelet activating factor (PAF) antagonists; (41) platinum coordination complexes, such as cisplatin, satraplatin, and carboplatin; (42) potassium channel openers; (43) prenyl-protein transferase inhibitors; (44) protein tyrosine kinase inhibitors; (45) renin inhibitors; (46) squalene synthetase inhibitors; (47) steroids, such as aldosterone, beclometasone, betamethasone, deoxycorticosterone acetate, fludrocortisone, hydrocortisone (cortisol), prednisolone, prednisone, methylprednisolone, dexamethasone, and triamcinolone; (48) TNF-alpha inhibitors, such as tenidap; (49) thrombin inhibitors, such as hirudin; (50) thrombolytic agents, such as anistreplase, reteplase, tenecteplase, tissue plasminogen activator (tPA), recombinant tPA, streptokinase, urokinase, prourokinase, and anisoylated plasminogen streptokinase activator complex (APSAC); (51) thromboxane receptor antagonists, such as ifetroban; (52) topoisomerase inhibitors; (53) vasopeptidase inhibitors (dual NEP-ACE inhibitors), such as omapatrilat and gemopatrilat; and (54) other miscellaneous agents, such as, hydroxyurea, procarbazine, mitotane, hexamethylmelamine, and gold compounds.

In one embodiment, other therapies or anticancer agents that may be used in combination with the compound provided herein include surgery, radiotherapy (e.g., gamma-radiation, neutron beam radiotherapy, electron beam radiotherapy, proton therapy, brachytherapy, and systemic radioactive isotopes), endocrine therapy, biologic response modifiers (e.g., interferons, interleukins, and tumor necrosis factor (TNF)), hyperthermia and cryotherapy, agents to attenuate any adverse effects (e.g., antiemetics), and other approved chemotherapeutic drugs, including, but not limited to, alkylating drugs (mechlorethamine, chlorambucil, cyclophosphamide, melphalan, and ifosfamide), antimetabolites (cytarabine, high dose cytarabine, and methotrexate), purine antagonists and pyrimidine antagonists (6-mercaptopurine, 5-fluorouracil, cytarabine, and gemcitabine), spindle poisons (vinblastine, vincristine, vinorelbine, and paclitaxel), podophyllotoxins (etoposide, irinotecan, and topotecan), antibiotics (daunorubicin, doxorubicin, bleomycin, and mitomycin), nitrosoureas (carmustine and lomustine), inorganic ions (cisplatin and carboplatin), enzymes (asparaginase), and hormones (tamoxifen, leuprolide, flutamide, and megestrol), imatinib, adriamycin, dexamethasone, and cyclophosphamide. For additional available cancer therapies, see, e.g, http://www.nci.nih.gov/; for a list of FDA approved oncology drugs, see, e.g., http://www.fda.gov/, The Merck Manual, 18th Ed. 2006, and PDR: Physician Desk Reference 2010, 64th Ed. 2009; the contents of each of which are hereby incorporated by reference in their entireties.

EXAMPLES

Certain embodiments are illustrated by the following non-limiting examples.

A. Synthesis of Compounds

In the examples below, unless otherwise indicated, all temperatures are set forth in degrees Celsius and all parts and percentages are by weight. Reagents may be purchased from commercial suppliers, such as Sigma-Aldrich Chemical Company, and may be used without further purification unless otherwise indicated. Reagents may also be prepared following standard literature procedures known to those skilled in the art. Solvents may be purchased from Aldrich in Sure-Seal bottles and used as received. All solvents may be purified using standard methods known to those skilled in the art, unless otherwise indicated.

The reactions set forth below were done generally at ambient temperature, unless otherwise indicated. In one embodiment, the reaction flasks were fitted with rubber septa for introduction of substrates and reagents via syringe. In one embodiment, analytical thin layer chromatography (TLC) was performed using glass-backed silica gel pre-coated plates (Whatman MK6F Silica Gel 60 Å, 2.5×7.6 cm, TLC plates) and eluted with appropriate solvent ratios (v/v). In one embodiment, reactions were assayed by TLC, HPLC, or LCMS, and terminated as judged by the consumption of starting material. In one embodiment, visualization of the TLC plates was done with UV light (254 wavelength) or with an appropriate TLC visualizing solvent, such as basic aqueous $KMnO_4$ solution activated with heat. In one embodiment, flash column chromatography (See, e.g., Still et al., *J. Org. Chem.*, 43: 2923 (1978)) was performed using silica gel 60 (Whatman Silica Gel 60 Å 70-230 Mesh ASTM) or various MPLC systems.

The compound structures in the examples below were confirmed by one or more of the following methods: proton magnetic resonance spectroscopy, mass spectroscopy, elemental microanalysis, and melting point. In one embodiment, proton magnetic resonance ($^1$H-NMR) spectra were determined using a NMR spectrometer operating at a certain field strength. Chemical shifts are reported in parts per million (ppm, δ) downfield from an internal standard, such as TMS. Alternatively, $^1$H-NMR spectra were referenced to signals from residual protons in deuterated solvents as follows: $CDCl_3$=7.25 ppm; DMSO-$d_6$=2.49 ppm; $C_6D_6$=7.16 ppm; $CD_3OD$=3.30 ppm. Peak multiplicities are designated as follows: s, singlet; d, doublet; dd, doublet of doublets; t, triplet; dt, doublet of triplets; q, quartet; br, broadened; and m, multiplet. Coupling constants are given in Hertz (Hz). In one embodiment, mass spectra (MS) data were obtained using a mass spectrometer with APCI or ESI ionization.

Example 1

Compound 1: N-[3,5-Bis(trifluoromethyl)phenyl]-2,4,6-triisopropyl-benzenesulfonamide

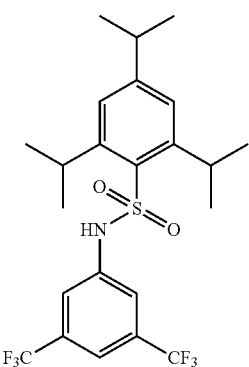

Method A. 2,4,6-Triisopropyl-benzenesulfonyl chloride (0.210 g, 0.693 mmol) was added to a solution of 3,5-bis-trifluoromethyl-phenylamine (0.159 g, 0.693 mmol) in dry pyridine (1 mL). After stirring at room temperature for 1 day, the reaction was concentrated under vacuum. To this was added ethyl acetate (30 mL), and the mixture was washed with dilute HCl (2×30 mL) followed by saturated NaHCO$_3$ (2×30 mL) then brine (saturated NaCl, 2×30 mL). After drying the organic layer over MgSO$_4$, the mixture was concentrated under vacuum. The crude compound was purified by silica gel chromatography using hexanes/ethyl acetate (10:1) to afford the title compound (0.046 g. 13% yield). ES-MS negative Q1 (m/z) 494.7. $^1$H NMR (CDCl$_3$) 7.55 (s, 1H), 7.31 (s, 2H), 7.18 (s, 2H), 6.98 (s, 1H), 4.10 (m, 2H), 2.90 (m, 1H), 1.23 (m, 18H).

Compound 1: N-[3,5-Bis(trifluoromethyl)phenyl]-2,4,6-triisopropyl-benzenesulfonamide

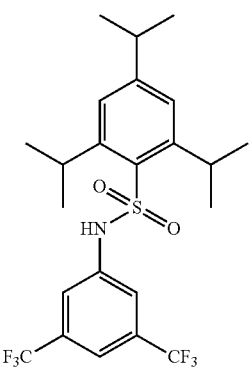 [SMILES: CC(C)c1cc(C(C)C)c(S(=O)(=O)Nc2cc(C(F)(F)F)cc(C(F)(F)F)c2)c(C(C)C)c1]

Method B. 2,4,6-Triisopropyl-benzenesulfonyl chloride (5.00 g, 16.5 mmol) was added to a solution of 3,5-bis(trifluoromethyl)aniline (3.79 g, 16.5 mmol) in dry pyridine (4 mL). The reaction was capped and stirred at room temperature for 2 days then concentrated under vacuum. To this was added diethyl ether (100 mL), and the mixture was washed with 0.1 N HCl (2×30 mL) followed by saturated NaHCO$_3$ (2×30 mL) then saturated NaCl (2×30 mL). After drying the organic layer over MgSO$_4$, the mixture was concentrated under vacuum. The crude compound was passed through a plug of silica gel, eluted with ether, and concentrated. The resulting solid was triturated with hexanes to afford the title compound (3.72 g. 43% yield). ES-MS negative Q1 (m/z) 494.7. $^1$H NMR (CDCl$_3$) 7.55 (s, 1H), 7.32 (s, 2H), 7.18 (s, 2H), 6.99 (s, 1H), 4.09 (m, 2H), 2.90 (m, 1H), 1.23 (m, 18H).

Example 2

Compound 2: N-[2-Methyl-3,5-bis(trifluoromethyl)phenyl]-2,4,6-triisopropyl-benzenesulfonamide

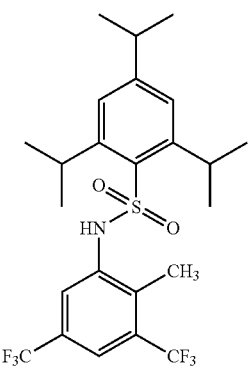

Method A. 2,4,6-Triisopropyl-benzenesulfonyl chloride (0.150 g, 0.495 mmol) was added to a solution of 2-methyl-3,5-bis-trifluoromethyl-phenylamine (0.120 g, 0.495 mmol) in dry pyridine (1 mL). After stirring at room temperature for 1 day, the reaction was concentrated under vacuum. To this was added ethyl acetate (30 mL), and the mixture was washed with dilute HCl (2×30 mL) followed by saturated NaHCO$_3$ (2×30 mL) then brine (saturated NaCl, 2×30 mL). After drying the organic layer over MgSO$_4$, the mixture was concentrated under vacuum. The crude compound was purified by silica gel chromatography using hexanes/ethyl acetate (10:1) to afford the title compound (0.050 g. 20% yield). ES-MS negative Q1 (m/z) 508.5. $^1$H NMR (CDCl$_3$) 7.67 (s, 1H), 7.19 (s, 2H), 7.18 (s, 1H), 6.46 (s, 1H), 3.97 (m, 2H), 2.92 (m, 1H), 2.42 (s, 3H), 1.25 (d, 6H), 1.18 (d, 12H).

Compound 2: N-[2-Methyl-3,5-bis(trifluoromethyl)phenyl]-2,4,6-triisopropyl-benzenesulfonamide

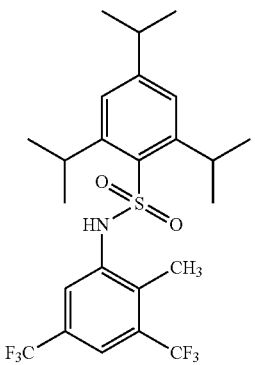

Method B. 2,4,6-Triisopropyl-benzenesulfonyl chloride (2.49 g, 8.23 mmol) was added to a solution of 2-methyl-3,5-bis(trifluoromethyl)aniline (2.00 g, 8.23 mmol) and dry pyridine (3 mL) in a 20 mL scintillation vial. The reaction was capped and stirred at room temperature for 1 day then stirred at 30° C. for 1 day. The reaction was then concentrated under vacuum. To this was added diethyl ether (125 mL) and the mixture was washed with 0.1 N HCl (3×30 mL) followed by 0.1 N NaOH (2×30 mL) then saturated NaCl (2×30 mL). After drying the organic layer over MgSO$_4$, the solution was filtered and concentrated under vacuum. The crude compound was triturated with hexanes (3×10 mL) then dried under vacuum to afford the title compound (1.68 g. 40% yield). ES-MS negative Q1 (m/z) 508.5. LCMS (M+Na) 532. $^1$H NMR (CDCl$_3$) 7.67 (s, 1H), 7.19 (s, 2H), 7.18 (s, 1H), 6.50 (s, 1H), 3.98 (m, 2H), 2.91 (m, 1H), 2.42 (s, 3H), 1.25 (d, 6H), 1.18 (d, 12H).

Example 3

Compound 3: N-[2-Chloro-3,5-bis(trifluoromethyl) phenyl]-2,4,6-triisopropyl-benzenesulfonamide

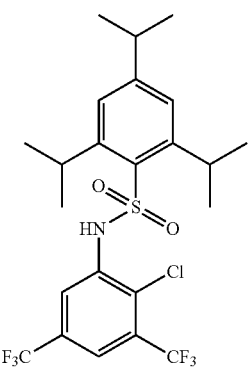

Method A. 2,4,6-Triisopropyl-benzenesulfonyl chloride (0.520 g, 1.97 mmol) was added to a solution of 2-chloro-3,5-bis-trifluoromethyl-phenylamine (0.597 g, 1.97 mmol) in dry pyridine (4 mL). After stirring under nitrogen at 78° C. for 1 day, the reaction was concentrated under vacuum. To this was added ethyl acetate (90 mL), and the mixture was washed with dilute HCl (2×60 mL) followed by saturated NaHCO$_3$ (2×60 mL) then brine (saturated NaCl, 2×60 mL). After drying the organic layer over MgSO$_4$, the mixture was concentrated under vacuum. The crude compound was purified by silica gel chromatography using hexanes/ethyl acetate (10:1) and recrystallized from hexanes/ether (2:1) to afford the title compound (0.175 g. 18% yield). ES-MS negative Q1 (m/z) 528.9. $^1$H NMR (CDCl$_3$) 7.64 (s, 1H), 7.59 (s, 1H), 7.45 (bs, 1H), 7.19 (s, 2H), 4.10 (m, 2H), 2.90 (m, 1H), 1.24 (m, 18H).

Compound 3: N-[2-Chloro-3,5-bis(trifluoromethyl) phenyl]-2,4,6-triisopropyl-benzenesulfonamide

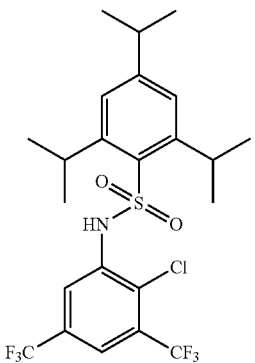

Method B. 2,4,6-Triisopropyl-benzenesulfonyl chloride (2.49 g, 8.23 mmol) was added to a solution of 2-chloro-3,5-bis(trifluoromethyl)aniline (2.17 g, 8.23 mmol) and dry pyridine (3 mL) in a 20 mL scintillation vial. The reaction was capped and stirred at room temperature for 1 day then stirred at 30° C. for 1 day. The reaction was then concentrated under vacuum. To this was added diethyl ether (125 mL) and the mixture was washed with 0.1 N HCl (3×30 mL) followed by 0.1 N NaOH (2×30 mL) then saturated NaCl (2×30 mL). After drying the organic layer over MgSO$_4$, the solution was filtered and concentrated under vacuum. The crude compound was triturated with hexanes (3×10 mL) then dried under vacuum to afford the title compound (1.26 g. 29% yield). ES-MS negative Q1 (m/z) 528.9. $^1$H NMR (CDCl$_3$) 7.64 (s, 1H), 7.59 (s, 1H), 7.45 (bs, 1H), 7.19 (s, 2H), 4.10 (m, 2H), 2.90 (m, 1H), 1.24 (m, 18H).

Example 4

Compound 4: 3,5-Bis(trifluoromethyl)-N-(2,4,6-triisopropylphenyl)benzenesulfonamide

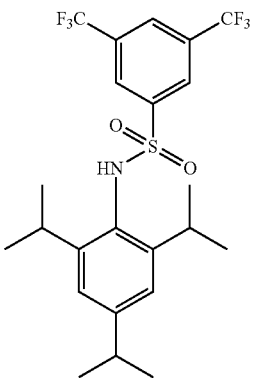 [SMILES: CC(C)c1cc(C(C)C)c(NS(=O)(=O)c2cc(C(F)(F)F)cc(C(F)(F)F)c2)c(C(C)C)c1]

3,5-Bis(trifluoromethyl)benzenesulfonyl chloride (0.037 g, 0.12 mmol) was added to a solution of 2,4,6-triisopropylaniline (0.025 g, 0.11 mmol) in dry pyridine (1 mL). After stirring at room temperature for 1 day, the reaction was concentrated under vacuum. To this was added ethyl acetate (30 mL), and the mixture was washed with 0.1 N HCl (2×20 mL) followed by saturated NaHCO$_3$ (2×20 mL) then saturated NaCl (2×20 mL). After drying the organic layer over MgSO₄, the mixture was concentrated under vacuum. The crude compound was purified by silica gel chromatography using hexanes/ethyl acetate (4:1) to afford the title compound (0.040 g, 71% yield). ES-MS negative Q1 (m/z) 494.6. $^1$H NMR (CDCl₃) 8.14 (s, 2H), 8.05 (s, 1H), 6.96 (s, 2H), 6.05 (s, 1H), 2.97 (m, 2H), 2.88 (m, 1H), 1.23 (d, 6H), 0.98 (d, 12H).

Example 5

Compound 5: N-[2-Bromo-3,5-bis(trifluoromethyl)phenyl]-2,4,6-triisopropyl-benzenesulfonamide

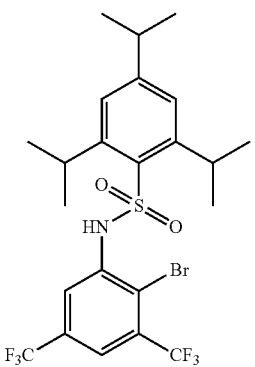 [SMILES: CC(C)c1cc(C(C)C)c(S(=O)(=O)Nc2cc(C(F)(F)F)cc(C(F)(F)F)c2Br)c(C(C)C)c1]

2,4,6-Triisopropyl-benzenesulfonyl chloride (0.491 g, 1.59 mmol) was added to a solution of 2-bromo-3,5-bis(trifluoromethyl)aniline (0.483 g, 1.59 mmol) in dry pyridine (1 mL). The reaction was capped and stirred at room temperature for 1 day then stirred at 30° C. for 1 day. The reaction was then concentrated under vacuum. To this was added diethyl ether (100 mL) and the mixture was washed with 0.1 N HCl (3×30 mL) followed by 0.1 N NaOH (2×30 mL) then saturated NaCl (2×30 mL). After drying the organic layer over MgSO₄, the solution was filtered and concentrated under vacuum. The crude compound was purified by silica gel chromatography using hexanes/ethyl acetate (10:1) to afford the title compound (0.036 g, 4% yield). LCMS (M+Na) 597.

Example 6

Compound 6: N-[3,5-Bis(trifluoromethyl)phenyl]-4-tert-butyl-2,6-dimethyl-benzenesulfonamide

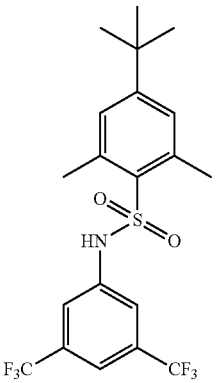 [SMILES: Cc1cc(C(C)(C)C)cc(C)c1S(=O)(=O)Nc1cc(C(F)(F)F)cc(C(F)(F)F)c1]

4-Tert-butyl-2,6-dimethyl-benzenesulfonyl chloride (0.100 g, 0.383 mmol) was added to a solution of 3,5-bis(trifluoromethyl)aniline (0.089 g, 0.387 mmol) in dry pyridine (1 mL). The reaction was capped and stirred at room temperature for 1 day then stirred at 30° C. for 1 day. The reaction was then concentrated under vacuum. To this was added diethyl ether (60 mL) and the mixture was washed with 0.1 N HCl (3×20 mL) followed by 0.1 N NaOH (2×20 mL) then saturated NaCl (2×20 mL). After drying the organic layer over MgSO₄, the solution was filtered and concentrated under vacuum. The crude compound was triturated with hexanes (2×10 mL) to afford the title compound (0.040 g, 23% yield). LCMS (M+Na) 476.

Example 7

Compound 7: 2,6-Diethyl-N-[2-methyl-3,5-bis(trifluoromethyl)phenyl]benzenesulfonamide

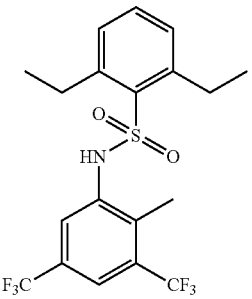 [SMILES: CCc1cccc(CC)c1S(=O)(=O)Nc1cc(C(F)(F)F)cc(C(F)(F)F)c1C]

2,6-Diethylbenzenesulfonyl chloride (0.100 g, 0.430 mmol) was added to a solution of 2-methyl-3,5-bis(trifluoromethyl)aniline (0.106 g, 0.434 mmol) in dry pyridine (1 mL). The reaction was capped and stirred at room temperature for 1 day then stirred at 30° C. for 1 day. The reaction was then concentrated under vacuum. To this was added diethyl ether (60 mL) and the mixture was washed with 0.1 N HCl (3×20 mL) followed by 0.1 N NaOH (2×20 mL) then saturated NaCl (2×20 mL). After drying the organic layer over MgSO₄, the solution was filtered and concentrated under vacuum. The crude compound was purified by silica gel chromatography using hexanes/ethyl acetate (4:1) to afford the title compound (0.080 g, 42% yield). LCMS (M+Na) 461.

Example 8

Compound 8: N-[3,5-Bis(trifluoromethyl)phenyl]-2,6-diethyl-benzene sulfonamide

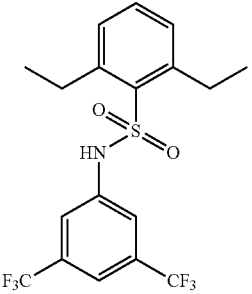 [SMILES: CCc1cccc(CC)c1S(=O)(=O)Nc1cc(C(F)(F)F)cc(C(F)(F)F)c1]

2,6-Diethylbenzenesulfonyl chloride (0.100 g, 0.430 mmol) was added to a solution of 3,5-bis(trifluoromethyl)aniline (0.099 g, 0.434 mmol) in dry pyridine (1 mL). The reaction was capped and stirred at room temperature for 1 day then stirred at 30° C. for 1 day. The reaction was then concentrated under vacuum. To this was added diethyl ether (60 mL) and the mixture was washed with 0.1 N HCl (3×20 mL) followed by 0.1 N NaOH (2×20 mL) then saturated NaCl (2×20 mL). After drying the organic layer over MgSO$_4$, the solution was filtered and concentrated under vacuum. The crude compound was triturated with hexanes (2×10 mL) to afford the title compound (0.037 g, 20% yield). LCMS (M+Na) 447.

Example 9

Compound 9: 4-Tert-butyl-2,6-dimethyl-N-[2-methyl-3,5-bis(trifluoromethyl)phenyl]benzenesulfonamide

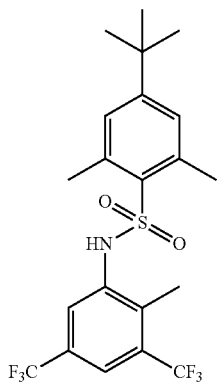 [SMILES: Cc1cc(C(C)(C)C)cc(C)c1S(=O)(=O)Nc1cc(C(F)(F)F)cc(C(F)(F)F)c1C]

4-Tert-butyl-2,6-dimethyl-benzenesulfonyl chloride (0.100 g, 0.383 mmol) was added to a solution of 2-methyl-3,5-bis(trifluoromethyl)aniline (0.094 g, 0.387 mmol) in dry pyridine (1 mL). The reaction was capped and stirred at room temperature for 1 day then stirred at 30° C. for 1 day. The reaction was then concentrated under vacuum. To this was added diethyl ether (60 mL) and the mixture was washed with 0.1 N HCl (3×20 mL) followed by 0.1 N NaOH (2×20 mL) then saturated NaCl (2×20 mL). After drying the organic layer over MgSO$_4$, the solution was filtered and concentrated under vacuum. The crude compound was triturated with hexanes (3×10 mL) to afford the title compound (0.051 g, 28% yield). LCMS (M+Na) 490.

Example 10

Compound 10: 4-Tert-butyl-N-[2-chloro-3,5-bis(trifluoromethyl)phenyl]-2,6-dimethyl-benzenesulfonamide

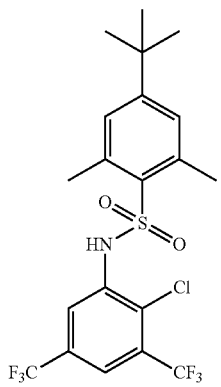 [SMILES: Cc1cc(C(C)(C)C)cc(C)c1S(=O)(=O)Nc1cc(C(F)(F)F)cc(C(F)(F)F)c1Cl]

4-Tert-butyl-2,6-dimethyl-benzenesulfonyl chloride (0.100 g, 0.383 mmol) was added to a solution of 2-chloro-3,5-bis(trifluoromethyl)aniline (0.101 g, 0.387 mmol) in dry pyridine (1 mL). The reaction was capped and stirred at room temperature for 1 day then stirred at 30° C. for 1 day. The reaction was then concentrated under vacuum. To this was added diethyl ether (60 mL) and the mixture was washed with 0.1 N HCl (3×20 mL) followed by 0.1 N NaOH (2×20 mL) then saturated NaCl (2×20 mL). After drying the organic layer over MgSO$_4$, the solution was filtered and concentrated under vacuum. The crude compound was triturated with hexanes (2×10 mL) to afford the title compound (0.027 g, 14% yield). LCMS (M+Na) 510.

B. Determination of IC$_{50}$ in Cell-Based Assays

In one embodiment, the IC$_{50}$s of the compounds provided herein were determined in cell-based assays using adherent cells. In one embodiment, the activity of the compounds provided herein were determined in a cell-based assay using the triple negative breast cancer cell line MDA-MB-468. In one embodiment, the activity of the compounds provided herein were determined in a cell-based assay using the triple negative breast cancer cell line MDA-MB-231. In one embodiment, the activity of the compounds provided herein were determined in a cell-based assay using the triple negative breast cancer cell line 4T1.

In one embodiment, the cell-based assay may be carried out as provided herein. On day 0, cells were seeded at 20,000 cells per well in 100 µL of media into individual wells of a 96-well tissue culture plate. The next day, compounds were diluted to twice the desired final concentration and added in 100 µL of media for a final volume of 200 µL. Standard solutions for each compound were prepared at 1000× concentration in DMSO. The highest concentration was 30 mM. Serial 1:1 dilutions were made from there for a 6- or 9-point curve (e.g., 20 mM, 10 mM, 5 mM, etc). Compounds were then diluted 1:500 in media, and 100 µL of the resulting solution was added to each well for a final dilution of 1:1000. Each concentration of compound was tested in triplicate. Cells were incubated at 37° C. with 5% CO$_2$. After 72 hours, 20 µL of CellTiter 96 Aqueous One Solution Cell Proliferation Assay (Promega) was added to each well. Cells were placed back in the incubator, and the absorbance at 490 nm was read after 2-3 hours. The concentration of compound that decreased the number of metabolically active cells by 50% was determined and reported as the IC$_{50}$. "Percent Viability" was determined by subtracting the average background value (media only) and expressed as a ratio to the average value obtained from cells treated with only DMSO.

The compounds provided herein were tested in a panel of cell-based assays of adherent cell types. The pharmacokinetics of the compounds provided herein were also profiled. The data is summarized in Table 1 and Table 2.

TABLE 1

IC$_{50}$ in Triple Negative Breast Cancer Cell Lines (µM)

| | Compound No. | | |
|---|---|---|---|
| | 1 | 2 | 3 |
| Molecular Weight | 496 | 510 | 529 |
| MDA-MB-468 IC$_{50}$ | 5 µM | 2 µM | 4.5 µM |
| MDA-MB-231 IC$_{50}$ | 13 µM | 6 µM | 3 µM |
| 4T1 IC$_{50}$ | 15 µM | 5 µM | |

TABLE 2

IC$_{50}$ in Adherent Cell Lines (µM) with Elevated eIF4E

| Cell Line | IC$_{50}$: 1, 2, or 3 |
|---|---|
| SK-MEL-2 (malignant melanoma) | 2-16 µM |
| SK-MEL-5 (malignant melanoma)[1] | 3-17 µM |
| SK-MEL-28 (malignant melanoma)[1] | 5-20 µM |
| Panc-1 (ductal pancreatic cancer) | 5-20 µM |

[1]B-RAF mutant

In one embodiment, the IC$_{50}$s of the compounds provided herein were determined in cell-based assays using suspension cells. In one embodiment, the activity of the compounds provided herein were determined in a cell-based assay using B-cell acute lymphoblastic leukemia cell lines (Nalm-6, SupB-15, MHH-CALL-4), acute myelogenous leukemia cell lines (Kg1a), or multiple myeloma cell lines (NCI-H929 or U266). In one embodiment, the suspension cells used in the cell-based assays may be a cell type selected from Table 3. Assays with suspension cells were similar except that 40,000-60,000 cells were added to each well and compounds were added immediately after cell plating.

The compounds provided herein were tested in a panel of cell-based assays of suspension cell types. The data is summarized in Table 3.

The IC$_{50}$s of the compounds provided herein and some reference compounds were determined in cell-based assay using triple negative breast cancer cell line MDA-MB-468. The results are summarized in Table 4.

TABLE 3

IC$_{50}$ of Compounds in Suspension Cell Types (µM)

| Cell Line | IC$_{50}$: 1, 2, or 3 |
|---|---|
| Leukemia | |
| Nalm-6 (B-ALL) | 5-8 µM |
| SupB-15 (B-ALL) | 14 µM |
| MHH-CALL-4 (B-ALL) | 16 µM |
| KG1a (AML) | 5-15 µM |
| NCI-H929 (multiple myeloma) | 6-16 µM |
| U266 (multliple myeloma) | 11-20 µM |

TABLE 4

IC$_{50}$ of Compounds in MDA-MB-468 Cells

| Compound Number | Structure | MDA-MB-468 IC$_{50}$ (µM) |
|---|---|---|
| 1 | 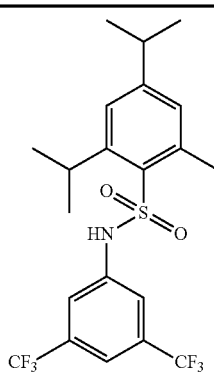 | 5 |
| 2 | 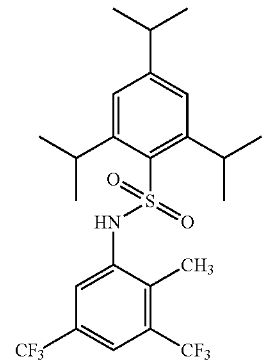 | 2 |
| 3 | 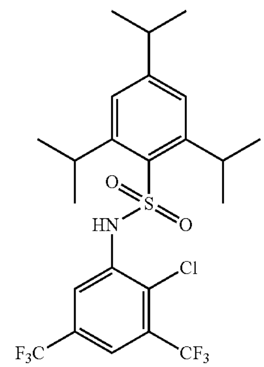 [SMILES: CC(C)c1cc(C(C)C)c(S(=O)(=O)Nc2cc(C(F)(F)F)cc(C(F)(F)F)c2Cl)c(C(C)C)c1] | 4.5 |
| 4 | 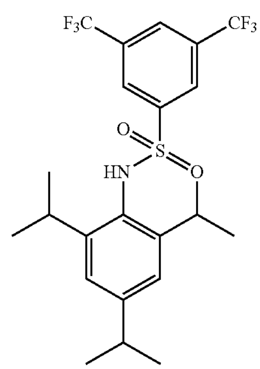 | 12 |
| 5 | 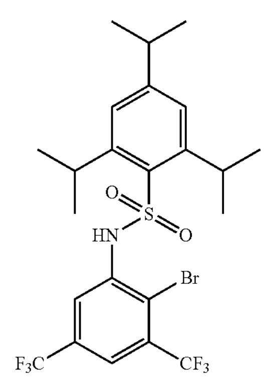 [SMILES: CC(C)c1cc(C(C)C)c(S(=O)(=O)Nc2cc(C(F)(F)F)cc(C(F)(F)F)c2Br)c(C(C)C)c1] | 5 |

TABLE 4-continued

IC$_{50}$ of Compounds in MDA-MB-468 Cells

| Compound Number | Structure | MDA-MB-468 IC$_{50}$ (μM) |
| --- | --- | --- |
| 6 | 4-tert-butyl-2,6-dimethylphenylsulfonamide of 3,5-bis(trifluoromethyl)aniline | 7 |
| 7 | 2,6-diethylphenylsulfonamide of 2-methyl-3,5-bis(trifluoromethyl)aniline | 2 |
| 8 | 2,6-diethylphenylsulfonamide of 3,5-bis(trifluoromethyl)aniline | 1.5 |
| 9 | 4-tert-butyl-2,6-dimethylphenylsulfonamide of 2-methyl-3,5-bis(trifluoromethyl)aniline | 5 |
| 10 | 4-tert-butyl-2,6-dimethylphenylsulfonamide of 2-chloro-3,5-bis(trifluoromethyl)aniline | 3 |
| Reference compound 1 | 3,5-bis(trifluoromethyl)phenylsulfonamide of 3,5-bis(trifluoromethyl)aniline | >20 |
| Reference compound 2 | 2,6-dichlorophenylsulfonamide of 3,5-bis(trifluoromethyl)aniline | 10 |
| Reference compound 3 | 3,5-bis(trifluoromethyl)phenylsulfonamide of 3-chloro-4-cyanoaniline | >20 |

TABLE 4-continued

IC$_{50}$ of Compounds in MDA-MB-468 Cells

| Compound Number | Structure | MDA-MB-468 IC$_{50}$ (µM) |
|---|---|---|
| Reference compound 4 | 2,6-dimethyl-4-methylphenyl sulfonamide of 3,5-bis(trifluoromethyl)aniline | 17 |
| Reference compound 5 | pentamethylphenyl sulfonamide of 3,5-bis(trifluoromethyl)aniline | >20 |
| Reference compound 6 | 2,5-dimethoxyphenyl sulfonamide of 3,5-bis(trifluoromethyl)aniline | >20 |
| Reference compound 7 | 2,4,6-triisopropylphenyl sulfonamide of 4-bromoaniline | 14 |
| Reference compound 8 | 2,4,6-triisopropylphenyl sulfonamide of 2,5-dimethylaniline | >20 |
| Reference compound 9 | 2,4,6-triisopropylphenyl sulfonamide of 3-fluoroaniline | >20 |
| Reference compound 10 | 2,4,6-triisopropylphenyl sulfonamide of 2,4,6-trimethylaniline | >20 |
| Reference compound 11 | 2,4,6-triisopropylphenyl sulfonamide of 2-fluoroaniline | >20 |

TABLE 4-continued

IC$_{50}$ of Compounds in MDA-MB-468 Cells

| Compound Number | Structure | MDA-MB-468 IC$_{50}$ (µM) |
|---|---|---|
| Reference compound 12 | 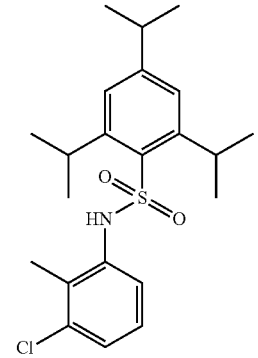 [SMILES: Cc1c(Cl)cccc1NS(=O)(=O)c1c(C(C)C)cc(C(C)C)cc1C(C)C] | 19 |
| Reference compound 13 | 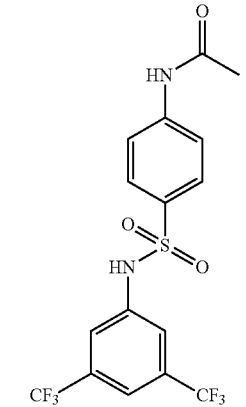 [SMILES: CC(=O)Nc1ccc(S(=O)(=O)Nc2cc(C(F)(F)F)cc(C(F)(F)F)c2)cc1] | >20 |

C. Additional Assays

In one embodiment, the compounds provided herein were assayed for translation inhibition activity using an in vitro HeLa cell extract translation system with an m7GpppN-capped luciferase mRNA reporter. In one embodiment, Compound 1 inhibited luciferase activity at 10 µM by 97.4% vs. DMSO compared to 99.3% inhibition by cycloheximide. Without being limited to any particular theory, the inhibition of luciferase activity was specific to translation inhibition since the compound showed no inhibition of purified luciferase protein at 100 µM.

Cyclin D is one of the most commonly overexpressed genes in breast cancer and high levels correlate with poor prognosis. Furthermore, cyclin D overexpression is correlated with triple-negative basal-like tumors. In one embodiment, the effects of a compound provided herein on cyclin D overexpression were evaluated. MDA-MB-231 cells were treated with 2 µM and 10 µM of Compound 1 and 20 µM cycloheximide (CHX) for 12 h. The density ratio of the cyclin D3 band to respective beta-actin band was determined by Western blot analysis and normalized to DMSO (100%). In one embodiment, 10 µM of Compound 1 showed a decrease in cyclin D3 levels at 18 and 24 h.

Many proteins that drive cancer growth and survival (including the cyclins, c-myc, and Pim-1) have secondary structures in the 5'-UTR of their mRNA that limit the rate of translational initiation. In one embodiment, the effects of a compound provided herein on translation of such mRNAs relative to mRNAs without highly structured 5'-UTRs were evaluated. In one embodiment, Compound 1 showed a preferential inhibition of the highly structured 5'-UTR HB3 (triple stem loop) reporter.

In one embodiment, the compounds provided herein were assayed for inhibition of cancer associated fibroblasts in the tumor stroma. In one protocol, normal human lung fibroblasts (NHLFs) were serum starved for 24 h then treated with or without TGF-β and 0.1% DMSO (control) or 10 µM or 20 µM Compound 1 or Compound 2 for 48 h. Cells were lysed and separated by SDS-PAGE and blotted onto a PVDF membrane and incubated either with anti-α-SMA antibody or with anti-β-actin antibody (FIG. 1).

Figure 2:
FIG. 2 illustrates the effect of Compound 2, and Compounds 5 to 10 on inhibiting α-smooth muscle actin in vitro activity in normal human lung fibroblasts (NHLFs).
Figure 3:
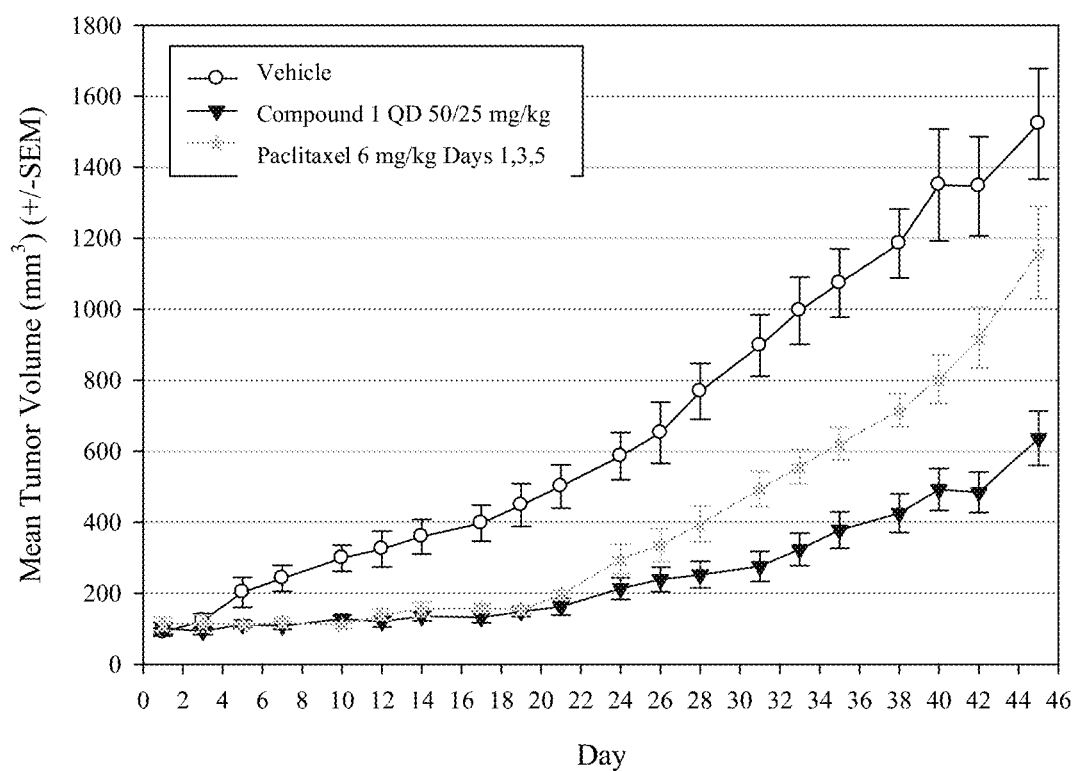
FIG. 3 illustrates the effect (e.g., mean tumor volume) of Compound 1 on inhibiting in vivo tumor growth in the MDA-MB-231 xenograft model for breast cancer in nude mice.
Figure 4:
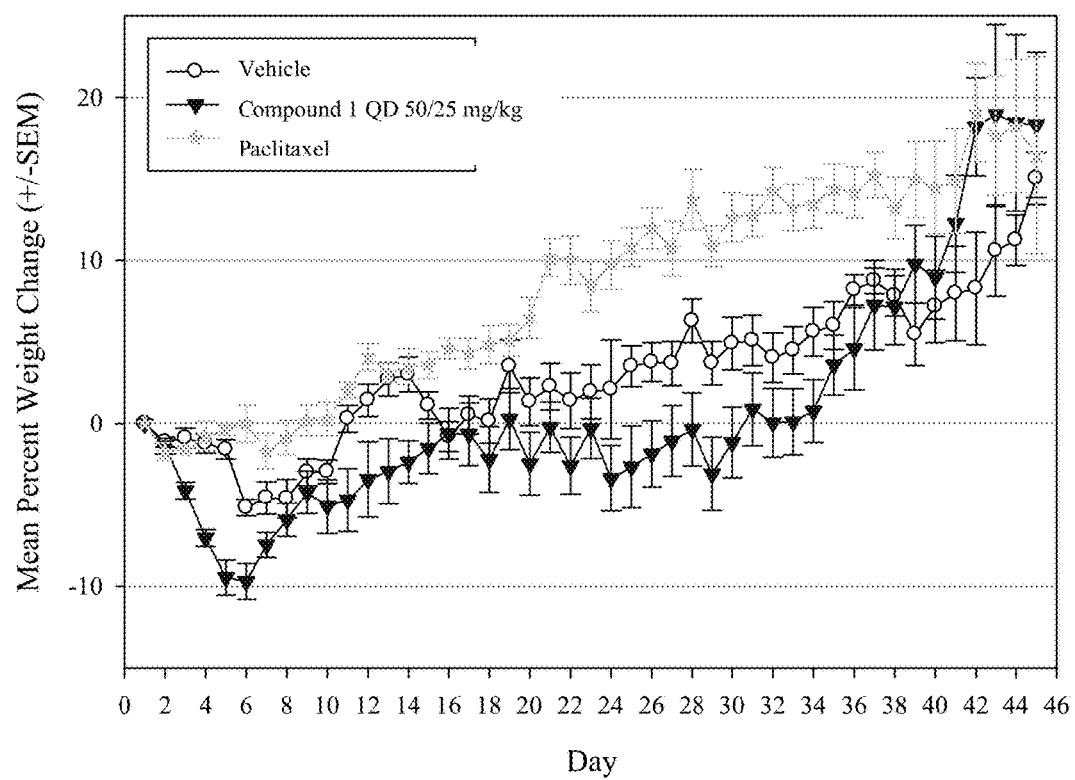
FIG. 4 illustrates the effect (e.g., percent weight change) of Compound 1 on inhibiting in vivo tumor growth in the MDA-MB-231 xenograft model for breast cancer in nude mice.
Figure 5:
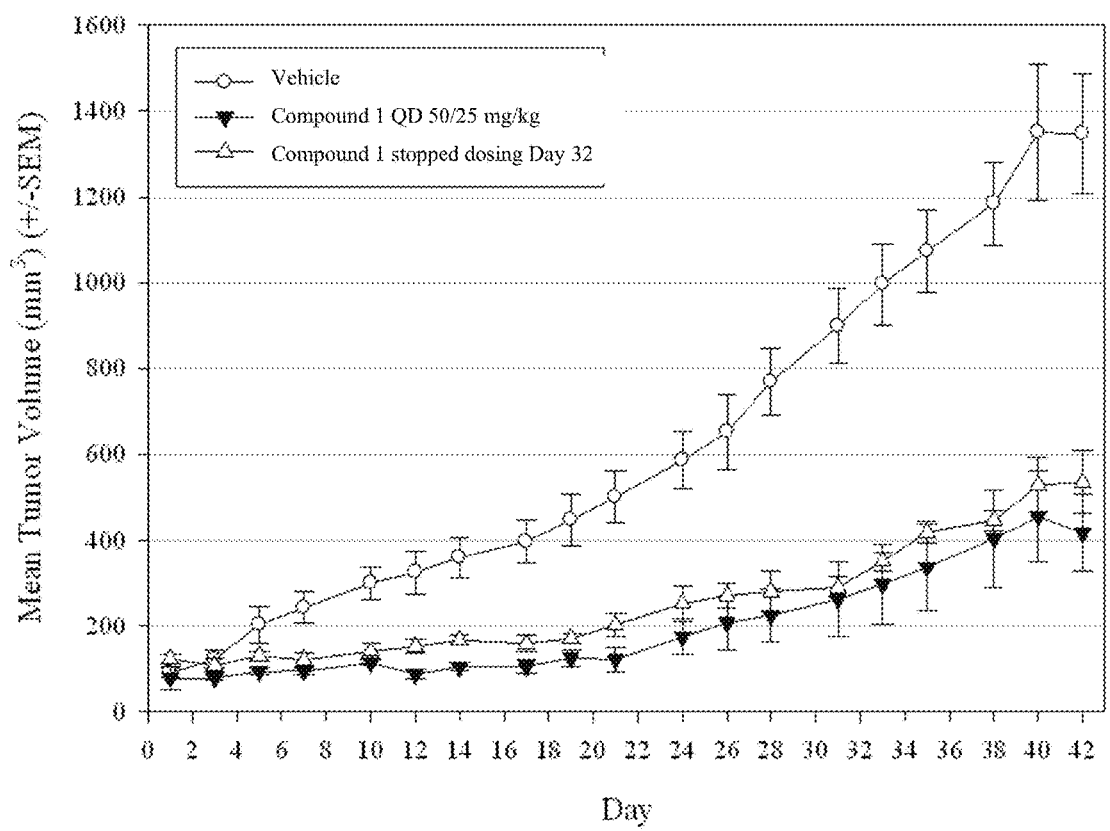
FIG. 5 illustrates the effect of Compound 1 on inhibiting in vivo tumor growth in the MDA-MB-231 xenograft model for breast cancer in nude mice during the drug withdrawl phase.
Figure 6:
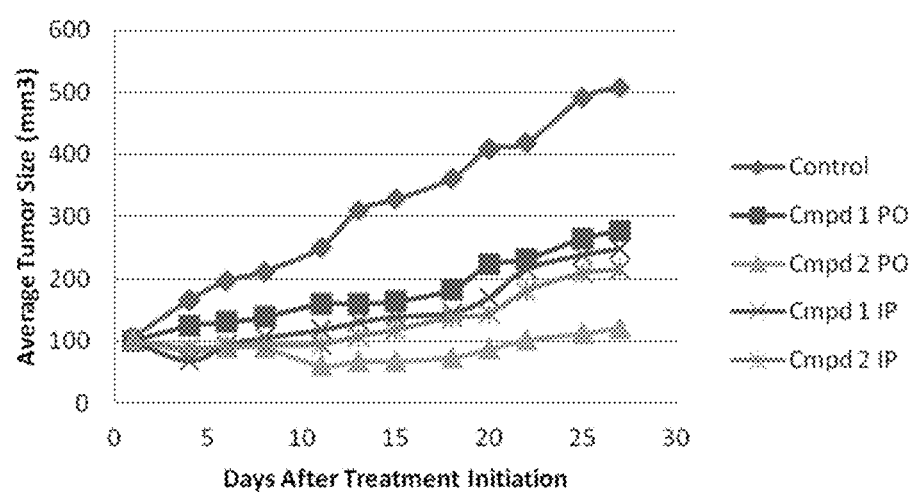
FIG. 6 illustrates the effect (e.g., mean tumor size) of Compound 1 and 2 on inhibiting in vivo tumor growth in the MDA-MB-231 xenograft model for breast cancer in nude mice.

In another typical protocol: normal human lung fibroblasts (NHLFs) in 6-well plates at ~50% confluent were serum starved with DMEM (no FBS) for 24 h and treated with TGF-β [30 ng/ml] and the compounds provided herein [µM] for 48 h. Lysed with 200 µl MPER+HALT per well. 12-well SDS PAGE mini gels were loaded with similar amounts of total proteins as determined by Bradford (15-17 µl per lane). Semi dry transferred to PVDF, blocked for 1 h RT with TBST+1% BSA, 1:5000 mouse anti α-SMA O/N 4C, and 1:5000 anti-mouse HRP 1 h RT. In TBST+1% BSA (FIG. 2).

D. Tumor Growth Inhibition in Mouse Xenograft Model for Breast Cancer

In one embodiment, the effects of a compound provided herein on tumor growth in a mouse animal model were evaluated. In specific embodiments, the mouse animal model was the MDA-MB-231 xenograft model for breast cancer. Studies were performed to evaluate the effect of a compound provided herein on the growth of MDA-MB-231 breast tumors in mice. The test system that was used is summarized below:

| | |
|---|---|
| Species/strain: | Mouse/nude |
| Physiological state: | Immunocompromised |
| Age/weight range at start of study: | Animals aged 5 to 6 weeks with body weight of approximately 20 g |
| Animal supplier: | Charles River Laboratories |
| Number/sex of animals: | 40/female |
| Identification: | Prior to initiation of dosing, animals were identified by ear punching. After randomization, all cages were labeled with protocol number, group, and animal numbers with appropriate color-coding |
| Randomization: | Animals were randomly and prospectively divided into treatment groups of animals each prior to tumor induction. |
| Cell Line: | MDA-MB-231 breast cell carcinoma |
| Cell Line Source: | ATCC (HTB-26) |
| Cell Culture Conditions: | Liebovitz's L-15, 10% FBS, 1% pen/strep |
| Tumor Cell Implant: | 5.0 × 10$^6$ cells, subcutaneously in 50% Matrigel |

Animals were housed 10 mice per cage in micro-isolators, with sterile corn cob bedding, food, and water. Mice were acclimated for 3 days and given food and tap water ad libitum. Animals were examined prior to initiation of the study to assure adequate health and suitability. Animals that were found to be diseased or unsuitable were not assigned to the study. During the course of the study, 12-hour light/12-hour dark cycle were maintained. A nominal temperature range of 20-23° C. with a relative humidity between 30% and 70% was maintained. LabDiet 5053-certified PicoLab Rodent Diet and sterile water were provided ad libitum during the study.

Exemplary Protocol: Ten mice per group were inoculated s.c. on the left flank with 5×10$^6$ MDA-MB-231 cells. When tumors reached a mean volume of approximately 100 mm$^3$, animals began treatment with a compound provided herein (See Table 5). Test article or vehicle were given once daily by IP injection for up to 31 days. Tumors were evaluated every Monday, Wednesday and Friday, body weights and condition were evaluated on a daily basis.

Cell Culture: MDA-MB-231 breast cancer cells were grown in Liebowitz's L-15 with 10% fetal bovine serum and 1% pen/strep. Cells were routinely trypsinized and passaged 1:3. On the day of implantation, cells were washed in PBS, trypsinized and resuspended in complete media. Cells were washed 3× in serum free media (centrifuged 1000 rpm for 5 min). Cells were resuspended to a density of $1 \times 10^8$ cells/mL and diluted 1:1 with Matrigel. Cells were implanted s.c. using a 23G needle in a volume of 0.1 mL.

TABLE 5

Study Groups Treated With Compound

| Group | Number of animals | Inoculum | Test article | Dose | Schedule* |
|---|---|---|---|---|---|
| 1 | 10♀ | MDA-MB-231, $5 \times 10^6$ cells | Vehicle | NA | Once Daily, Days 1 to 31 |
| 2 | 8♀ | MDA-MB-231, $5 \times 10^6$ cells | Compound 1 | 50/25 mg/kg | Once Daily, Days 1 to 31 |
| 3 | 8♀ | MDA-MB-231, $5 \times 10^6$ cells | Paclitaxel | 6 mg/kg | Once Daily, Days 1, 3, 5 |

*Therapy commenced when tumors reach approximately 100 mm³; dosing schedule and dosing amount may be adjusted (e.g., after the initiation of compound treatment) depending on individual compound/experiment.

Tumor Measurement: Tumors were monitored daily. If, during a daily evaluation, an animal's tumor appeared to have exceeded 1500 mm³, the tumor was measured; and animals with tumors greater than 1500 mm³ and/or that had become necrotic and/or hindered movement were euthanized. Tumors were measured twice weekly by measuring each tumor in 2 dimensions, along the largest dimension (length, L) and perpendicular to this dimension (width, W). Tumor weights were calculated using the standard formula: $(L \times W^2)/2$. The mean tumor weight and standard error of the mean were calculated for each group at each time point. An ANOVA was used to compare differences of primary tumor volume.

Animal Weight: All animals were weighed twice weekly throughout the study. Group weight change was expressed as a daily group mean weight. Animals that lost greater than 20% of their total starting body weight were euthanized.

In one embodiment, Compound 1 was dosed in mice at a dose of, for example, qd 50 mg/kg, and the dose was reduced to 25 mg/kg on day 7. In one embodiment, mean tumor volume at Day 31 for the vehicle group was 898±260 mm³, while mean tumor volume at Day 31 for the group of mice treated with Compound 1 was 276±119 mm³. In one embodiment, mean weight gain for the vehicle group was 4.2%, while mean weight gain for the group of mice treated with Compound 1 was 0.1%.

On day 32, the group of mice treated with Compound 1 was subdivided into 2 groups. For the next 10 days, one group continued to receive treatment while the other did not. In one embodiment, tumor growth did not resume within 10 days of the withdrawal of Compound 1.

At study termination, mice still undergoing treatment were given a final dose of compound and sacrificed 2 h later. Average concentrations of compounds in plasma and tumor were determined. In one embodiment, detectable levels of Compound 1 were found in both plasma and tumor samples from the mice that discontinued treatment on Day 31, indicating that less frequent dosing of Compound 1 will likely be an option.

In one embodiment, a triple negative breast cancer xenograft (MDA-MB-231) was performed on Compound 1 and Compound 2 dosed IP and PO. Mean tumor volumes over time were calculated from length and width measurements. Treatment was initiated when average tumor size reached 100 mm³. Compound 1 and Compound 2 were dosed at 50 mg/kg IP and 100 mg/kg PO. Doses were either skipped or cut in half for those mice that lost >15% of their body weight. The tumor growth inhibition data is summarized in FIGS. 3-6 and Table 6.

TABLE 6

Plasma and Tumor Concentrations of Lead Compounds at Sacrifice

| Compound No. | Treated until the end? | No. of Animals | Treatment Dose | Day Sacrificed | Ave. Plasma Conc. (µM) | Ave. Tumor Conc. (µM/g of tumor tissue) |
|---|---|---|---|---|---|---|
| 1 | Yes | 3 | 50/25 mg/kg | 45 | 2.33 ± 0.27 | 1.25 ± 0.09 |
| 1 | No | 4 | None after day 31 | 45 | 0.05 ± 0.02 | 0.07 ± 0.04 |

TABLE 7

Comprehensive PK studies and Oral Bioavailability of Compounds 1 and 2

| Compound | IV Administration (5 mg/kg) C0 (ng/mL) | IV Administration (5 mg/kg) T1/2 (h) | PO Administration (25 mg/kg) C0 (ng/mL) | PO Administration (25 mg/kg) T1/2 (h) |
|---|---|---|---|---|
| Compound 1 Mouse | 54,647 | 2.1 | 5150 | 1.5 |
| Compound 2 Mouse | 53,652 | 2.9 | 3613 | 2.4 |
| Compound 2 Rat | 68,933 | 1.6 | 27,600 | ND (>>6) |

Animals were dosed at 5 mg/kg IV and 25 mg/kg PO. Plasma samples were collected at times ranging from 0 to 6 h and analyzed by LC-MS/MS.

The examples set forth above are provided to give those of ordinary skill in the art with a complete disclosure and description of how to make and use the claimed embodiments, and are not intended to limit the scope of what is disclosed herein. Modifications that are obvious to persons of skill in the art are intended to be within the scope of the following claims. All publications, patents, and patent applications cited in this specification are incorporated herein by reference as if each such publication, patent or patent application were specifically and individually indicated to be incorporated herein by reference in their entireties.

What is claimed:

1. A method of treating or ameliorating fibrosis in a subject, comprising administering to the subject a compound of formula (II):

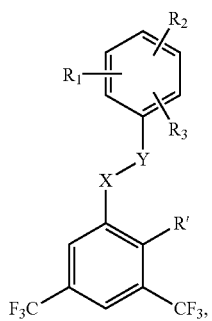

(II)

or an enantiomer, a mixture of enantiomers, or a mixture of two or more diastereomers thereof;
or a pharmaceutically acceptable salt, solvate, hydrate, or prodrug thereof, wherein:
X is NH, and Y is $S(O)_2$; or X is $S(O)_2$, and Y is NH;
R' is hydrogen, halogen, $(C_1-C_4)$alkyl, or $(C_1-C_4)$alkoxy, wherein the alkyl and alkoxy are each optionally substituted with one or more halogen;
$R_1$ is independently $(C_1-C_6)$alkyl, $(C_2-C_8)$alkenyl, $(C_2-C_8)$alkynyl, or $(C_3-C_8)$cycloalkyl, each of which is optionally substituted with one or more halogen;
$R_2$ is independently hydrogen; or $(C_1-C_6)$alkyl, $(C_2-C_8)$alkenyl, $(C_2-C_8)$alkynyl, or $(C_3-C_8)$cycloalkyl, each of which is optionally substituted with one or more halogen; and
$R_3$ is independently $(C_1-C_6)$alkyl, $(C_2-C_8)$alkenyl, $(C_2-C_8)$alkynyl, or $(C_3-C_8)$cycloalkyl, each of which is optionally substituted with one or more halogen.

2. The method of claim 1, wherein the compound has formula (II-A):

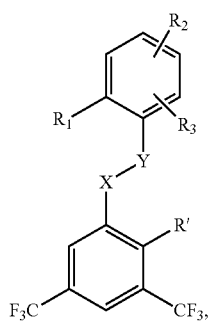

(II-A)

or an enantiomer, a mixture of enantiomers, or a mixture of two or more diastereomers thereof;
or a pharmaceutically acceptable salt, solvate, hydrate, or prodrug thereof.

3. The method of claim 2, wherein the compound has formula (II-A-1):

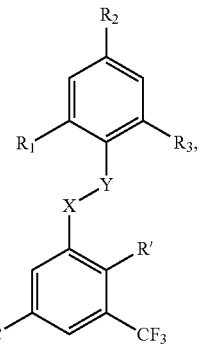

(II-A-1)

or an enantiomer, a mixture of enantiomers, or a mixture of two or more diastereomers thereof;
or a pharmaceutically acceptable salt, solvate, hydrate, or prodrug thereof.

4. The method of claim 1, wherein X is NH, and Y is $S(O)_2$.

5. The method of claim 1, wherein X is $S(O)_2$, and Y is NH.

6. The method of claim 3, wherein the compound has formula (III-A-1):

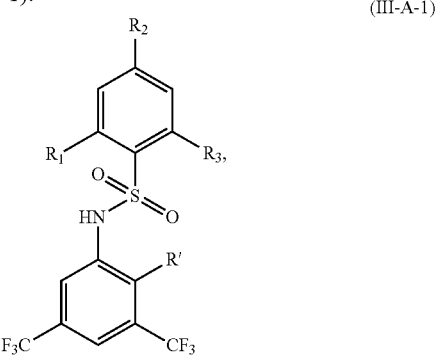

(III-A-1)

or an enantiomer, a mixture of enantiomers, or a mixture of two or more diastereomers thereof;
or a pharmaceutically acceptable salt, solvate, hydrate, or prodrug thereof.

7. The method of claim 1, wherein R' is hydrogen, halogen, or $(C_1-C_4)$alkyl optionally substituted with one or more halogen.

8. The method of claim 1, wherein R' is hydrogen, F, Cl, Br, $(C_1-C_4)$alkyl, $CF_3$, or $OCF_3$.

9. The method of claim 1, wherein R' is hydrogen, Cl, Br, or $(C_1-C_4)$alkyl.

10. The method of claim 1, wherein R' is hydrogen, chloro, bromo, or methyl.

11. The method of claim 1, wherein R' is hydrogen.

12. The method of claim 1, wherein R' is methyl.

13. The method of claim 1, wherein R' is chloro.

14. The method of claim 1, wherein R' is bromo.

15. The method of claim 1, wherein $R_1$, $R_2$, and $R_3$ are independently $(C_1-C_6)$alkyl, $(C_2-C_8)$alkenyl, $(C_2-C_8)$alkynyl, or $(C_3-C_8)$cycloalkyl.

16. The method of claim 1, wherein $R_1$ is $(C_1-C_4)$alkyl.

17. The method of claim 1, wherein $R_1$ is methyl, ethyl, or isopropyl.

18. The method of claim 1, wherein $R_2$ is hydrogen, or $(C_1-C_4)$alkyl.

19. The method of claim 1, wherein $R_2$ is methyl, isopropyl, or tert-butyl.

20. The method of claim 1, wherein $R_3$ is $(C_1-C_4)$alkyl.

21. The method of claim 1, wherein $R_3$ is methyl, ethyl, or isopropyl.

22. The method of claim 4, wherein the compound is:
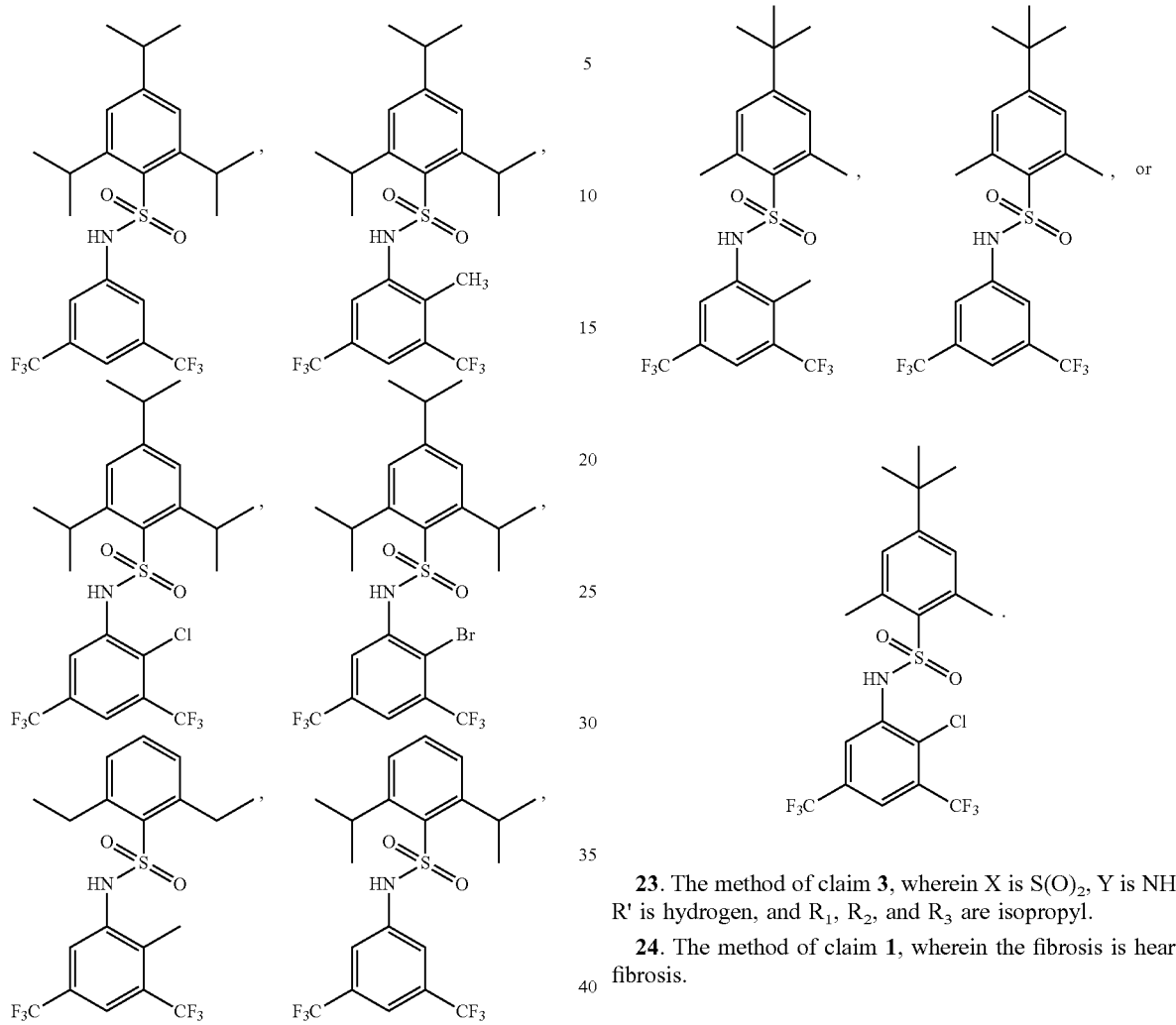
23. The method of claim 3, wherein X is $S(O)_2$, Y is NH, R' is hydrogen, and $R_1$, $R_2$, and $R_3$ are isopropyl.
24. The method of claim 1, wherein the fibrosis is heart fibrosis.
* * * * *